United States Patent [19]

Oberhardt

[11] Patent Number: 5,110,727
[45] Date of Patent: * May 5, 1992

[54] METHOD FOR PERFORMING COAGULATION ASSAYS ACCURATELY, RAPIDLY AND SIMPLY, USING DRY CHEMICAL REAGENTS AND PARAMAGNETIC PARTICLES

[75] Inventor: Bruce J. Oberhardt, Raleigh, N.C.

[73] Assignee: Cardiovascular Diagnostics, Inc., Research Triangle Park, N.C.

[*] Notice: The portion of the term of this patent subsequent to Jul. 18, 2006 has been disclaimed.

[21] Appl. No.: 192,672

[22] Filed: May 10, 1988

Related U.S. Application Data

[63] Continuation-in-part of Ser. No. 33,817, Apr. 3, 1987, Pat. No. 4,849,340.

[51] Int. Cl.5 .................. G01N 1/12; B01L 3/00; C12M 1/14
[52] U.S. Cl. .................. 435/13; 435/310; 435/305; 435/810; 436/46; 436/69; 436/809; 422/57; 422/58; 422/60; 422/73; 422/102; 422/110; 422/292; 73/863.71; 73/863.72; 73/864.72
[58] Field of Search .......... 435/13, 310, 805, 810; 436/809, 46, 69; 422/57, 58, 73, 102, 110, 292; 73/863.71–863.72, 864.72

[56] References Cited

U.S. PATENT DOCUMENTS

| | | | |
|---|---|---|---|
| 3,294,641 | 12/1966 | Lorand | 436/69 |
| 3,520,659 | 9/1970 | Steinberg et al. | 422/73 |
| 3,650,698 | 3/1972 | Adler | 422/73 X |
| 4,088,488 | 5/1978 | Lilja et al. | 422/102 X |
| 4,323,536 | 4/1982 | Columbus | 422/56 |
| 4,438,068 | 3/1984 | Forrest | 422/61 |
| 4,473,639 | 9/1984 | Sommer et al. | 435/13 |
| 4,480,030 | 10/1984 | Svendsen | 435/13 |
| 4,537,861 | 8/1985 | Elings et al. | 436/518 |
| 4,672,030 | 6/1987 | Witt | 435/13 |
| 4,696,797 | 9/1987 | Kelton | 422/101 |
| 4,756,884 | 7/1988 | Hillman et al. | 422/73 |
| 4,761,381 | 8/1988 | Blatt et al. | 436/165 |
| 4,775,515 | 10/1988 | Cottingham | 422/73 |
| 4,786,603 | 11/1988 | Wielinger et al. | 436/69 |
| 4,849,340 | 7/1989 | Oberhardt | 435/13 |
| 4,861,712 | 8/1989 | Bartl et al. | 435/13 |

FOREIGN PATENT DOCUMENTS 460038 4/1974 Australia.

OTHER PUBLICATIONS

Webster's New World Dictionary of the American Language, College Edition (The World Publishing Company, Cleveland), 1968, p. 1519.

Primary Examiner—Esther L. Kepplinger
Assistant Examiner—Carol A. Spiegel
Attorney, Agent, or Firm—Oblon, Spivak, McClelland, Maier & Neustadt

[57] ABSTRACT

A method and apparatus for the measurement of clot formation times, clot dissolution times, or clotting parameters is disclosed. This method performs these measurements by monitoring movement of magnetic particles incorporated in the sample being assayed, where the movement is induced by a magnetic field.

58 Claims, 31 Drawing Sheets

METHOD FOR PERFORMING COAGULATION ASSAYS ACCURATELY, RAPIDLY AND SIMPLY, USING DRY CHEMICAL REAGENTS AND PARAMAGNETIC PARTICLES

This application is a continuation-in-part of application Ser. No. 07/033,817, filed Apr. 3, 1987, now U.S. Pat. No. 4,849,340.

BACKGROUND OF THE INVENTION

1. Field of the Invention

The present invention relates to a method for the facile performance of coagulation assays, for example, diagnostic assays (medical diagnostics).

2. Discussion of the Background

In this document, the term "coagulation assay" is used to denote a class of assays which includes (i) clotting or clot formation assays, (ii) clot lysis assays, and (iii) clotting parameter(s) assays.

Blood clotting reactions, in general, employed as clinical assays measure the time required for the formation of a fibrin clot. The most common of these reactions is the prothrombin time test.

Many approaches exist for measuring clot formation in prothrombin time assays. All of these clot formation based assays utilize thromboplastin to react with the patient's blood sample. Available approaches differ in the means used to detect when clot formation occurs. They may also differ in the types of apparatus used and in the constituents of and/or additives to the reagent.

Blood clotting assays are principally used for screening, diagnosis, and for monitoring patients receiving anticoagulant therapy. There are many types of coagulation assays. These include prothrombin time (PT), partial thromboplastin time (PTT), activated partial thromboplastin time (APTT), fibrinogen assay, thrombin clotting time (TCT), activated clotting time (ACT), etc. The most frequently performed of these assays is prothrombin time.

A principal use of prothrombin time (PT) determinations is to monitor patients receiving oral anticoagulants such as warfarin. An accurate monitoring of coagulation in these patients is important to prevent recurrent clotting (thrombosis) and to keep the coagulation mechanism sufficiently active to prevent spontaneous bleeding. Prothrombin time testing provides information to permit better drug control to be achieved through the regulation of drug dosage.

In conventional practice, PT assays are performed by the addition of a liquid reagent to a plasma sample. The reagents are typically supplied in dried form and consist primarily of tissue thromboplastin and calcium chloride. The dried reagent is reconstituted before use by addition of a measured amount of distilled water.

These reagents are thermally sensitive, and refrigeration prior to use is required. The shelf life of the reagent in dried form is from one to two years. However, when it is reconstituted the reagent is considerably more labile and must be used within a few hours or discarded. In some cases reconstituted reagents can be kept for a few days under refrigeration.

Prothrombin time assays are performed by mixing sample and reagent at 37° C., and monitoring the progress of the reaction until a perceptible clot (or "gel clot") is detected. The development of a gel clot is the end point of the reaction. This end point may be detected in various ways; by viscosity change, by electrode reaction, and, most commonly, by photometric means. The test result is generally compared to a result using a normal (control) plasma.

Before performing the test, a blood sample is collected in a tube or syringe containing anticoagulant (citrate). The blood sample is centrifuged, and the plasma separated (e.g., by decantation) from the red blood cells. A measured quantity (usually 0.1 ml) of plasma is pipetted into the reaction vessel or cuvette. A measured amount of reagent is then added manually via pipette or automatically by means of other volumetric delivery systems capable of metering a known, preset quantity of reagent. Alternatively, the sample can be added to the reagent directly.

Typically, 0.2 ml of reagent is employed. The addition of the reagent initiates the reaction. Existing blood clotting assays, and in particular PT assays, all suffer from at least one of the following disadvantages: difficulty in performance, requirement of highly trained personnel, inaccuracy in measurement, reagent instability, large consumption of reagent, etc.

There is thus a strongly felt need for a simple, facile and accurate method for the performance of blood clotting assays, e.g., in medical application. Such a method should be based on a minimum number of manipulations of either a sample or reagent. Ideally such a method should be easily utilized by persons without extensive clinical laboratory training and should require no sample or reagent-containing solution preparation. It should not suffer the problems associated with reagent instability and be very accurate. It should permit effective mixing of sample and reagent. It should require only a very small amount of sample. And it should be able to perform automatic treatments of the sample, e.g., it should not require centrifugation of the blood sample or any other off line cell separation process. Available clot lysis assays and clotting parameter assays likewise suffer salient disadvantages.

Clotting parameter assays are referred to herein as function and structure-based assays in the broad realm of coagulation diagnostics which do not utilize clot formation or clot lysis processes to generate end points. Most of these assays utilize chromogenic synthetic substrates to quantify molecular markers or specific factors or components associated with coagulation. These are typically functional reaction based assays as opposed to most immunoassays which could detect the same molecules but utilize structure recognition and may therefore still identify inhibited components or defective components, neither of which may be functional. The present invention does not deal specifically with immunoassays but may be generally applicable to homogeneous chromogenic and fluorogenic immunoassays.

SUMMARY OF THE INVENTION

Accordingly, it is an object of this invention to provide a simple and facile method for performing a clotting or clot lysis or clotting parameter assay.

It is another object of this invention to provide a facile and accurate method for performing a clotting or clot lysis or clotting parameter assay.

It is another object of this invention to provide a method for performing a highly accurate clotting or clot lysis or clotting parameter assay.

It is another object of this invention to provide a method for performing a coagulation assay requiring no preparation of reagent-containing solution.

It is another object of this invention to provide a method for performing a coagulation assay which minimizes problems associated with reagent instability.

It is another object of this invention to provide a method for performing a coagulation assay which is highly accurate and reproducible.

It is another object of this invention to provide a method for performing a coagulation assay which is very precise.

It is another object of this invention to provide a method for performing a coagulation assay which permits an effective mixing of sample and reagent(s).

It is another object of this invention to provide a method for performing a coagulation assay requiring only a very small amount of sample.

It is an object of this invention to provide a novel element which permits the facile and accurate performance of diagnostic coagulation assays.

It is another object of this invention to provide such an element which can be used in diagnostic coagulation assays without requiring the preparation of a reagent solution from dry reagent.

It is another object of this invention to provide such an element permitting the accurate and reproducible coagulation assay of samples with minimum sample manipulation.

It is another object of this invention to provide a novel element permitting the precise coagulation assay of samples with minimum sample manipulation.

It is another object of this invention to provide a novel element for performing a diagnostic coagulation assay in which no measurement of sample or reagent is required for performance of the assay.

It is another object of this invention to provide a novel element for performing a diagnostic coagulation assay permitting optimum accuracy.

It is another object of this invention to provide a novel element for performing a diagnostic coagulation assay permitting the effective mixing of sample and reagent(s).

It is another object of this invention to provide a novel element for performing a diagnostic coagulation assay requiring only a very small amount of sample.

It is another object of this invention to provide a novel element for performing a diagnostic coagulation assay capable of performing assays on whole blood without separating red blood cells from plasma.

It is another object of this invention to provide a novel reagent for coagulation assays.

Surprisingly, all of these objects, and other objects which will become apparent from the description of the invention provided herein below, have all been satisfied with the discovery of the present method for performing coagulation or clot lysis assays.

The present invention can be used to measure clot formation times, clot dissolution (lysis) times, and clotting parameters. In its basic aspect, the assay provided by the invention comprises the following steps. A first component of the assay, charged with magnetic particles, is placed on a reaction holding means, e.g., substantially flat surface, a reaction slide, or a microtiter plate. The first component is then subjected to the action of (1) a stationary oscillating magnetic field or (2) a moving permanent magnetic field or (3) a combination of an oscillating field and a stationary permanent magnetic field. A second component of the assay is then added to the first component, and the effect of the magnetic field(s) or the moving permanent magnet on the magnetic particles is monitored.

In one of its aspects, the method is used for performing a blood clotting assay. In this application the following sequence of steps are used:

(1) adding a measured amount of a liquid sample to be assayed to a reaction holding means, e.g., a substantially flat surface, a reaction slide, or a microtiter plate, charged with a combination of (i) magnetic particles and (ii) at least one dry reagent, wherein the combination is arranged in a substantially distributed or a substantially flattened format;

(2) subjecting said combination to (1) an oscillating magnetic field or (2) a moving permanent magnetic field or (3) a combination of an oscillating magnetic field and a stationary magnetic field; and (3) monitoring the movement of the magnetic particles.

In another aspect, the method is used for performing a clot dissolution (lysis) assay. In this application the following sequence of steps are used:

(1) adding a sample with a clot dissolving component to a reagent charged with magnetic particles and disposed on a reaction holding means, e.g., a substantially flat surface, a reaction slide, or a microtiter plate, where said clotted sample is subjected (1) to an oscillating magnetic field or (2) to a moving permanent magnetic field or (3) to a combination of an oscillating magnetic field and a stationary permanent magnetic field; and (2) monitoring the movement of the magnetic particles.

There are different manners in which the initial step of adding a sample with a clot dissolving component to a reagent charged with magnetic particles discussed above may be practiced. Thus instead of adding a sample with a clot dissolving component to a reagent charged with magnetic particles, it is possible to add a sample containing a clot dissolving reagent to a reagent charged with magnetic particles. It is also possible to add a sample containing clot dissolving component(s) or initiator(s) or inhibitor(s) of clot dissolving processes to a reagent charged with magnetic particles. Alternatively it is possible to add a sample containinq a clot dissolving component(s) or initiator(s) of clot dissolving processes to a reagent charged with magnetic particles which will first initiate clot formation and then allow clot lysis to occur.

This method can be advantageously performed in a novel reaction slide which forms part of this invention.

The present invention also provides a reaction slide equipped with a membrane for monitoring assays which develop color (i.e. chromogenic assays) or which involve color change.

In a performing such a chromogenic assay, e.g., a clotting parameter(s) assay, the present invention comprises adding a sample to the sample well of an element comprising a channel structure defining a sample well and a reaction volume in communication with each other, wherein the reaction volume is defined by an upper surface having attached thereto a membrane, wherein the element contains a measured amount of at least one reagent in the reaction volume. A specific volume of the sample is drawn into the reaction volume by capillary action and contacts the membrane and the reagent to initiate a reaction between the sample and the reagent. The reaction is monitored by monitoring any color change in the membrane.

BRIEF DESCRIPTION OF THE FIGURES

A more complete appreciation of the invention and many of the attendant advantages thereof will be readily obtained as the same becomes better understood by reference to the following detailed description when considered in connection with the accompanying drawings, wherein like reference numerals designate identical or corresponding parts throughout the several views.

FIGS. 37 and 38 illustrate an apparatus that may be used in conducting two different assays from the same sample.

DETAILED DESCRIPTION OF THE PREFERRED EMBODIMENTS

Figure 1A:
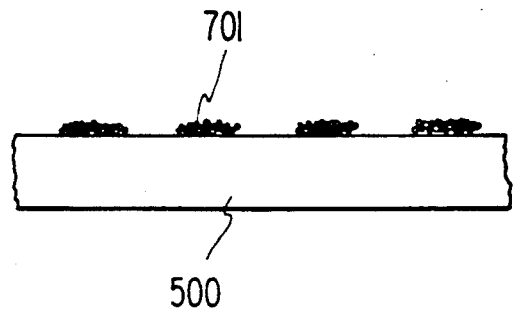
FIGS. 1a and 1b illustrate the combination of magnetic particles and dry reagent after the addition of sample on the flat surface at a magnification of approximately 100× showing clusters of particles undergoing oscillation between orientation states. Under the influence of the magnetic field, the particles form columnar structures or stacks. Although it is not known exactly how this happens, under the light microscope at a magnification of 100×, these stacks were observed. In the stacks, the individual particles were too small to be resolved. Each stack resembled a cylindrical object or stalk with an irregular surface and a somewhat variable diameter along the length of the clyinder. Some stalks were thinner then others.

In one general embodiment, the present invention provides a novel approach to monitoring coagulation assays by monitoring the movement of magnetic particles.

In another general embodiment, the present invention provides a dry reagent containing magnetic particles, where the dry reagent is a reagent used in a coagulation assay.

Application to Coagulation Assays

The invention provides a method for performing a coagulation assay on a sample comprising:

In another embodiment the method for performing a coagulation assay on a sample comprises:

(i) adding a first component required for the assay to a second component required for the assay, wherein said second component comprises a reagent charged with magnetic particles, and wherein said second component is subjected to (1a) an oscillating magnetic field or (1b) a moving permanent magnetic field or (1c) a combination of an oscillating magnetic field and a stationary permanent magnetic field; and (ii) monitoring movement induced in said magnetic particles by said either oscillating magnetic field or said moving permanent magnetic field or said combination of an oscillating field and said stationary permanent magnetic field to perform said assay.

Another embodiment is a method for performing a coagulation assay, comprising:

(1) adding a sample to the sample well of an element comprising a channel structure defining a sample well and a reaction volume in communication with each other, wherein said reaction volume is defined by an upper surface having attached thereto a membrane or a gel layer, wherein the element contains a measured amount of at least one reagent situated in said reaction volume; wherein a specific volume of the sample is drawn into the reaction volume by capillary action and contacts said membrane and said reagent to initiate a reaction between the sample and the reagent; and (2) monitoring said reaction.

In another embodiment, the element contains a combination of at least one reagent and magnetic particles situated in said reaction volume.

The invention also provides a reagent for a coagulation assay, the improvement comprising wherein said reagent is in dry form and contains magnetic particles.

In another embodiment, the reagent for a coagulation assay is a reagent for a fibrin clot assay.

In another embodiment, the reagent for a coagulation assay is a thromboplastin calcium reagent.

In another embodiment, the reagent for a coagulation assay is a partial thromboplastin reagent with calcium chloride.

In another embodiment, the reagent for a coagulation assay is a partial thromboplastin reagent with calcium chloride and an activator.

In another embodiment, the reagent for a coagulation assay is thrombin.

In another embodiment, the reagent for a coagulation assay is a reagent for a lysis assay.

In another embodiment, the reagent for a coagulation assay is a fibrin clot lysis assay.

In another embodiment, the reagent for a coagulation assay is a plasminogen activator assay reagent containing plasminogen and either fibrin or thrombin.

In another embodiment, the reagent for a coagulation assay is a plasmin assay reagent containing either fibrin or thrombin.

In another embodiment, the reagent for a coagulation assay is a plasminogen assay reagent containing a plasminogen activator and either fibrin or thrombin.

In another embodiment, the reagent is streptokinase or urokinase.

In another embodiment, the reagent is natural or synthetic tissue plasminogen activator.

In another embodiment, the reagent for a coagulation assay is an alpha-2-antiplasmin assay reagent containing fibrin and plasmin.

Application to Clotting Assay

The invention provides a method for performing a clotting assay, comprising:

(1) adding a measured amount of a liquid sample to be assayed to a combination of (i) magnetic particles and (ii) at least one dry reagent, said combination being situated on a reagent holding means, being arranged in a substantially distributed or a substantially flattened format, and being subjected to (1a) an oscillating magnetic field or (1b) a moving permanent magnetic field or (1c) a combination of an oscillating magnetic field and a stationary permanent magnetic field; and (2) monitoring movement of said magnetic particles.

In another embodiment, the method is a method for performing a clotting assay in an element for performing said assay, comprising:

(1) adding a liquid sample to said element, wherein said element comprises a channel structure defining a sample well and a reaction volume in communication with each other, said channel structure having a geometry causing said liquid sample placed in said sample well to be drawn into and filling said reaction volume via capillary action, wherein after said reaction volume is filled said liquid sample remains stationary therein, said reaction volume being charged with a combination of (i) magnetic particles and (ii) at least one dry reagent, and wherein said magnetic particles are subjected to (1a) an oscillating magnetic field or (1b) a moving permanent magnetic field or (1c) a combination of an oscillating magnetic field and a stationary permanent magnetic field; and (2) monitoring the movement of said magnetic particles.

In another embodiment, the element comprises a means for channeling light from an outside source to said reaction volume.

In another embodiment, the element comprises a means for detecting light scattered from said reaction volume.

In another embodiment, the element is disposed in close proximity to a permanent magnet and an electromagnet, and wherein said movement of said magnetic particles is caused by an oscillating magnetic field produced by an electromagnet.

In another embodiment, the element is disposed in close proximity to a permanent magnet and an electromagnet, wherein the element is situated between said permanent magnet and said electromagnet, and wherein said movement of said magnetic particles is caused by an oscillating magnetic field produced by said electromagnet.

In another embodiment, the reagent has incorporated therein the magnetic particles.

In another embodiment, the sample comprises whole blood.

In another embodiment, the sample comprises plasma.

In another embodiment, the magnetic particles are caused to oscillate by applying an oscillating magnetic field thereto.

In another embodiment, the magnetic particles are caused to move by applying a moving permanent magnetic field thereto.

In another embodiment, the dry reagent comprises thromboplastin calcium reagent.

Application to clot lysis assays

The invention also provides a method for performing a clot lysis assay comprising contacting a patient's blood or plasma sample, a dry reagent containing at least one clot producing reagent and paramagnetic particles, and optically monitoring movement in said particles induced by a magnetic field; and monitoring said movement to determine clotting and lysis endpoints on the same sample.

In another embodiment, the invention provides a method for performing an assay on biochemical components which are involved in clot lysis or in activation or inhibition of clot lysis. This method comprises:

(1) adding a measured amount of sample to a reagent containing a standardized clot charged with magnetic particles, wherein the reagent charged with magnetic particles is situated on a substantially flat surface, and is subjected to (1a) an oscillating magnetic field or (1b) a moving permanent magnetic field or (1c) a combination of an oscillating magnetic field and a stationary permanent magnetic field; and (2) monitoring the movement of said magnetic particles.

In another embodiment, the method is a method for performing a clot lysis assay, comprising:

(1) adding a measured amount of a clot dissolving reagent or of a sample containing a clot dissolving component to a clotted sample charged with magnetic particles, wherein said clotted sample charged with magnetic particles is situated on a substantially flat surface, and is subjected to (1a) an oscillating magnetic field or (1b) a moving permanent magnetic field or (1c) a combination of an oscillating magnetic field and a stationary permanent magnetic field; and (2) monitoring the movement of said magnetic particles.

In this embodiment, the clot lysis assay may be used as a tissue plasminogen activator assay.

In yet another embodiment, the sample itself may be acted upon by the reagent to which it is added such that the sample first forms a clot and later, subject to clot lysis initiators, components, and/or drugs contained in the sample, undergoes clot lysis, where the clot formation and clot lysis processes are both monitored and diagnostic information derived therefrom.

Application to clotting parameter(s) assays

The invention also provides an element for performing a clotting parameter assay. The element comprises therein a channel structure defining a sample well and a reaction volume in communication with each other, wherein said reaction volume is defined by an upper surface having attached thereto a semipermeable layer, e.g., a membrane or a gel layer, said channel structure having a geometry causing a liquid sample placed in the same sample well to be drawn into and filling the reaction volume via capillary action, wherein after the reaction volume is filled the liquid sample remains stationary therein. In another embodiment, the semipermeable layer is a means for monitoring a reaction in the reaction volume.

In another embodiment at least one dry reagent is contained within the semipermeable layer.

In another embodiment at least one dry reagent layer is situated at the surface of the semipermeable layer that is not affixed to the transparent surface.

In another embodiment the reagent contains at least one enzyme.

In another embodiment the semipermeable layer is made up of a plurality of laminated membrane units, wherein each membrane contains at least one dry reagent.

In another embodiment, the element is charged with a combination of magnetic particles and at least one dry reagent.

The invention also provides a kit for performing a coagulation assay comprising a permanent magnet, a timing means and a reaction slide charged with at least one dry reagent charged with paramagnetic particles.

In another embodiment, the invention comprises a transfer pipette, made of an essentially nonthrombogenic material, and capable of capturing a blood sample from a skin puncture site and to transfer said sample to said element containing said dry reagent.

Figure 49:
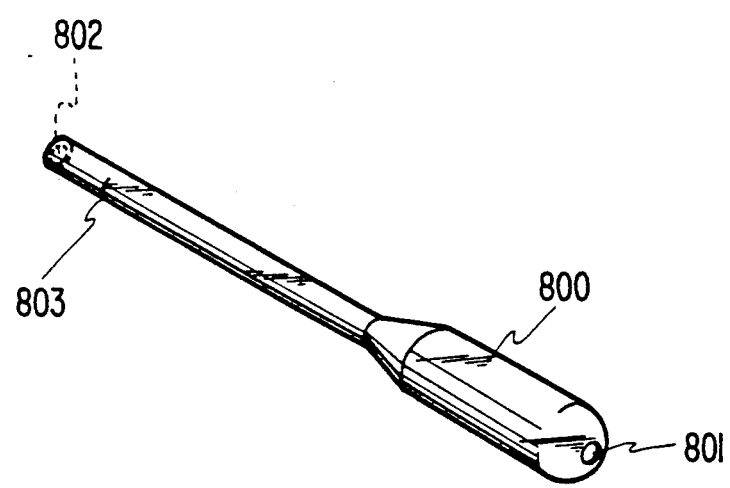
FIG. 49 illustrates a sample applicator which can be used with the present invention.

In another embodiment, the kit contains a pipette to collect and transfer or apply a sample, especially a single sample drop. The pipette which is illustrated in FIG. 49 can be made of a polyolefin eyedropper type applicator to transfer sample from a source (e.g. a finger puncture site or even a test tube) to the sample well of a reaction slide. A preferred applicator contains a stem with a capillary bore (802) and a bulb (800) with a hole (801) in it. The hole is left uncovered when filling via capillary action through the open tip of the stem to a pre-marked fill line (803) or beyond. The hole is covered, e.g., with a finger, and the bulb squeezed to expel sample. In a preferred embodiment, the interior of the capillary may be treated with surfactant.

The invention also provides a system for performing blood coagulation measurements comprising an instrument with means for temperature control, means for producing an oscillating magnetic field or a moving permanent magnetic field capable of causing magnetic particle movement, an illuminating means, and containing at least one dry reagent charged with paramagnetic particles and capable of accepting a sample of whole blood or plasma, means for photometrically monitoring said magnetic particle movement and interpreting the results of said magnetic particle movement to perform assay determinations, and an element containing said reagent.

Magnetic particle movement

In the present invention, magnetic particles are induced to move by being subjected to either (1) an oscillating magnetic field or (2) a moving permanent magnetic field or (3) a combination of an oscillating magnetic field and a stationary permanent magnetic field. The movement (oscillation or flicker) of the magnetic particles is then monitored in the performance of the assay.

The oscillating magnetic field is generated by an oscillating magnetic field generating means which is itself stationary with respect to the reagent holding means, e.g. a substantially flat surface, on which, the assay is performed. As illustrated in FIGS. 1a and b both the oscillating magnetic field or the moving permanent magnetic field causes the magnetic particles situated on the flat surface 500 to aggregate into columnar aggregates 701 and 702. These aggregates are caused to change between orientation states 701 and 702 by the oscillating magnetic field to create what appears to the naked eye of an observer to be a "flicker" or periodic fluctuations between bright and dim reflected or scattered light.

Thus under the influence of the oscillating magnetic field or the moving permanent magnetic field the particles, as observed under magnification, aggregate to form cylindrical or columnar shapes which undergo an approximately 90° change in orientation to produce bright and dim reflected or scattered observable light.

Figure 8:
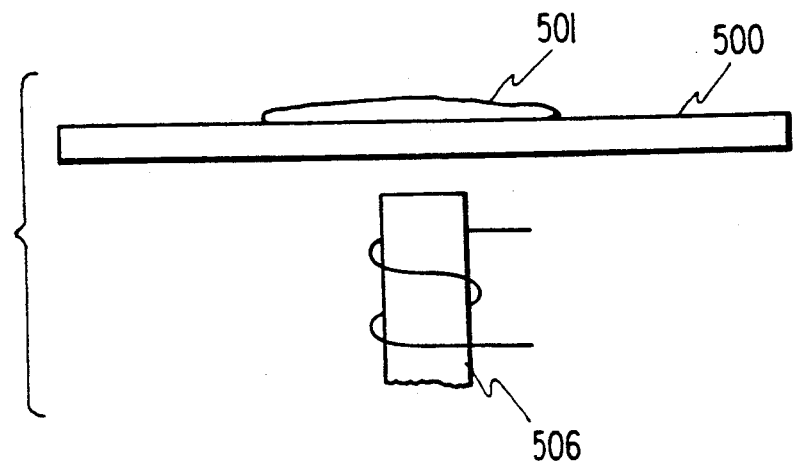
FIG. 8 illustrates the method of causing magnetic particle oscillation to create the flicker phenomenon using a single electromagnet.

FIG. 8 illustrates the substantially flat surface 500 charged with a combination of reagent and magnetic particles 501 and an oscillating magnetic field generating means 506.

Figure 7A:
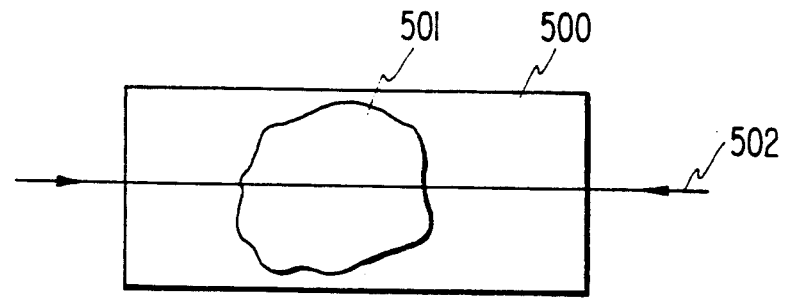
FIGS. 7a and 7b illustrate two views of the method of causing magnetic particle oscillation to create the flicker phenomenon using a linear simple motion of a single permanent magnet.
Figure 7B:
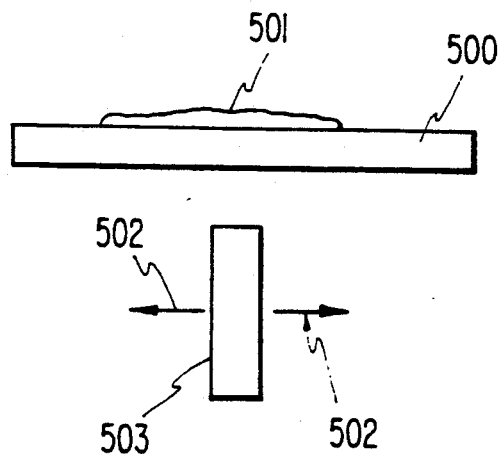
Figure 9A:
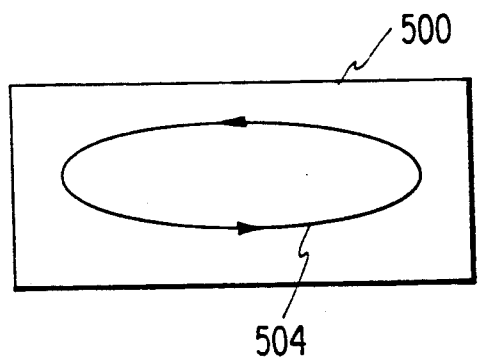
FIGS. 9a and 9b illustrate two views of a method of causing magnetic particle oscillation to create the flicker phenomenon using an orbital motion of a single permanent magnet.
Figure 9B:
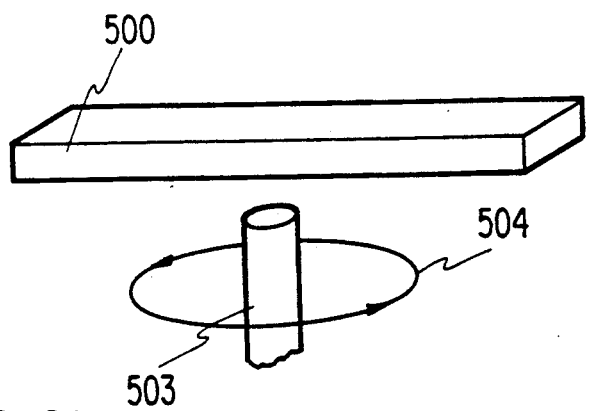

As illustrated in FIGS. 7(a and b) the moving permanent magnetic field is generated by a permanent magnetic field generating means which is moved in a direction parallel to the major plane of the substantially flat surface, line 502 in FIGS. 7(a and b) and line 504 in FIG. 9. This moving permanent magnetic field causes a similar aggregation and movement phenomena in the magnetic particles as is observed with the oscillating magnetic field.

Figure 6A:
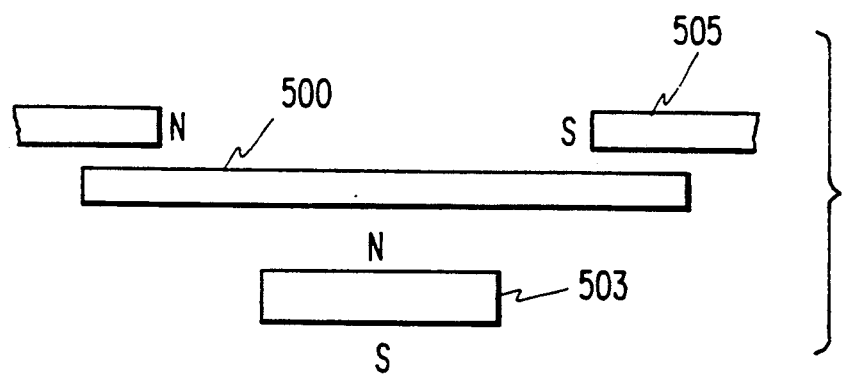
FIGS. 6a and 6b illustrate two views of a substantially flat surface on which the present assays can be practiced together with magnetic field generating means in an arrangement suitable for measuring a coagulation reaction.
Figure 6B:
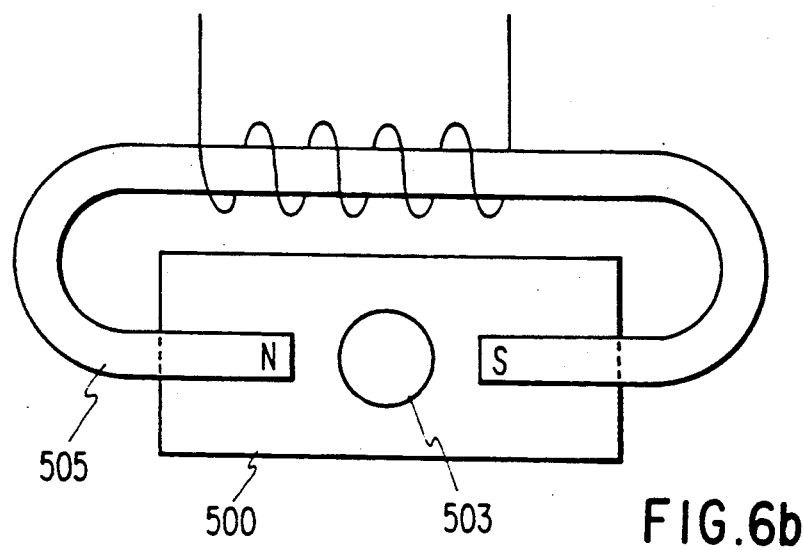

In a preferred embodiment of the invention, illustrated in FIGS. 6(a and b), a combination of an oscillating magnetic field and a stationary permanent magnetic field are used. In this embodiment, both the permanent magnet 503 and the oscillating magnetic generating means 505 are held stationary with respect to the reaction holding means, the substantially flat surface 500, on which the assay is being performed.

In a clotting reaction the diminution of the movement of the magnetic particles identifies the clotting endpoint. In a clot lysis reaction the onset of increased movement of the magnetic particles identifies the clot lysis end-point.

The reaction holding means

The clotting and clot lysis assays of this invention are performed on a reaction holding means. This reaction holding means can be any means which will support the reagents used in the assay and permit monitoring movement of the magnetic particles. Such reaction holding means include microtiter plates, their equivalents, substantially flat surfaces or the reaction slide provided by the present invention discussed below.

The reagents

The reagents used in the present invention are those used in the assays described herein. The are distinguished by the fact that they contain, in intimate admixture, magnetic particles. The magnetic particles are present in an amount of 0.5, or lower, to 50 milligrams of magnetic particles, preferably 1 to 10 milligrams, per milliliter of dry reagent.

The assays

Clotting assay(s)

Some of the key elements, parameters and features of the present method for performing clotting assays (i.e. prothrothrombin time) are discussed below.

One of the important characteristics of the present invention is that it uses (i) a reaction holding means, e.g., a substantially or essentially flat reaction surface and (ii) a flattened or thin mixture of reagent(s) and magnetic particles. The surface of the reagent and magnetic particles composition is configured such that the surface area of reagent-sample mixture (or projected area) is great in relation to its volume.

The methodology associated with dry reagents containing paramagnetic particles is not very reproducible and therefore not very helpful unless the sample is added to a dry reagent arranged in a distributed or essentially flattened format rather than in a cubic or spherical volume. The distributed or flattened format facilitates dissolution of the reagent. In addition, and more importantly, the distributed or flattened format provides a larger viewing area for clot formation to be monitored.

Figure 16:
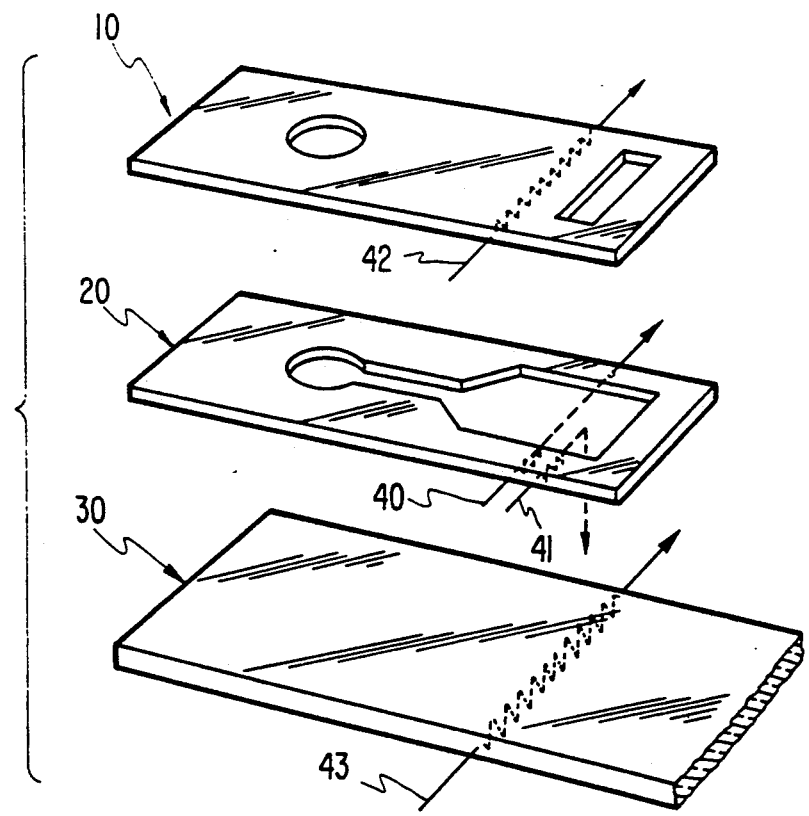
FIG. 16 is an exploded perspective of the items shown in FIGS. 13-15, the elements being oriented as in the assembled reaction slide.

Although a capillary slide geometry such as that of the reaction slide described in greater detail below, see, e.g., FIG. 16, is ideally suited for creating a properly flattened format, housing the reagent, and metering the sample, the assay will work perfectly well by simply adding a premeasured amount of sample to a solid surface (e.g., a microtiter plate well or a substantially flat surface) containing a dry reagent having paramagnetic particles incorporated therein. Thus, an acceptable result can be obtained without a reaction slide. In this aspect of the invention a simple, a general reaction holding means is used.

It is important that the dry reagent be prepared such that it can be rapidly dissolved upon the addition of the blood or plasma sample. Freeze drying on a surface, or even better, between two surfaces closely apposed at a capillary or near capillary distance works best. This produces a mass of low matter content which enables rapid sample penetration and dissolution.

Although freeze drying has provided the best results for preparation of a dry paramagnetic particle based PT reagent, room temperature, vacuum, desiccant, convective, or other types of drying can also be used to achieve good results. For example, room temperature air drying of reagent on the base of a reaction slide (with spacer in place) followed by attachment of the cover can produce a self metering dry reagent containing element.

The ratio of sample to combination reagent and magnetic particles which can be used to achieve good assay results is variable. If there are too many magnetic particles, the surface where the reaction takes place will be very dark and crowded, and it may be difficult to read the "flicker" signal. If the particles are too few, the flicker signal may be too weak, and signal-to-noise ratio would be low.

In a typical prothrombin time reaction, 0.2 milliliters (200 microliters) of thromboplastin calcium reagent is added to 0.1 milliliter of plasma sample. Small variations may affect the assay reproducibility. In general, instruments which handle liquid reagents measure coagulation using a total of 300 microliters of reaction mixture. To use less liquid reagent or sample could require a more expensive instrument, capable of monitoring smaller reaction volumes, and could introduce pipetting error, depending upon how small.

In the dry reagent reaction system, approximately 25 microliters of thromboplastin-calcium reagent containing paramagnetic particles (at approximately 5 to 50 milligrams per milliliter of liquid) is lyophilized to produce a dry reagent. However, 0.5 to 5 milligrams per milliliter may be successfully employed to make a good reagent, and even less than 0.5 milligram per milliliter in the actual reaction slide may be used (vide infra). To this dry reagent, approximately 25 microliters of plasma (or whole blood) sample is added to perform the assay. Thus, the 2:1 ratio of reagent to plasma is replaced by a 1:1 proportion of solutes in a given volume of sample.

The concentration of the reagent in the final reaction mixture is important also. Since the dry reagent system requires dissolution of reagent prior to reaction with the liquid sample, the reagent cannot be too concentrated, or it will not completely dissolve when sample is added. If the reagent is too dilute, poor endpoints can result.

Based on data obtained on thromboplastin from two sources, no clear cut rule has yet been established. One source gave elevated PT assay values when concentration was increased (up to two-fold) from the recommended norm and decreased values when concentration was decreased (up to one quarter of normal). The other source, studies over a narrower range (diluted up to one quarter of the recommended norm) showed the opposite trend.

The calcium component of the reagent is particularly important. In the absence of calcium, the reagent will only work well with whole blood without an anticoagulant, such as blood collected in a syringe from a venipuncture site or with a lancet from a finger stick site. In the presence of calcium, whole blood collected in a tube or syringe with citrate anticoagulant can be assayed, as can the plasma prepared from the citrated blood.

In the absence of calcium or at very low calcium concentrations, the prothrombin time of citrated blood or plasma is significantly lengthened. Clotting can be totally inhibited if there is insufficient calcium to overcome the effects of the anticoagulant. In the presence of excess calcium, the prothrombin time is also lengthened, and an extreme excess (greater than 25 millimoles per liter) could compromise the effectiveness of the assay. There is, however, a range of calcium concentrations over which the dry reagent assay will yield the shortest clotting times and will be effective for performing prothrombin time determinations on citrated plasma, citrated whole blood, venipuncture collected whole blood without anticoagulant, and fingerstick whole blood (without anticoagulant). For this reagent, (calcium) a range would be from approximately 8 to 13 mmole/liter calcium. However, different thromboplastin reagents may require different calcium concentration optima. The range of 8 to 13 millimoles is therefore only a general guideline.

The optimal calcium concentration occurs in the vicinity of 8 millimoles to 18 millimoles per liter, preferably 8 millimoles to 13 millimoles per liter, and most preferably at about 10 millimoles per liter. At or near 10 millimoles per liter calcium concentration, variations in calcium due to calcium level differences from patient to patient do not alter the test results.

The novel method of this invention can be advantageously applied not only to prothrombin time assays, but also to many other types of conventional clinical coagulation assays, especially those which measure a fibrin clot as an endpoint.

The basic reaction slide (e.g. the slide illustrated in FIG. 17) or simply a substantially flat surface may be utilized in accordance with the invention with various dry reagents to perform a variety of coagulation assays. For example, the present method may be advantageously used with:

1. thromboplastin calcium reagent and magnetic particles to provide a prothrombin time (PT) assay;
2. partial thromboplastin reagent with calcium chloride and magnetic particles to provide a partial thromboplastin time (PTT) assay;
3. partial thromboplastin reagent with calcium chloride and activator and magnetic particles to provide an activated partial thromboplastin time (APTT) assay;
4. thrombin reagent and magnetic particles to provide a thrombin clotting time (TCT) assay; or
5. with variation in concentration of reagent and sample to provide a fibrinogen assay. Many other coagulation reactions are also possible in accordance with the present invention, for example using the slide illustrated in FIG. 17.

There are a few known prothrombin time assays which utilize dry reagents. There are also a few prothrombin time assays which utilize magnetic particles in the reagent. None has been able to successfully combine both dry reagents and magnetic particles, which is now provided for the first time with this invention in its coagulation assay aspect.

Simply trying to dry or freeze dry the reagents in the few available systems which are based on magnetic particles will not work and will defeat the purpose of those systems (all of which are based on the handling of liquid components). Adding magnetic particles to the very few available dry reagent systems will provide no additional enhancement since these approaches do not measure any optical properties of paramagnetic particles and could not be simply adapted to do so.

Clotting parameter assay(s)

Figure 11:
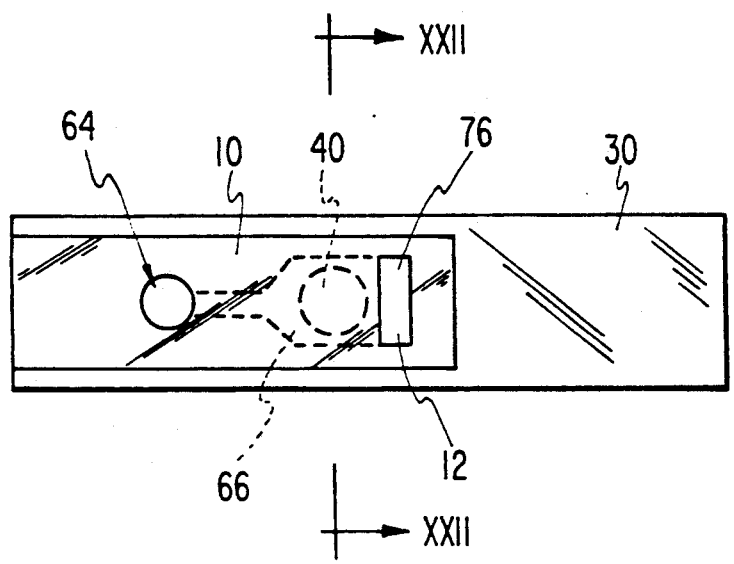
FIG. 11 illustrates a reaction slide with a membrane as an integral part of the reaction volume to effect species separation prior to or after a chemical reaction, to provide for containment of reagents within the membrane, if required, and to allow convenient reflectance measurements to be made.
Figure 12:
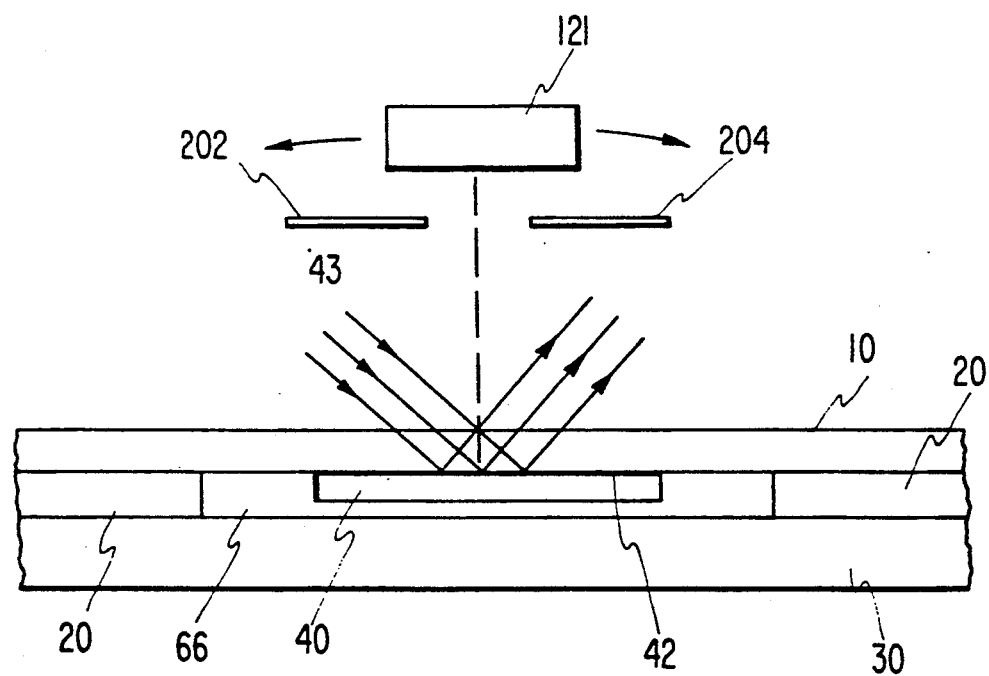
FIG. 12 is a sectional view of the reaction slide of FIG. 11 equipped with a membrane, illustrating how a reflectance measurement may be made.

Another preferred embodiment provides the reaction slide illustrated in FIGS. 11 and 12 which is discussed in greater detail infra. This embodiment provides a slide equipped with a semipermeable layer, e.g., a membrane or a gel layer, monitoring means, and may be used to perform a wide variety of other assays. As illustrated in FIG. 11 the reaction slide provided by this embodiment of the invention is equipped with a semipermeable layer 40 which is situated within reaction volume 66. This layer is available to absorb liquid and dissolved species from the assay sample. This causes changes in the layer which can be monitored via reflectance measurements, providing a measurement of the assay.

There are hundreds of possibilities for the uses of this embodiment. In relation to blood coagulation, measurement of coagulation variables using various synthetic chromogenic substrates has led to many new assays.

Some examples are: antithrombin III, heparin, plasminogen, $\alpha_2$-antiplasmin, and factor X. These newer amidolytic methods are commercially available in kits, and the number of still newer assays based on these synthetic substrate methods is ever increasing. Some of these are described, e.g., by Fareed, et al., Clin. Chem. 29/2 225-236 (1983) and Svendsen, et al., Seminars in Thrombosis and Hemostasis. 9/4, 250-262 (1983).

The synthetic substrates are molecules which upon enzymatic cleavage release p-nitroaniline. This produces a pale yellow color. An absorption peak exists near 405 nanometers, and this is where the reaction is typically measured. Using this method, a spectrophotometer, semi-microcuvettes, a centrifuge to spin the blood and separate the plasma, a water bath at 37° C., and a stop watch are typically required. For initial rate measurements, a photometer with a 37° C. thermostated cuvette housing is typically required.

Using the reaction slide in FIG. 11, synthetic substrate assays can be performed without the requirement of prior plasma separation. In this case, an appropriate membrane for blood cell separation is utilized along with a 400 nanometer optical filter on the photodetector (photodiode). Using chromogenic synthetic substrate S-2251 (H-D-Val-Leu-Lys-pN$_4$2HCl) which is commercially available in combination with the dried reagents which follow, the following whole blood assays can be performed:

1. tissue plasminogen activator, S-2251, and buffers for a plasminogen (total available plasmin) assay;
2. S-2251 and buffers for a free plasmin assay;
3. plasmin and S-2251 for an alpha-2-antiplasmin assay; and
4. plasminogen, fibrin fragments, S-2251, and buffers for a tissue plasminogen activator (t-PA) assay.

This embodiment of the present invention does not require the presence of magnetic particles. These can be advantageously used, however, for example by being situated in reaction space 40 illustrated in FIG. 12, where they serve to improve mixing.

Clot lysis assay(s)

As noted above, the present invention is also useful to perform assays based upon clot dissolving or clot lysis.

Clot lysis types of assays come in a variety of forms and have been used for a variety of purposes. A variety of these assays are described below. These assays do not all measure the same biochemical parameters. Many give results which do not relate to results from other methods.

Euglobulin Lysis Time—This test is based on acidification of a patient's plasma to precipitate fibrinogen and fibrinolytically active components. The precipitate is then redissolved in a buffer and clotted. The time for the complete lysis or dissolution of this clot at 37° C. is referred to as euglobulin lysis time. Normal euglobulin lysis times range between 3 and 4 hours, may be shortened to 2 hours in patients with excessive fibrinolysis and to 30 minutes in patients with a clinically significant degree of hemorrhage.

Dilute Blood or Plasma Clot Lysis Time—These methods involve diluting a patient's plasma or whole blood, clotting the sample with thrombin, and observing the sample at 37° C. for clot lysis. Normal subjects vary over a wide range of from 2 to 24 hours, or more.

Fibrin Plate Method—This method utilizes plasma or its euglobulin fraction as a sample. The sample is placed on a plate containing a thin layer of standardized fibrin clot. After a period of 17 to 20 hours of incubation, areas of lysis are measured. The assay is reported to be accurate and has been used to measure fibrinolytic activity, plasmin, and plasminogen. The test takes too long to be useful in monitoring thrombolytic therapy.

Lysis of Labeled Fibrin Substrates—These assays employ a radioactive isotope label or fluorescent label on fibrin. When fibrin is digested during the lytic process, fragments are released which may be quantitatively measured. These assays may be performed in 1 to 2 hours.

Thromboelastography—These methods employ various types of apparatus to measure the shear elasticity of the clot. These methods generally take many hours to perform lysis assays.

Caseinolytic Methods—Casein, a protein found in milk, can serve as a substrate for the enzyme plasmin. By measuring the rate of casein degradation using fluorescent or radioactive labels, this method can be used to assay for plasminogen activator, plasminogen, or plasmin.

The above approaches are discussed by H. C. Kwaan in Disorders of Fibrinolysis, Medical Clinics of North America 1972:56, 163-176. None of the above approaches are convenient to use, and in general, these methods are not adaptable to whole blood measurements. Some are very slow, requiring many hours to obtain a result. Some require expensive apparatus. These approaches are in general not suitable for real time monitoring of patients receiving thrombolytic therapy with drugs such as t-PA, streptokinase, urokinase, etc.

More recent methods for assaying biochemical components associated with clot lysis using esters of amino acids which act as substrates for plasmin. These synthetic substrates when cleaved by the enzyme plasmin release a chromophore or fluorophore and develop color (or fluorescence) which can be monitored.

Although the amino acid ester or amidolytic methods and also caseinolytic methods are relatively specific, and substrates for plasmin are involved, there have been some concerns expressed in the scientific literature that fibrin is the real substrate and that therefore assay methods which are not based on fibrin will not be as specific. Nevertheless, amidolytic methods, in particular, have gained acceptance.

The present invention also provides a semipermeable layer-equipped element for performing whole blood assays for the first time with these types of methods, thereby greatly increasing convenience of using these assays. Other assays related to clot lysis include measurement of fibrin degradation products (FDP) or fragments which are broken off as the clot is lysed. These are primarily immunoassays. Immunoassays may be utilized to measure other factors related to fibrinolysis, as well. Immunoassay results, however, may not have an exact relationship to metabolically or functionally active concentrations of analyzed biochemical species; since damaged and biochemically inhibited species will probably still be detected.

Various efforts to improve clot lysis assays include an apparatus which gently rocks tubes back and forth for many hours to help clots within these tubes to lyse, allowing subsequent released liquid from the clot to be collected in sufficient quantity to be detected by completing a circuit between two electrical contacts thereby signalizing an endpoint at the completion of clot lysis (H. J. Wilkens and N. Back, American Journal of Clinical Pathology 66, 124–131 (1976). A semiautomatic method for clot lysis assays utilizing the rising of air bubbles released from the clot as it dissolves, developed 20 years ago is still being used: D. Collen, G. Tytgat, and M. Verstraete, American Journal of Clinical Pathology 21, 705–707 (1968). More recent improvements include refinements in the fibrin plate method by accurately measuring circular areas of digested thin layers of fibrin on the plates: J. Jespersen and T. Astrup, Haemostasis 13:301–315 (1983).

Fibrinolytic Assays have been recently performed in microtiter places and automated using computer compatible microtiter plate readers, which measure optical density and can detect when the clot is digested: D. P. Beebe and D. L. Aronson, Thrombosis Research 47:123–128 (1987). R. H. Carlson, R. L. Garnick, A. J. S. Jones and A. M. Meunier more recently showed feasibility of using a turbidity measurement (absorbance versus time) made on a standardized clot in a microcentrifugal analyzer to assay for t-PA concentration in a buffer: Analytical Biochemistry 168, 428–435 (1988).

None of the above described available methods are convenient to use for real time monitoring of whole blood samples in applications such as t-PA assays, plasminogen assays, etc. The methodology provided by the present invention can perform convenient, rapid whole blood clot lysis based assays using dry reagents to determine specific levels of substances such as: plasminogen activators (t-PA, streptokinase, urokinase, etc.); plasminogen; plasmin; inhibitors; etc.

The assay may be used in several ways:

1. Exogenous Clot Lysis Based Methods—Here a standardized clot made from fibrin (fibrinogen-thrombin reaction) is combined with paramagnetic particles in a dry reagent format. The dry reagent may also contain other factors, such as a high concentration of plasminogen (for plasminogen activator assays). The whole blood sample is added, and the paramagnetic particle motion is monitored, as previously described. The release of particles from the clot indicates the onset of lysis, and the time to reach this onset, as well as the kinetics of the early stages of lysis are proportional to the concentration of lytic factors being assayed.

2. Endogenous Clot Lysis Based Methods—Here, a dry reagent slide containing thrombin (or a thrombin-like snake venom, such as atroxin, which is less heparin sensitive than thrombin), paramagnetic particles, and possibly other components, is utilized. A sample of the patient's blood is added. This blood forms a clot due to the effect of thrombin on the patient's fibrinogen. The lysis assay is then carried out on the patient's own clot, instead of on a standardized clot, thereby revealing information about the patient's fibrin; for example, its susceptibility to lysis by a known amount of t-PA.

A novel aspect of the present invention is the use of magnetic particles entrapped within the clot. As the clot is dissolved, more magnetic particles become free to undergo movement (oscillation), and the flicker signal increases.

In this way it is possible to measure clot lysis promoters, such as tissue plasminogen activator using the reaction slide and magnetic particles. For example, as may be seen in FIGS. 10(a and b), a dry reagent slide containing a preformed fibrin clot, plasminogen, and magnetic particles is used to perform a convenient t-PA assay in the reaction slide configuration illustrated in FIG. 17. This can also be achieved, but with considerably greater difficulty, using the same dry reagents and alternating magnetic field without a reaction slide on a surface or in an appropriate container.

Figure 10A:
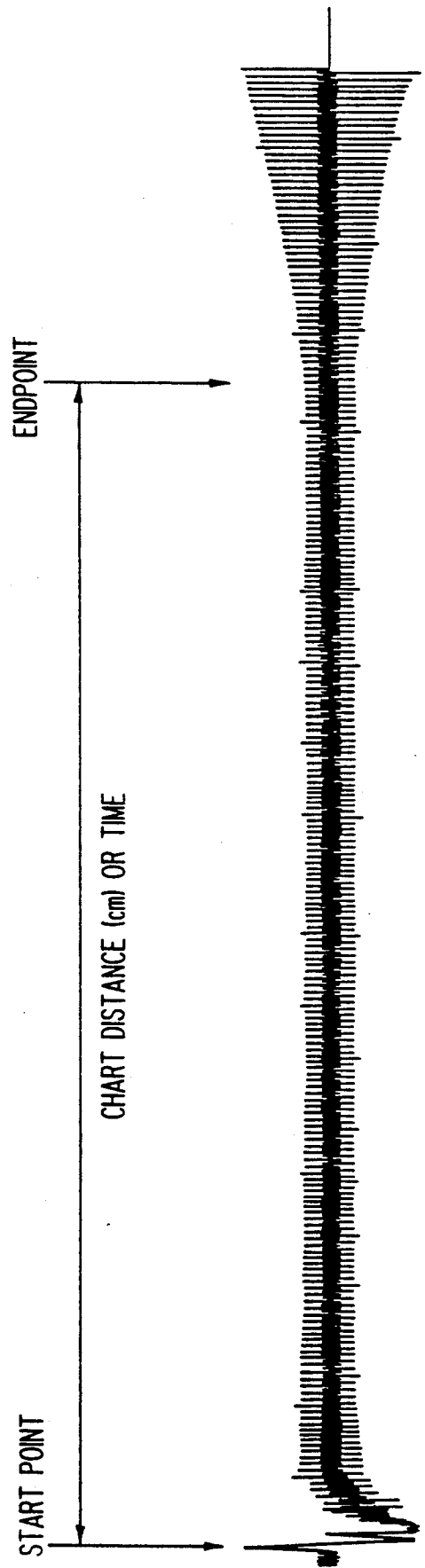
FIGS. 10a and 10b illustrate a tracing obtained by monitoring the optical signal of oscillation between orientation states of the magnetic particles in a clot lysis assay and a standard curve used in making the measurement.
Figure 10B:
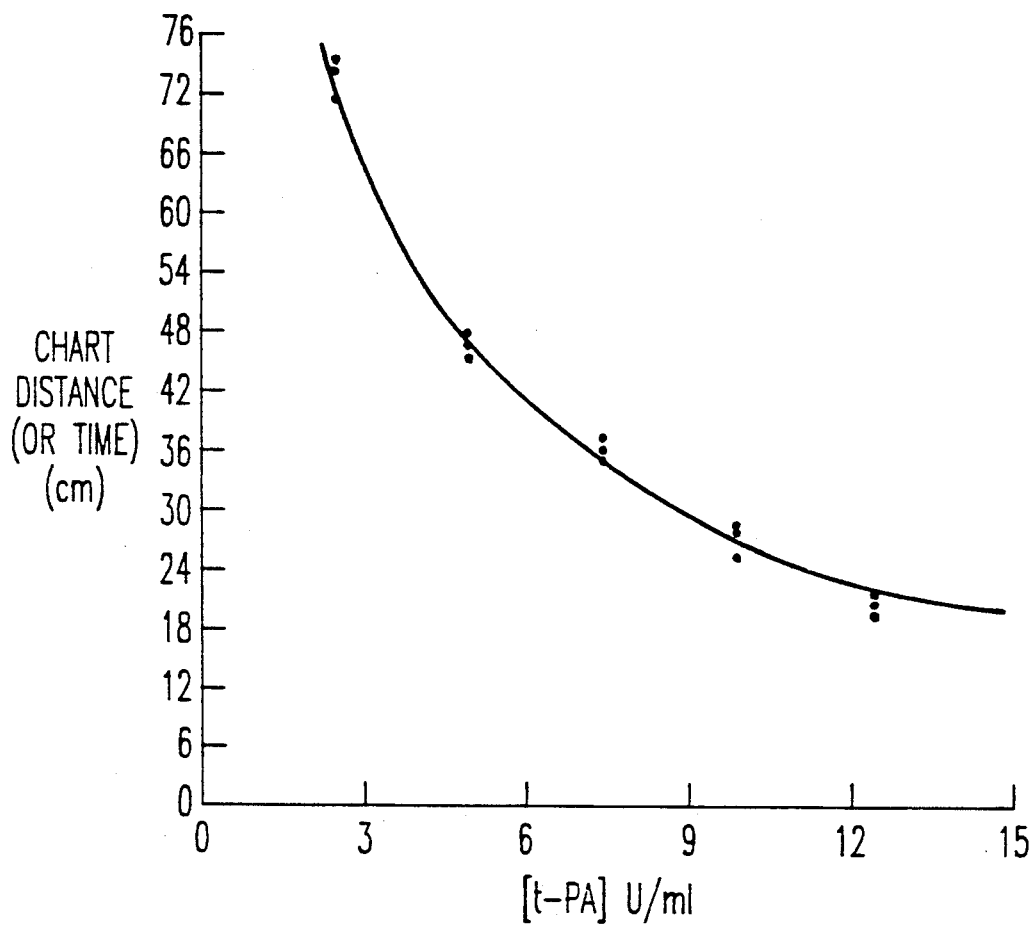

In FIGS. 10(a and b), whole blood t-PA assay is shown. The endpoint is the point at which the flicker signal begins to increase above threshold value or produce a distinct slope change. The total time (start point to endpoint) is inversely related to concentration of t-PA and is highly reproducible. The same assay can be used to quantify other plasminogen activators by using appropriate standard curves for calibration.

A similar approach may be used in other assays, such as to detect plasminogen or total available plasmin, using a whole blood sample. In the case of plasmin detection, a slide containing magnetic particles, and a preformed fibrin clot is utilized. For plasminogen detection, a plasminogen activator is also necessary as a reagent.

Magnetic particles

Materials that are diamagnetic experience no attraction to a magnet and may be repelled. Paramagnetism is a property imparted to a substance by the presence of unpaired electrons in an atom or molecules which causes the atom or molecule as a whole to act as a magnet. When placed into a magnetic field, these microscopic magnets align themslves with and are attracted toward the field. Ferromagnetic materials are paramagnetic substances which form "domains" containing very large numbers of paramagnetic atoms that are aligned in the same direction. The magnitude of interaction for ferromagnetic materials with a magnetic field is much greater than for other paramagnetic materials. Elemental iron, nickel, and cobalt are ferromagnetic materials. In the descriptions used throughout this patent application, the terms magnetic and paramagnetic are used interchangeably and include the ferromagnetic materials.

In the practice of the present invention, it is important that an appropriate paramagnetic particle be utilized. Appropriateness is a combination of inertness, magnetic properties and size. It is important that the particle be inert and not influence or affect the reaction.

To illustrate the importance of magnetic properties, magnetite, ($Fe_3O_4$) is more highly magnetic than $Fe_2O_3$ and makes a more suitable combination of dry reagent and magnetic particles. Magnetic latex particles (e.g. from Seradyn, Inc.) may also be used, but these are less strongly magnetic and make a poorer reagent for whole blood assays.

The size of the magnetic particles is important, as well. The particles should generally be less than 5 microns in diameter. Small particles (less than 1 micron) tend to work better than large particles. For example, 0.7 micron diameter particles work well. The particles should not settle out easily and be close to colloidal size for best results. Small size makes it easier for the particles to be dispersed in the reagent mixture, move in the magnetic field, and be monitored during the reaction.

| Reference No. | Magnetic Particle | Particle Size | Sizing Method | Comments |
|---|---|---|---|---|
| | | Summary of Magnetic Particle Data | | |
| 1 | $Fe_3O_4$ | 0.3 micron (average) | Fisher | Works extremely well |
| 2 | $Fe_3O_4$ | 0.77 micron (5 micron or less typically) | Fisher | Works extremely well More difficult to use-settles rapidly |
| 3 | $Fe_2O_3$ | −325 mesh 0.48 micron | (mesh size) Fisher | Works less well than $Fe_3O_4$ |
| 4 | Fe (Metal) | 2.68 micron (5 micron or less typically) | Fisher | Gives very large signal. May not be the best choice for "weak" clots and clot detection |
| 5 | Ni (Metal) | less than 0.8 micron | Fisher | More dense than $Fe_3O_4$. Settles rapidly. Works well. |
| 6 | Magnetic latex spheres | 1.75 micron diameter ±0.3–0.4 micron | Electron Microscopy | |
| 7 | Co (Metal) | 1.6 micron | — | Very dense. Some particle noise. Not as good as Ni |
| 8 | $CrO_2$ (Oxide) | Rod shaped particles 0.3 micron length >0.3 micron width | — | Works but not as well as $Fe_3O_4$ - could possibly work extremely well when optimized |
| 9 | Iron Oxides | 0.5–1.5 micron | Laser Light Scatter | Works well. |

Although it would seem at first blush that particles smaller than the wavelength of light will not work since such particles would not seem to be detectable, even with very small particles, the appropriate type of applied magnetic field results in aggregates which are easily visualized. For example, particles with an average diameter of 0.3 microns (by the Fisher Method) work well when illuminated with light from an infrared LED with peak emission at 875 nanometers (0.875 micron). The concentration of paramagnetic particles should typically be in a range of approximately 5 to 50 milligrams per milliliter of thromboplastin calcium reagent (or other reagent) used for preparing a dry reagent mixture, where this reagent is of sufficient concentration to be used for coagulation testing before the paramagnetic particles are added.

Particles which work well in the PT reagent are Ferrosoferric Oxide ($Fe_3O_4$). Nickel (Ni) particles work nearly as well as $Fe_3O_4$. Ferric Oxide ($Fe_2O_3$) works also. Iron Particles (Fe) are too strongly magnetic and do not work as well as $Fe_3O_4$ in detecting weak endpoints. Some magnetic (paramagnetic or super paramagnetic) particles which can be used in the novel invention described and will work for the applications described are actually used for an entirely different purpose. For example, the magnetic latex spheres are used generally in agglutination assays, typically involving antigen-antibody reactions. The other magnetic particles (Reference No. 9) are those which can be used for separations in antigen-antibody reactions.

The ferrosoferric oxide particle size which makes the best dry reagent is characterized by the manufacturer using the Fisher Method to determine average particle size. By this method, the average size is 0.3 microns. After the particles are suspended in thromboplastin (or thromboplastin-calcium) solution, the heavier particles are allowed to settle and only the lighter fraction is used to prepare the dry reagent. The mean particle size is therefore expected to be less than 0.3 microns.

Although there is a considerable concentration range over which the particles can be used to formulate dry reagent, the particles described above are typically added to the thromboplastin solution at 25 milligrams per milliliter. After removing the lighter fraction, approximately 80% of the total volume of particles remains behind and approximately 20% of the total volume of particles ends up in the dry reagent. Therefore, it is believed that approximately 5 milligrams of $Fe_3O_4$ per milliliter is employed in the actual dry reagent. In the dry reagent, a range of 0.5 to 50 milligrams per milliliter or even lower than 0.5 can be used.

Careful microscopic and micrometer measurements of the final dry (freeze dried) reagents reveal that the reagent exists on the reaction slide as a coating on upper and lower horizontal surfaces (cover and base). With a polyester cover, a polyester base, and a 0.007 inch thick spacer, the dry reagent coating on the lower surface (base) is generally less than 0.0015 inch thick and may be as thin as 0.0001 inch.

The dry reagent coating on the upper surface (cover) ranges from approximately 0.0005 inch to 0.0001 inch or even less. It is possible to produce a coating on the upper surface which is not measurable using this technique.

Often, essentially all of the iron oxide particles appear in the reagent at the lower surface. The particles reside in clusters as bumps or mountains (or shallow stalagmites or stalactites) when they appear in the reagent. Otherwise, the reagent forms a relatively uniform film which may seem waxy when scraped but dissolves instantly upon the addition of water or even high humidity. The film thickness dimensions include the additive contribution of stalagmites or stalactites.

It is important that a relatively flat surface be employed for the reagent-sample mixture undergoing analysis. A flat surface spreads out the mixture so that it may be more easily viewed and so that full advantage may be taken of the particle flicker phenomenon.

A slight well or depression can be used to advantage to locate the dry reagent and to capture the sample. In either case, however, the sample must be metered or pipetted accurately and precisely for best results. (A parallel plate configuration with capillary spacing configured to self meter the sample i.e. a reaction slide, is especially desirable, but not essential).

If the surface reflectivity is high, the background reflectance may be higher than for a less reflective surface. Either surface will work, but the low reflective surface will be better if the signals are weak.

Pretreatment of the surface with a suitable surface active agent prior to addition of the reagent may be desirable to spread the reagent by lowering contact angle with the surface. Surface active agents (i.e. surfactants or detergents) are otherwise not necessary. If a parallel plate configuration is to be used as a reagent containing element prior to drying the liquid reagent will flow in faster following surface pretreatment with 0.1% Triton X-100 (iscooctyl phenoxypolyelhoxyethanol) in distilled water.

Viewing a large area of the reaction volume is important to obtain the highly accurate results provided by the invention. If a very small area of the flattened reaction volume is viewed, the results are not very reproducible.

Results are not very reproducible, for example, if only 5 to 10 mm$^2$ of a 100 mm$^2$ projected total area of the flattened reaction volume is monitored. When a large, representative portion of the reaction is viewed, e.g., 20–50 percent of the total projected area,* the results are highly reproducible.

This is calculated for a reaction slide containing 25 microliters of reaction mixture and with a viewable reaction area (projected area) of approximately 100 square millimeters.

The range for total projected area has not been specifically studied. It is anticipated that the size of the projected area in relation to the volume of the reaction mixture is more important than the actual dimensions and magnitude of the projected area itself.

The projected area could be very small if the reaction volume is small but would ultimately be limited by ease of viewing and less total particles to view. If the projected area is very large it could be difficult to start the reaction simultaneously over the whole area. Viewing a large area is best, because data obtained by watching flicker patterns shows that the formation of polymerized fibrin rarely occurs uniformly over the area and at the exact same time.

The results are generally best if this viewing area is centered within the projected area of the reaction volume. The ultimate viewing area is to view the entire projected area of the reaction volume. Viewing the entire projected area may give marginally better results than viewing the central 40 to 50% of the same area.

To produce time varying orientation changes in the paramagnetic particles which appear as oscillating light and dark areas, a moving magnetic field is required. The field line orientation should cycle between being perpendicular to the plane of the flattened reaction volume and at a small angle (or parallel) to that plane. This angle can be any angle, but 0° and 90° for the particle orientation extremes gives the maximum signal. Theoretically, 80° and 85° could be used, but the signal would be small.

The object of using this moving magnetic field is to move the particles perpendicular to the solid support surface and alternatively flat against the surface in one full cycle of particle orientation change. The former orientation appears lighter when viewed from above, the latter orientation appears darker. The oscillation or alternating light intensity decays as the clot begins to form, presumably due to entrapment of some the particles in the fibrin polymer formed from the coagulation reaction (polymerization of fibrinogen).

The field strength should be sufficient to achieve observable orientation changes in the particles, even when whole blood samples are employed and to allow coagulation endpoints to be detected. The presence of whole blood makes it more difficult to obtain a good optical signal from the particle movement.

Magnetic flux density to obtain the flicker phenomenon should not be much less than about 5 gauss for plasma and approximately 10 gauss for whole blood and is quite effective at 20 to 600 gauss and can be even greater. Thus magnetic flux densities of from 5 to 600 gauss and more may be used.

Figure 5:
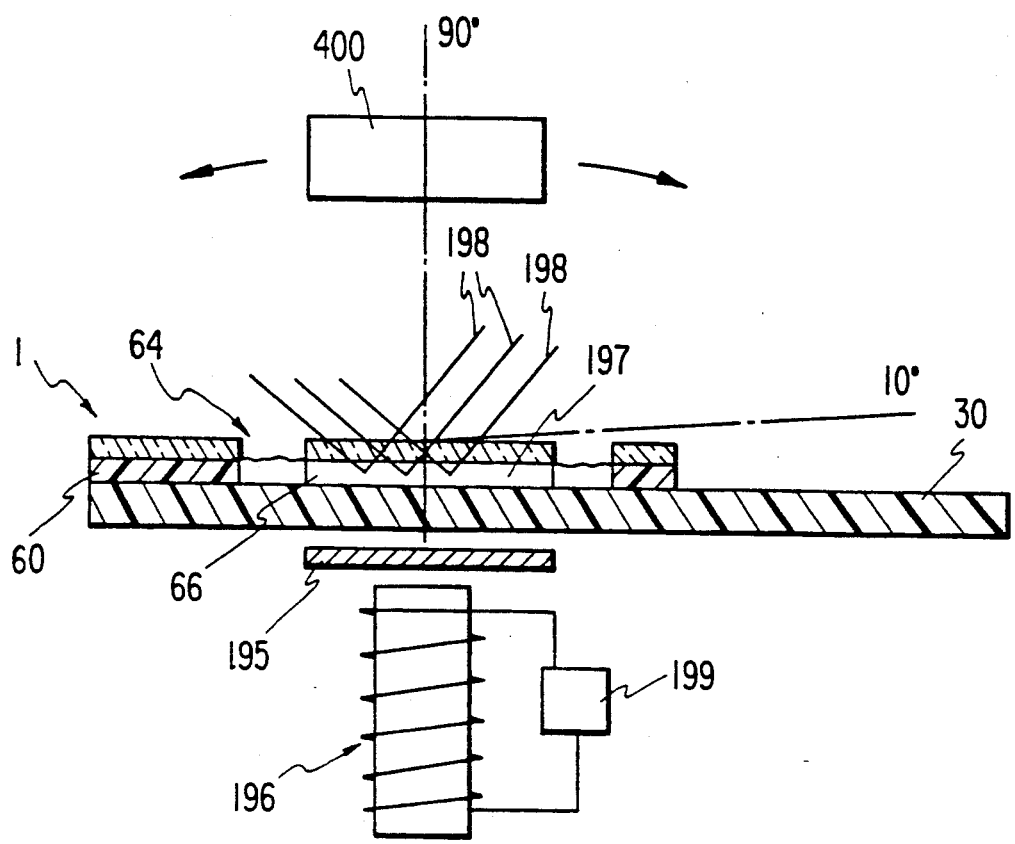
FIG. 5 is a longitudinal vertical cross-section of a reaction slide together with apparatus for using magnetic particles to measure a coagulation reaction.

Excellent assays were obtained with the arrangement shown in FIG. 5 where the bias magnet produced magnetic flux density peaks at +20 gauss and −20 gauss approximately every 0.030 inches at repeating intervals within the reaction volume. The electromagnetic flux density when current was turned on ranged from +60 to a peak of +90 gauss at the central part of the reaction volume situated above the center of the electromagnet core. Another electromagnet also gave excellent assay results with the same bias magnet. This electromagnet produced flux density values from +100 to a peak of +120 to +130 gauss.

The frequency of change of magnetic field orientation is important. If the frequency is less than 0.25 Hertz the endpoint precision will be poor, since an endpoint could only be read to the nearest 2° seconds. If the frequency is higher than approximately 4 Hertz, sensitivity in endpoint detection will be lower, and consequently the precision could also be poor. A frequency of approximately 1 Hertz is a good compromise. It allows an interval of 0.5 seconds between signal peaks and is associated with good precision.

Rotation of the field direction in the plane of the flattened reaction volume, such as could be achieved by rotating a permanent magnet beneath (or above) the surface upon which the reaction volume rests will not achieve highly reproducible endpoints with the dry reagent system employed. The rotating or spinning magnet approach for example is used by Adler (U.S. Pat. Nos. 3,650,698 and U.S. Pat. No. Re. 27,866) produces a whirlpool-like effect with paramagnetic particles, moving the particles closer to the center. The "whirlpool" ceases all or part of its motion at the moment of clot formation. This effect is not well suited to solid phase reagents and has problems with reproducibility when used with our dry reagents. Repeated attempts to obtain endpoints with dry reagents resulted in poor endpoint reproducibility, using the rotating magnet methods. In addition, sometimes an endpoint would be obtained, as indicated by a sudden clumping of particles, but the clump would still spin in the rotating field making detection even more uncertain.

The time varying magnetic field may be achieved in a variety of ways. If, for example, a reaction volume is placed on a surface, the following configurations are possible:

A. A permanent magnet pole (or poles) or an energized electromagnet situated beneath (or above) the surface with its field lines passing through the surface is moved back and forth along a straight line parallel to the surface. Upon addition of a liquid sample the mixture of dry reagent and magnetic particles is then observed to "flicker" with each pass of the magnet. In the absence of a liquid sample, the magnetic particles will not be free to move within the dry reagent, and essentially no flicker, signal will be observed. This is illustrated in FIG. 7(a and b). FIGS. 7a and b provide views of substantially flat reaction surface 500 charged with a combination of reagent and magnetic particles 501. A permanent magnet 503 is displaced in direction 502.

B. An electromagnet, preferably with a ferromagnetic core, is situated beneath (or above) the surface such that when energized, the magnet produces field lines which pass through the surface. When the magnet is turned on and off, the mixture of dry reagent and magnetic particles (with sample added) is observed to flicker. This approach as shown in FIG. 8 is, however, less dramatic and therefore produces a lower signal level than the same magnet moved back and forth in a straight line.

C. A permanent magnet or electromagnet situated beneath or above the surface with its field lines passing through the surface is moved parallel to the surface in a circular, elliptical, or similar repeating orbit. This causes a flickering pattern to result. This is illustrated in FIG. 9(a and b). FIGS. 9a and b illustrate the motion 504 of permanent magnet 503 with respect to the substantially flat surface 500.

D. A flat thin bias magnet (e.g. permanent strip or tape magnet with multiple poles arranged in a repeating stripe pattern along the surface of the magnet) is placed directly beneath the surface and an electromagnet placed beneath it is cyclically energized. This is shown in FIG. 5. The dry reagent simply dissolves, when sample is added, and releases the magnetic particles. The magnetic particles orient themselves in microscopic clusters or stacks as in cases A, B, C, E, and F. The particles orient themselves along the field lines of the bias magnet (flat against the surface) and stand perpendicular to the surface (or at a steep angle) when the electromagnet is energized. This produces a characteristic flicker pattern which is somewhat different from that produced in A, B, or C, in that the particles tend to concentrate along the bias magnet field lines in addition to flickering.

E. A permanent bias magnet (flat cylindrical or other flat geometric shape) located beneath the surface where the magnetic particles are situated and an electromagnet with poles facing each other such that the field lines run parallel to the surface with the magnetic particles (when the magnet is energized) and perpendicular to the direction of the field lines emerging from the permanent magnet. This is shown in FIGS. 6(a and b). FIGS. 6a and b illustrate a stationary permanent magnet 503 situated in proximity to substantially flat surface 500 and oscillating magnetic field means 505.

F. The most dramatic flicker is achieved in A and C. B, D and E require no moving parts, and of the three, B is least effective. Other combinations of magnets and geometries may be used, as long as the underlying principles of orientation to produce a flicker pattern are followed. For example, a permanent magnet pole may be moved up and down along a vertical line where at the top of its trajectory, the magnetic pole is in close proximity with the bottom of the surface upon which the reaction mixture is situated. At the bottom is its trajectory, it is moved far enough that its magnetic field lines no longer cross through the surface to effect particle movement.

PARTICLE MOVEMENT MONITORING

A light source can be used to monitor the movement of the magnetic particles. This light source should have sufficient brightness to produce a good optical signal; a reflected and/or scattered light signal. Visual viewing in a well lit room or in a sun lit room is satisfactory but not suitable for an automated system. The wavelength is not as critical, as long as it is reflected or scattered by the paramagnetic particles, above and beyond background scatter.

An ultra-bright LED such as a Hewlett Packard HLMP-3750 Gallium Arsenide Phosphide on Gallium Phosphide LED, which emits at a peak wavelength of 635 nanometers, works well. An even better choice is an infrared LED, such as a TRW OP290A Gallium Aluminum Arsenide LED which emits at a peak wavelength of 875 nanometers.

The light source should be reasonably stable whether operated in D.C. or pulsating modes. Stability is necessary, so that measurement of "light" and "dark" peak signals during the particle orientation cycles can be carried out precisely, enabling a decrease in peak to peak distance as a result of the onset of clotting to be readily distinguishable.

It is important, also, that the light be measured at an appropriate angle. If the surface upon which the reaction mixture is situated is transparent, it is possible to measure the flicker effect by transmission through the reaction mixture. In this case, the light source and detector would be situated in a line of sight configuration and the reaction mixture situated between them. This approach, however, does not leave much room for magnets or temperature control apparatus.

A more practical arrangement is to measure the flicker effect by reflectance or scatter of light from the reaction mixture as illustrated in FIG. 5. In this arrangement, the light source is used to illuminate the reaction mixture to create an angle of incidence (from the normal to the surface) which is different from the angle at which the detector views the reaction mixture. This is to avoid glare which occurs at the angle of reflection (equal to the angle of incidence). A typical working scheme is to place the detector above the reaction mixture and illuminate the reaction mixture with light projected from an angle of approximately 45 degrees to the normal.

The intensity of light from an approximate point source falls off with the square of the distance. A conventional light emitting diode produces a cone of light. The most intense portion of this cone is desired for illumination of the reaction mixture. This intense "cone within a cone" should ideally illuminate neither more nor less than the entire reaction volume. Moving the LED further away from the reaction volume will tend to spread the cone and reduce average light intensity at the reaction volume. Moving the LED closer will concentrate the cone and reduce light intensity at the periphery of the reaction volume thereby lowering available signal from this area.

For monitoring the flicker phenomenon produced by the reagent, the use of a signal from the photodetector which is A.C. coupled to an amplifier, as opposed to D.C. coupled, produces the best results. From the A.C. coupled amplified signal, the moment at which a large change occurs determines the time of entry of sample into the reagent containing area, and this identifies the time at which the assay had begun. Prior to this event, the magnetic field is varying at a preset frequency (e.g. 1 or 2 Hz.)

Figure 3:
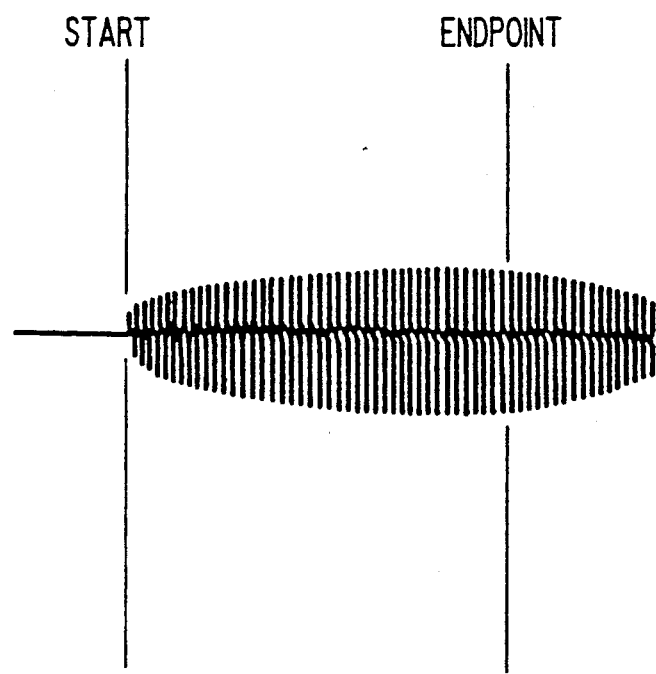
FIG. 3 illustrates a tracing obtained by monitoring the optical signal of oscillation between orientation states of the magnetic particles.

After the initiation signal for the assay, the next signal which is observed is an oscillation due to the flicker phenomenon. This A.C. coupled signal starts off small and then within a few seconds grows to a height which remains approximately constant or grows only slightly thereafter but does not diminish until a clot begins to form. See FIG. 3.

Figure 4:
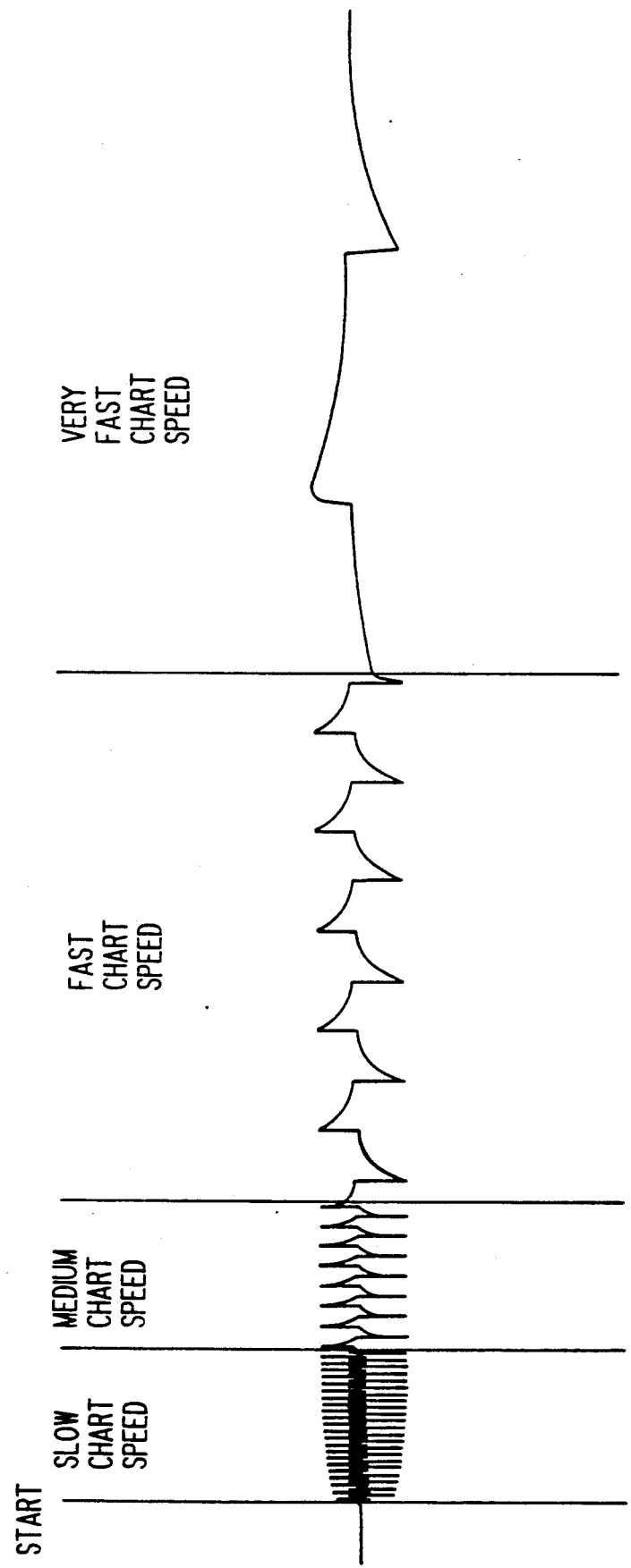
FIG. 4 illustrates a time expanded view of the tracing illustrated in FIG. 3 above.

The diminution of this signal is then used to determine the endpoint or moment of clot formation. The strength of the A.C. signal is typically measured by taking readings immediately after one peak has occurred (e.g. a positive peak). The difference between each peak (positive or negative) and the next peak is thus determined. FIG. 4 shows a time expanded view of this.

These difference values are then monitored to see when the difference value begins to decrease. This corresponds to the onset of clotting. What happens next is a more rapid decrease of the difference value as the clot more fully forms.

Threshold criteria are applied to the signal to determine the start point and endpoint for the assay. To determine the start point, a signal level is required which is greater than that which would be produced by vibration or by changes in ambient room lighting. Changes in the ambient light, although practically isolated from the photometric detector could have a small effect due to leakage through seams or vents in the apparatus. The start point threshold is set above this backgound level where there is still very considerable signal due to sample entry light scatter and absorption (reflectance).

To determine the endpoint, a decay of peak to peak height of between 2 and 20 percent which persists for at least 10 seconds and preferably 15 to 30 seconds is identified. For example, if a decay in peak height of 8 percent and a time duration of 15 seconds is selected, then satisfying both of these criteria determines that the last peak immediately preceding the decay is the nearest identifiable moment to the onset of clot formation. That is, if during a 15 second interval the peak heights diminished by 8% and did not increase again during the interval, than an endpoint has been achieved.

Selecting a threshold of 2% or 5% would be a more sensitive criteria than 15 or 10% for detection of weak endpoints. Similarly, setting a window of 30 seconds would be a more sensitive criteria than 10 seconds. For example, peak heights associated with a very weak clot might not drop 8 percent in 10 seconds but might in 15 seconds.

Scale factors are also required to translate the observed dry chemistry prothrombin times to those which correspond to values typically obtained in clinical laboratories using liquid reagents. For example, a normal prothrombin time of 12 seconds using liquid reagents may be observed as 24 seconds with the dry reagent system. An abnormal prothrombin time of 25 seconds with liquid reagent may be observed as 50 seconds with the dry reagent system.

Thus, a scale factor or equation of a straight line which correlates both types of assays is used to express the dry chemistry result in terms that are customary in today's laboratories which employ liquid reagents. More than one scale factor may be necessary. Although citrated plasma and citrated whole blood scale factors (or straight line equations) have been observed to be essentially identical for a given batch of reagent, the scale factor for blood without an anticoagulant is typically different. It is therefore important to identify the sample and then select the appropriate scale factor.

The scale factor is obtained by comparison of PT results using the sample type (for which the factor needs to be developed) plotted against the results of the same blood samples run as plasma samples on a conventional analyzer. The equation or table which compares the two sets of values is then obtained and used as a scale factor. This was never a problem before, because existing assay technology did not offer multiple sample options. The scale factor selection can be automatic if all scale factor information is encoded on the reagent containing element and subsequently transferred to the instrument memory.

A silicon photodiode is an ideal photodetector for monitoring the reaction in this application. It has fast response time and good spectral sensitivity at longer visible and infrared wavelengths where bright, inexpensive, and highly reliable light sources (LED's) have peak emission. A photodiode also has a proportional electrical response to light detected. The photodiode should be isolated from ambient light. This may be achieved by physical isolation or through the use of a filter (e.g. to screen out all radiation except for infrared at the same wavelengths as the peak emission of the LED) or by a combination of both approaches.

The detector may be positioned such that it faces the surface on which the reagent-sample mixture is situated. The detector semiconductive element will usually capture the most light if positioned parallel to the plane of this illuminated surface. It is important that the detector be placed at such an angle that glare reflected by the reagent-sample mixture (or, more likely, the surface of a transparent cover, e.g. of a reaction slide) from the source does not impinge on the detector element surface. This glare will increase noise. The closer the photodetector element is placed to the surface containing the reaction mixture, the more light will be captured and the higher the signal to noise ratio.

Figure 2:
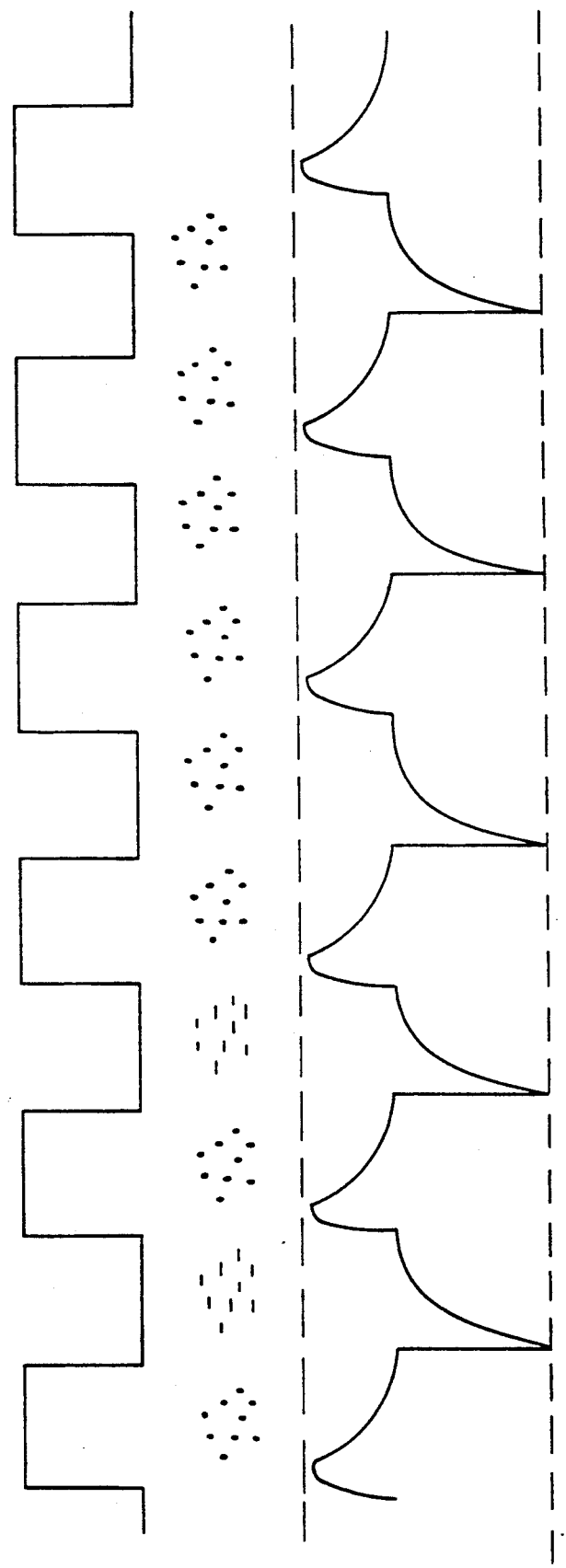
FIG. 2 illustrates the relationship between (A) the electromagnet waveform, (B) the orientation of the combination of magnetic particles and dry reagent after a sample is added, and (C) the AC coupled electrical signal from the photodetector which reflects magnetic particle oscillation when the assay is performed.

The photodetector may be placed as close to the slide as is practical without having stray light from the source produce artifacts. This could be as close as 0.2 inches or possibly less. The photodetector may be moved further back (to 1 inch or more from the surface) but eventually the signal will begin to fall off appreciably due to inverse square law attenuation. Similarly, the larger the photoactive element of the detector, the greater the light captured and the larger the signal before amplification. A Hammamatsu S2386-8K photodiode works well for this application, but many other similar detectors may be utilized.

a. Threshold for start of reaction: The start point of the PT assay is taken to be coincident with entry of the liquid sample into the volume or area occupied by the dry reagent. In the current optical signal detection circuitry, a photodiode (Hammamatsu S2386-8k) is employed. A photodiode amplifier supplies a gain of 499,000. An AC coupled amplifier supplies a gain of 10. A selectable gain amplifier supplies a gain of from 1 to 128. Application of sample (or start time) is detected by looking for an absolute change of the AC coupled signal (amplified 16x) of more than 3.9% of maximum (5 volts) or greater than (or equal to) 0.195 volts.

b. Establishment of Flicker Phenomenon: At a fixed time after the sample is detected and the assay started, the software selects the appropriate AC coupled signal gain. This gain sets the largest allowable signal which will not grow sufficiently thereafter to saturate the amplifier. It is known from experimental data that the flicker effect for all PT signals has reached at least 50% of the maximum signal size after approximately 7 seconds.

c. Flicker Signal and Endpoint: FIG. 2 shows a fully established flicker signal. In this example, a permanent magnet is used as a bias to achieve maximal horizontal particle orientation. An electromagnet is switched on and off to achieve maximal vertical orientation. Both magnets are, in this example, located below the surface on which the particles are situated. The Upper Signal (A) corresponds to the square wave driving current to the magnet. The first square wave plateau is for the current turned on. The middle signal (B) is a series of snap shot views taken from above of the particles (actually clusters or aggregates of particles). The first is with the electromagnet energized and shows maximal vertical orientation. The second is with the electromagnet deenergized and shows maximal horizontal orientation, and so forth. The pivot point for each microscopic "stack" of particles is at the base or lower surface. The particles stacks, as viewed under the microscope at 100× magnification, appear "rooted" to this surface and sway to and fro with the magnetic field line orientation change. This imparts alternating (lighter and darker) reflected or scattered light creating a "flicker" effect.

As polymerization of fibrin proceeds, the movement of the particle stacks appears restricted, in that the maximal vertical and/or horizontal positions are no longer fully achieved. The flicker is thus less pronounced. This signals the onset of clot formation.

During this stage, when viewed microscopically, the particles soon appear to be attached or stuck to a barely visible, barely discernable space filling substance. As the stacks now move, the substance appears to move with them. Some of the stacks are distorted or curved (like curved or bent trees) and fluctuate in decreasing extremes of orientation as the clotting process proceeds. The particles are definitely entrapped in the clot at this stage and apparently cannot be removed without destroying the clot.

The lower signal (C) is the AC coupled optical signal resulting from the particle flicker phenomenon. The decrease in peak to peak distance signalizes the onset of clot formation.

d. Additional Information Provided From Signal: By shifting the threshold for clot detection, "weaker" clots can be differentiated from stronger clots. Weaker clots will show more gradual peak to peak decreases in signal strength than strong clots. Control Plasma Level III from Ortho Diagnostics, Inc., for example, shows consistently weaker clots than Pacific Hemostasis, Inc. Control Plasma, Level III. The physicochemical, biochemical or clinical significance of differences in clot strength is not known at this time. The ability to differentiate between different types (or strengths) of clots may have diagnostic value.

The "strength" of the clot may actually be a measure of the mass of the clot or total protein involved in its formation. If fibrinogen concentration is significantly lowered in a sample which is assayed for prothrombin time, the resultant PT value may be unchanged or may become slightly elevated from normal, but the effect of clot "strength" is more readily observed. This effect may be quantified by measuring the maximum peak to peak amplitude (A) just before the onset of the endpoint and peak to peak amplitude (B) a set time after the endpoint onset. The greater the ratio (A-B)/A the "stronger" or more massive the clot.

e. Automatic Entry of Scale Factors: Converting the resulting assay values obtained with the dry reagent to values which correspond to laboratory results with liquid reagents is achieved using a scale factor or conversion factor. This factor is first developed by plotting dry reagent values against clinical laboratory values for the same samples, over the clinical range of PT values. An equation (e.g. in the form of a straight line: $y = mx + b$) may now be used to convert any dry chemistry assay result to the expected laboratory value. Four advantages result: 1) An equation may be set up for each different type of sample, i.e. a sample taken without anticoagulant or a sample obtained with citrate anticoagulant. 2) The equations might possibly be fine tuned to allow correspondence of the dry chemistry results to a particular wet chemistry thromboplastin reagent/instrument combination. This could become an important advantage, since it could allow decentralized assay results to correspond closely to a particular reference geographical region. Standardization has been an ongoing problem for PT measurements. 3) The scale factor equations may be supplied along with the reagent slides and fed automatically to the instrument's microprocessor to achieve the desired results. The information may be magnetically or optically encoded. 4) Possible differences between reagent lots may be automatically compensated for.

A typical scale factor equation might read:

$$y = 0.4x + 6$$

where:
y = PT adjusted to laboratory values
x = actual dry reagent PT

The coagulation assay of the invention can be advantageously performed in a reaction slide comprising a channel structure defining a sample well and a reaction volume in communication with each other. When using this reaction slide, the reaction volume is charged with a measured amount of a combination of (i) magnetic particles and (ii) at least one dry reagent. The channel structure possesses a geometry which causes a liquid sample placed into the sample well to be drawn into and filling the reaction volume via capillary action, wherein after the reaction volume is filled, the liquid sample remains stationary. This element is fully described in U.S. Patent application Ser. No. 07/033,817, filed Apr. 3, 1987, now U.S. Pat. No. 4,849,340, which is hereby incorporated by reference.

In the assembly of this element, the reaction slide is made up of a base, an overlay, and a cover. The base comprises a major surface. The overlay is situated on the base. The cover is situated on the overlay, opposite the base. The overlay comprises the channel structure defining a sample well and a reaction space in communication with each other. The cover comprises a means for adding a sample to be analyzed to the sample well. The assay is performed by monitoring a reaction of the sample in the reaction volume with the sample as a whole being stationary during essentially all of the assay.

Figure 13:
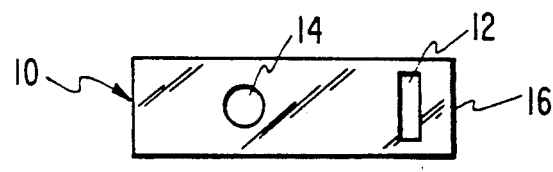
FIG. 13 is a top view of a cover of a first embodiment of a reaction slide according to the invention.
Figure 14:
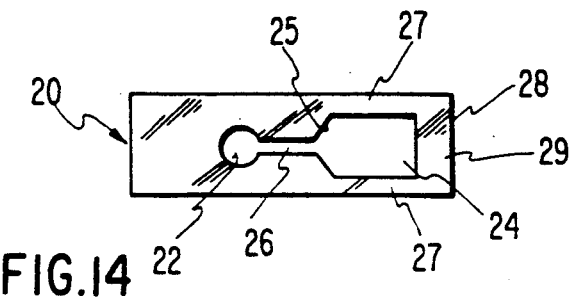
FIG. 14 is a top view of an overlay of a reaction slide according to the first embodiment.
Figure 15:
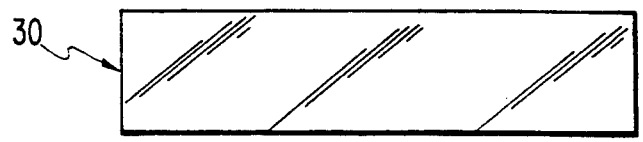
FIG. 15 is a top view of a base of a reaction slide according to the first embodiment.

Shown in FIG. 13 is a top view of a cover 10 of a first embodiment of a reaction slide according to the current invention. Shown in FIG. 14 is a top view of an overlay 20 of the first embodiment. Shown in FIG. 15 is a top view of a base 30 of the first embodiment. FIG. 16 is an exploded view showing the relative positions of the cover 10, overlay 20 and base 30. Although FIG. 16 illustrates the reaction slide as being a three component assembly, assemblies requiring fewer components are possible.

Instead of a three component assembly where the reaction volume is formed from material which is removed from the second or middle component prior to assembly, a two component structure may be utilized. In the case of a two component structure of assembly, the reaction volume would be formed by embossing the upper, lower, or both components.* The components could then be joined by utilizing a pressure sensitive adhesive applied to selected areas of one or both of the components, by ultrasonic welding or other types of heat sealing processes, by using solvent bonding, or through the use of specialty adhesives (e.g. U.V. curable liquid adhesive), etc.

*As an alternative to embossing, which is a pressure forming process, thermoforming techniques can be utilized to create the depressed or raised regions of base or cover material.

Figure 39A:
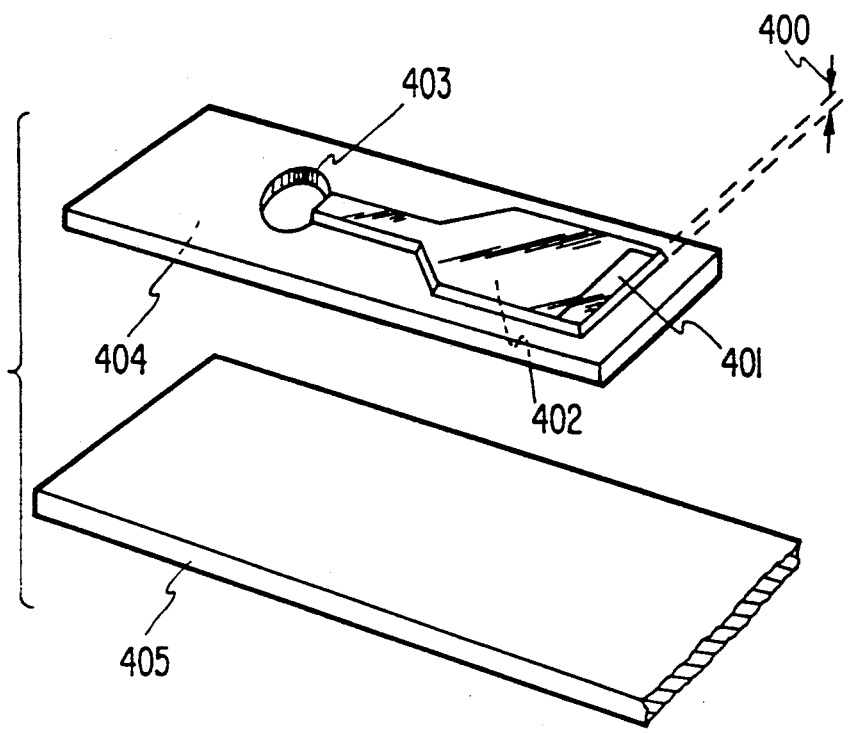
FIGS. 39 (a and b) and 40 (a and b) illustrate varied two-component assemblies of the reaction slide.
Figure 39B:
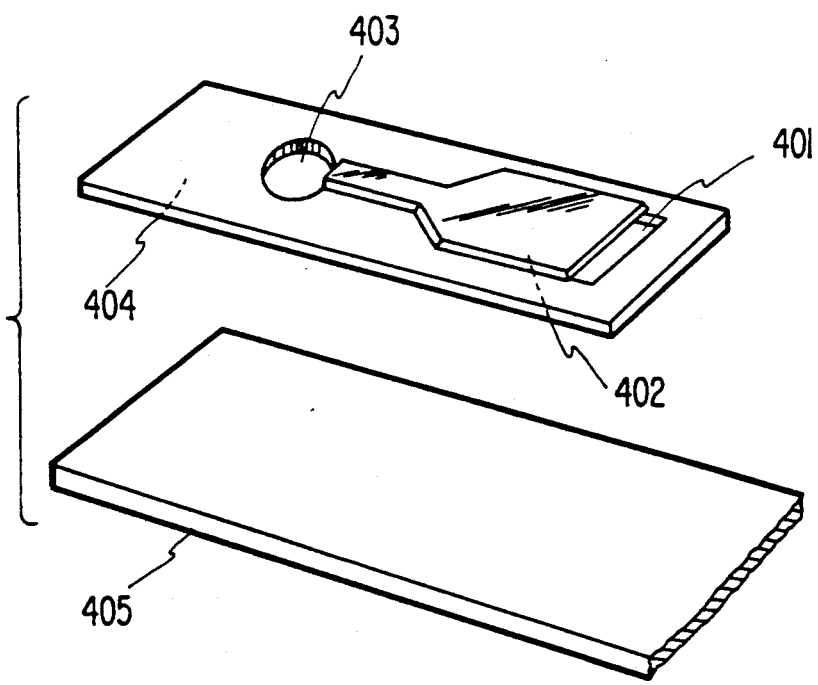

In FIGS. 39a and 39b two possible embossed cover versions are illustrated. In 39a, the sample well hole 403, conduit, reaction volume 402, and air vent hole 401 are included in the embossed, raised portion of the cover 404. After embossing the cover, the sample well hole and air vent hole are punched out or otherwise created. Adhesive may now be applied to the original bottom surface of the cover (but not to the roof of the cavity) so that the cover may be joined to the base. Alternatively, as shown in FIG. 39b the cover may have an embossed region which excludes the sample well and air vent. In this case, the sample well and air vent holes may be created after, but preferably before, embossing. Adhesive may be applied to the original bottom surface of the cover, as in the previous case, to join the cover to the base 405 to fabricate the reaction slide. In addition to examples shown in FIGS. 39a and 39b, other combinations are possible, for example: to include the sample well region in the embossed area but not to include the air vent slot; or to include the air vent slot region but not the sample well.

Figure 40A:
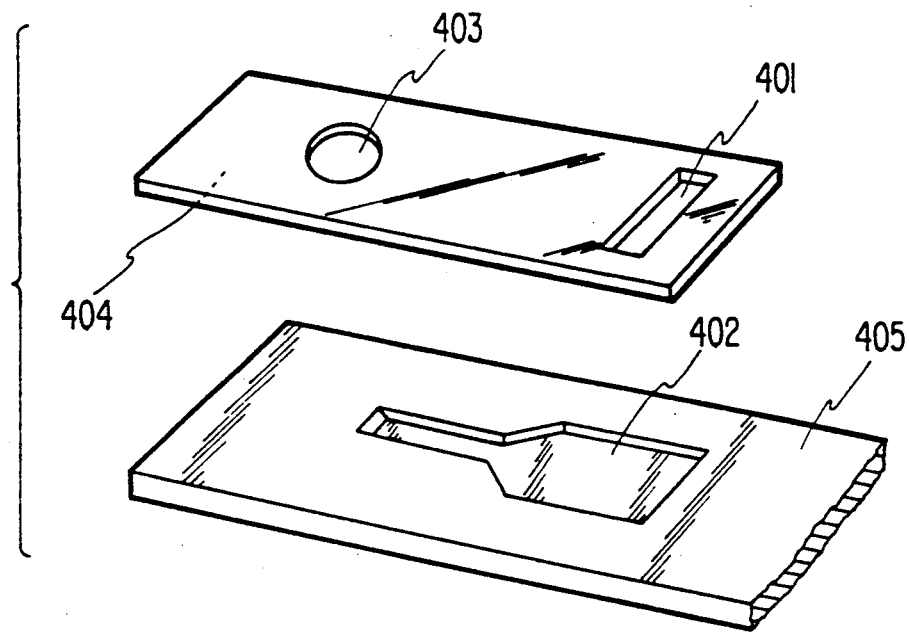
Figure 40B:
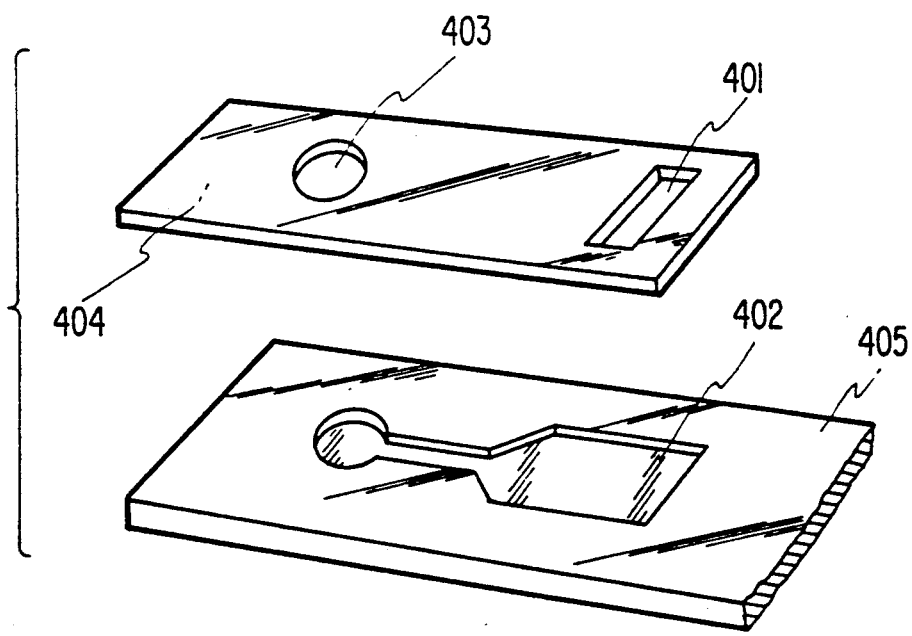

FIGS. 40a and 40b show two possible embossed base (405) versions. In 40a, the conduit, reaction volume 402, and air vent regions are included in the embossed section of the base. The sample well hole 403 and air vent hole 401 are situated in the cover piece. The bottom surface of the cover may be coated with adhesive to allow it to be joined to the base. Alternatively, as shown in 40b, the embossed area may contain sample well, conduit, reaction volume, and air vent slot. Other variations are possible, as well.

In addition to embossing or related processes, the component pieces could also be fabricated by injection molding of each piece. That is, the cover with preformed air vent and sample well holes could be injection molded as one piece with or without an appropriate cavity structure, and the base with or without an appropriate cavity structure could be separately injection molded. The molded pieces could be provided with indexing holes and pegs for automated assembly and could even be joined by a hinge at the edge to allow a rapid assembly procedure to be utilized. Similarly, embossed cover and base sections could be formed from continuous reels of film polymeric material, machine assembled, and cut into individual slides.

Reaction slides formed from two component pieces would generally be most useful for making optical (or other) measurements which do not require sandwiched layer waveguide properties. Internal waveguides are most appropriately formed in a reaction slide by using three layers (or more) where the middle layer acts as does an optical fiber core and the outer layers act as cladding. This does not, however, limit the use of external waveguides for introducing light into the reaction slide and for guiding light out of the reaction slide to allow photometric analysis to be achieved.

Figure 17:
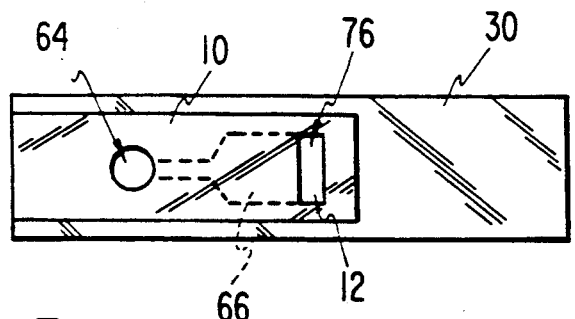
FIG. 17 is a top view of the elements of FIGS. 13-15, when assembled.

FIG. 17 is a top view of the cover 10, overlay 20 and base 30, when assembled.

FIGS. 18 a, b and c are longitudinal vertical cross-sections of other embodiments of a reaction slide 1 according to the current invention. The cover 10, overlay 20 and base 30 are sectioned along line VI—VI of FIG. 17. As will be described more fully below, the reaction slide 1 contains certain elements in addition to those shown in FIGS. 13-16.

Now referring generally to FIGS. 13-18, the cover 10 comprises a thin glass or polymeric sheet, typically transparent, having formed therein a sample receiving opening 14 and an elongate opening 12 proximate a distal end 16 of the cover.

The overlay 20 comprises a thin glass or polymeric sheet, typically transparent, having formed therein a cut-out, the cut-out having a geometry as shown to form a sample receiving opening 22, a reaction space 24 and a conduit 26 communicating the reaction space and the sample receiving opening. (The reaction space 24 becomes a reaction volume upon assembly of the cover, overlay and base.) Advantageously, tapering walls 25 form a transition between the conduit 26 and reaction space 24. The distal end 28 of the overlay is closed as shown at 29.

The base 30 comprises a sheet of glass or polymeric material, typically transparent and typically somewhat thicker than either the cover 10 or overlay 20. Conduit 26 is important in that it connects the sample well to the reaction volume; however, its significance derives from the fact that it is the bridge between the exterior and interior of the instrument, allowing sample to flow from one domain to the other without having to open a door or hatch in the instrument. If the conduit is too short, it is difficult to properly place the sample without touching the instrument wall. If too wide, sample is wasted; if too thin, or too narrow, flow could become obstructed.

In a preferred embodiment of this invention, conduit 26 is charged with a material which will cause a preliminary reaction in the sample to take place or otherwise treating the sample, permitting the introduction of a modified sample into reaction space 24.

The cover 10 and base 30 are separated by a spacer 60, the spacer 60 being made up of the overlay 20 sandwiched between two adhesive layers 62 which respectively join the overlay 20 to the cover 10 and the overlay 20 to the base 30. Each of the adhesive layers 62 has the same shape as the overlay 20. That is, each of the adhesive layers is formed with an opening having a shape corresponding to the sample receiving opening 22, the reaction space 24 and the conduit 26 of the overlay 20. Accordingly, there are formed in the reaction slide a sample well 64, a reaction volume 66, a conduit communicating the reaction volume 66 and the sample well 64, and a vent 76 formed by the opening 12 in the cover 10 communicating the reaction volume 66 with the environment of the slide.

Figure 18A:
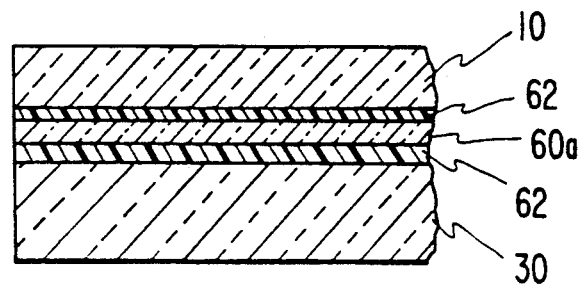
FIGS. 18 a, b and c illustrate elevational cross-sections of a fragment of a reaction slide according to the invention, illustrating a modification in which the reaction slide comprises a spacer that includes overlays.

In FIG. 18a, a film layer 60a is sandwiched between the two adhesive layers 62. In FIG. 18c a single thicker adhesive 62 layer is used.

The bottom surface of the cover 10, facing the base 30, is spaced from the top surface of the base 30 by a distance that is sufficiently small to cause a sample placed in sample well 64 to be drawn into the reaction volume 66 by capillary action. Such action is made possible by the presence of the vent 76. This vent also provides an air interface which defines one boundary of the reaction volume when filled with liquid, thus assisting in the self metering function of the reaction slide.

As shown in FIGS. 13-15, the length (left to right in the drawing) of the cover 10 is the same as that of the overlay 20, and the width (top to bottom in the drawing) of the cover 10 and overlay 20 are the same and are (typically) less than that of the base 30.

Observations and measurements of chemical reactions occurring within the reaction volume 66 may be made by a number of methods, as described more fully below. At present, optical methods are preferred, but the choice of method will depend upon the assay being performed.

Shown in FIG. 16 are a number of paths that light may typically follow for making such measurements and observations. These paths may be used alone or in combination.

In light path 40, light is introduced through a side of the overlay 20 and passes initially through a portion of the overlay disposed between the closed end 29 and tapering wall 25. This portion of the overlay and its opposite corresponding portion will be referred to as internal waveguides 27. Thereafter, the light passes through the reaction volume 66 and out through the opposite waveguide 27. As illustrated schematically, light passing in this direction through the waveguides is internally reflected off the top and bottom surfaces of the overlay 20. Light path 40 is useful in making measurements based on the transmission or absorbance of light by the fluid within the reaction volume 66, in which case there is measured the ratio of light intensity before and after passing through the sample in the absence of scattering or excluding scattering. The Beer-Lambert Law describes the phenomenon. Standard detectors are employed in a line of sight configuration with the light source.

Light path 41 illustrates a measurement that may be made based upon light scattering in which light is first introduced transversly through an internal waveguide 27, enters the reaction volume 66, is then scattered by the sample, a portion of the scattered light proceeding downwardly through the base 30 and then leaving the reaction slide. Light scattering measurements or nephelometry measures light which is not irreversibly absorbed by the sample and emerges at various angles, the spatial/intensity distribution being dependent upon particle size, shape and wavelength of the excitation energy. Rayleigh and Mie theories are useful models.

Standard detectors are employed. Examples are photocells or photomultipliers, the latter being employed at very low light levels. Excitation source wavelength may be fixed at a particular value. The detector is typically set at a predetermined angle from the direction of excitation.

Light paths 42 and 43 respectively show light entering laterally through the sides of the cover 10 and base 30, experiencing total internal reflection as it passes directly above and beneath the reaction volume, respectively, and exiting through the opposite edge of the cover or base. As is explained more fully in U.S. Patent application Ser. No. 07/033,817, filed Apr. 3, 1987, now U.S. Pat. No. 4,849,340, which is hereby incorporated by reference, such light paths may be employed for detecting fluorescence using an evanescent wave measurement.

Other light paths are possible, including vertical paths passing through the cover, reaction volume and base and light paths making use of reflectance off a sample in the reaction volume, according to which light may both enter and leave the reaction volume by way of the cover 10 or base 30.

It will typically be desirable to exclude stray light from entering the reaction slide. For this purpose, any external surface of the reaction slide which is not to be used for the transmission of light may desirably be painted with an opaque paint. The choice of surfaces to be so painted will be governed by the assay to be performed and the elected methods of measurement. When any of the components 10, 20 or 30 will not be used for the transmission of light, that component may be made of a material which is itself opaque, such as metal.

When using light paths such as 40 and 41 in FIGURE 16, it becomes important to transmit as much light as possible through one or both of the internal waveguides 27, keeping the losses as low as possible. It has been found that the presence of the adhesive layers 62 can cause the spacer 60 to perform like an optical fiber, the waveguides 27 corresponding to a core of an optical fiber and the adhesive layers 62 corresponding to cladding.

Figure 27:
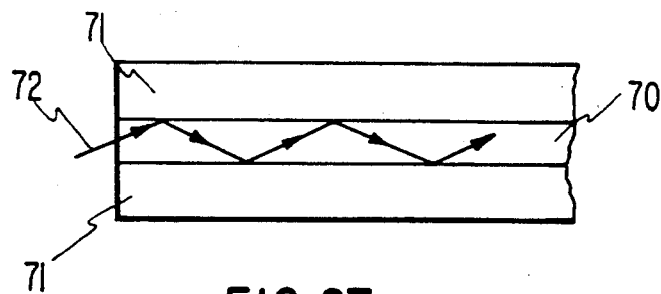
FIG. 27 schematically illustrates a vertical cross-section of a modification of a reaction slide that does not employ adhesive layers, the figure illustrating light entering that embodiment.

Refractive index mismatch between the waveguide 27 and the adhesive layers 62 produces total internal reflection of light striking the interface at angles greater than the critical angle. By way of example, reference is made to FIG. 27, wherein there are shown core 70, cladding 71 surrounding the core 70, and incident light ray 72 striking and passing through the core 70. The core 70 may correspond to the internal waveguide 27 of the overlay, and the cladding 71 may correspond to the adhesive layers 62. If, for example, the core material 70 has a refractive index $n_1$ of 1.62 and the cladding 71 has a refractive index $n_2$ of 1.52, the sine of the critical angle is $n_2/n_1$, or $1.521/1.62 = 0.938$. The critical angle is then 69.8 degrees.

Figure 19:
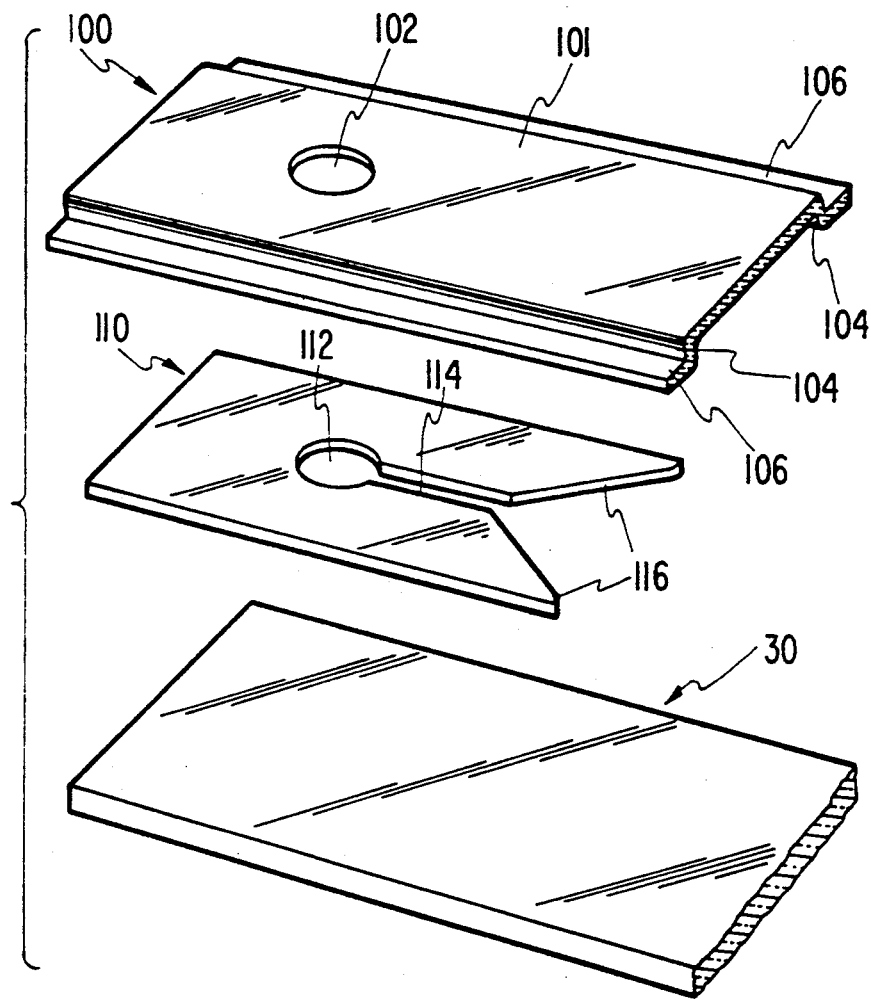
FIG. 19 is an exploded view of a different embodiment of the reaction slide of the present invention.
Figure 20:
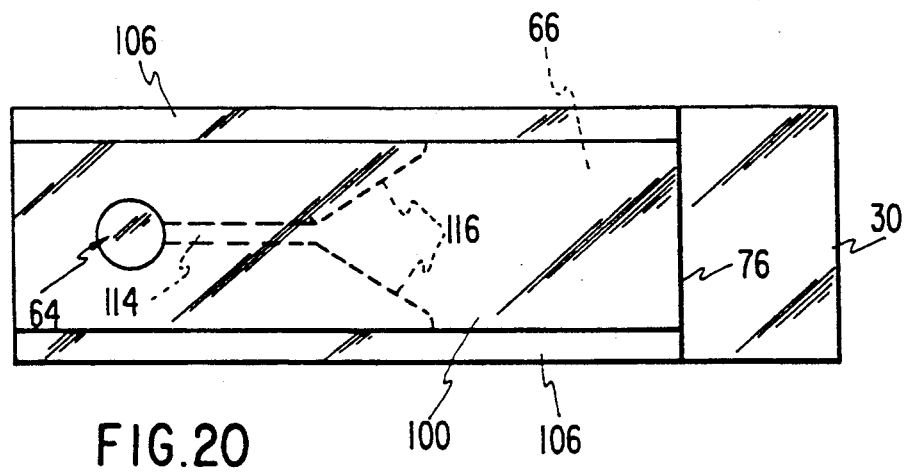
FIG. 20 is a top view of the different embodiment of FIG. 19.

FIG. 19 provides an exploded view of a different embodiment of the reaction slide of this invention. A top view of this embodiment is shown in FIG. 20, with selected vertical transverse cross-sections being shown in FIGS. 21 and 22.

There is shown a base 30 on which is fixed an insert 110 and insert cover 100. Insert cover 100 is generally formed by a major planar segment 101 having lateral sides bent downwardly outward to form walls 104 and then laterally to form tabs 106. The tabs 106 are bonded to the base 30 with the insert 110 being disposed between the planar segment 101 of the insert cover 100 and the base 30, the height of the walls 104 generally corresponding to the height of the insert 110.

Insert 110 includes a sample receiving opening 112 communicating with a conduit 114 which ends in outwardly tapering walls 116. As the length of the insert 110 is substantially less than the length of the insert cover 100, a reaction volume 66 is formed to the right of the insert as shown in FIG. 20.

Thus, it may be seen that the walls 104 in the area of the reaction volume 66 serve the functions of the internal waveguides of the previous embodiments, and for this purpose at least those portions of the walls 104 that are disposed in the vicinity of the reaction volume 66 are made of a transparent material.

Although the insert 110 may be bonded to the base 30, variations are possible. For example, the insert and base may be formed as one piece, molded or machined to the appropriate shape and channel structure.

As will be described in more detail below, an assembled reaction slide according to the various embodiments will typically contain one or more reagents specifically selected for their utility in performing any of the many assays that may be performed using reaction slides according to the current invention. For example, liquid reagent may be placed in the reaction volume by filling through the sample well or, preferably, through the vent. The reagent can then be freeze-dried, the exact conditions of the freeze-drying process being dependent upon required optima and the type of reagent employed. There is thus produced a reaction slide, ready for use, having a premeasured amount of reagent disposed therein.

Typically, it may be desired to modify the internal surfaces of the reaction slide which will contact the sample or reagent or both to modify the liquid/solid/air contact angle of the surfaces, the surfaces thus being treated to increase their hydrophilic character. Such treatment will increase the ease with which the sample flows from the sample well to the reaction volume.

There are a variety of methods available for decreasing contact angle on a hydrophobic (or nonpolar) surface, thereby rendering it more hydrophilic. Surface active agents (or surfactants) which are typically employed as wetting agents may be used. For example, small amounts of Triton (a nonionic surfactant) type dispersion agents, TWEEN (polyoxyethylene derivatives of fatty acid partial esters of hexitol anhydrides) type surface active agents, and BRIJ (polyoxyethylene ethers of higher aliphatic alcohols) type wetting agents may be utilized. Surface modification via chemical derivitization of surface molecules can create polar prosthetic groups. Other techniques include surface modification using controlled electrical discharge or plasma treatment.

Figure 18B:
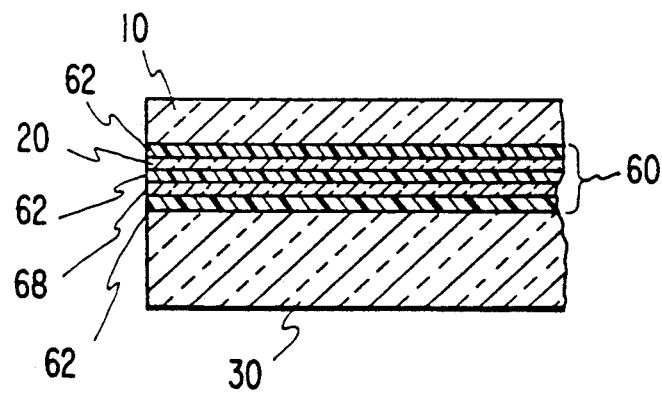
Figure 18C:
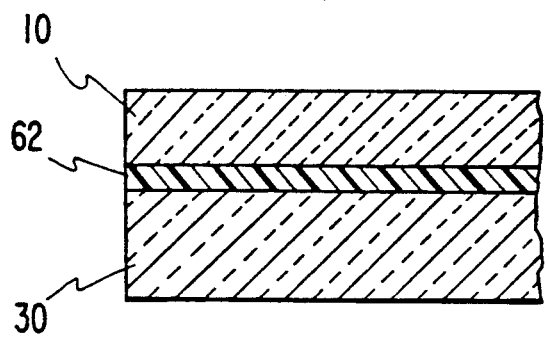

It should be noted that the height of the reaction volume is critical and is defined by the thickness of the spacer 60 (see FIG. 18b. This height should be uniform and can range from 0.001 to 0.02 inches (approximately). Typically, this height is preferably from 0.002 inches to 0.008 inches, and most preferably approximately 0.006 inches.

This order of magnitude is not only appropriate to achieve functional capillary action in the channels but is of the same order of magnitude as is required, generally, for optical waveguide transmission of light by total internal reflection. Coincidentally, this dimension is approximately of the order of magnitude required to produce preferential phase separation to the center of a flowing stream of suspended particulate or cellular material in a two phase system (or suspension) during sustained laminar flow conditions which may be achieved, as is described in U.S. patent application Ser. No. 07/033,817, filed Apr. 3, 1987, now U.S. Pat. No. 4,849,340, which is hereby incorporated by reference.

For construction of the reaction slide, all materials which come in contact with sample or reagent should be relatively inert. The surface properties of the materials should be such that appropriate wetting of the surface is achieved by the sample to provide proper flow conditions. Generally a small contact angle is best.

Cover 10 may be fabricated from a solid thin sheet of paramagnetic material or a laminate consisting of a coated paramagnetic material or could be fabricated from plastic or glass.

The paramagnetic material could be iron or nickel. Chemically inert thin coatings, such as polyvinyl chloride, acrylic, or polycarbonate could be utilized. A polymer with encapsulated iron oxide (e.g., magnetite) could be utilized as well.

The cover also could be fabricated from a variety of glasses and fused quartz. Polymeric materials which could be advantageously utilized include: polycarbonate, PET (polyethylene terephthalate), PETG (glycol-modified polyethylene terephthalate), acetate, acrylonitrile, and cellulose nitrate. A variety of coextruded films, composites and polymer alloys may also be used. Of primary importance are dimensional stability, stiffness, resiliency, and optical clarity (when required). The ability of a material to be fabricated in thin sheets is also a factor. Methyl methacrylate and polystyrene are both potentially suitable materials but are difficult to fabricate in thin sheets.

The cover is typically of greater surface area (or projected area) than the reaction volume. The cover may typically assume the same length and width as the spacer (e.g., 2 inches × 0.5 inches) but could be larger, if required, or smaller.

Materials which may be utilized to produce a good to excellent overlay include: polycarbonate, PETG, methyl methacrylate, polystyrene and glass. However, glass is difficult to fabricate into the required shapes. Materials which may be utilized to produce a good to moderately good overlay include: polyvinyl chloride, nylon (polyamides), PET or polyethylene terephthalate (e.g. mylar), and acetate. Materials which may be utilized to produce an acceptable overlay include: acrylonitrile, low density polyethylene film, PP/EVA coextruded film, EVA/nylon/EVA coextruded film, PP/EVA/PE/EVA coextruded film, and oriented polypropylene film. (PP=polypropylene; eVA=ethylenevinylacetate; PE=polyethylene). Materials which may produce an overlay of marginal acceptability include: XT ® (an acrylic-based multipolymer modeling and extrusion compound produced by CYRO Industries, Woodcliff Lake, New Jersey) and high density polyethylene film. In general, the better materials provide better waveguides because they have lower light scatter losses and transmit well in the visible spectrum where the most commonly employed excitation wavelengths may be found.

There are many adhesives which can be employed to secure the overlay to the cover and base. Acrylic adhesives are generally good. The best adhesives retain some flexibility, are transparent, and have low light scatter losses when cured, pressure treated, or otherwise activated. The length and width of the overlay may be varied over a wide range, but could be typically and approximately 2 inches ×0.5 inches on a 3 inch ×0.75 inch base. Thickness of-the spacer is typically in the range of 0.002 to 0.010 inches. Thinner spacers may occasionally result in impeded capillary channel flow. Thicker spacers tend to lose liquid at the air interface adjacent to the edge of the reaction volume due to poor capillary action at larger diameter conduits.

The base is a solid support and can be made from a variety of materials. It should be rigid enough to maintain and support the reaction volume geometry, transparent in the reaction volume region (if required for monitoring) and capable of being bonded to the spacer/cover component. Fluorinated hydrocarbons such as TEFLON polytetrafluorcethylene make poor bases because they are difficult to bond. Glass is an acceptable material. Excellent bonding may be achieved with polycarbonate or methyl methacrylate base materials. A typical minimum thickness for the base is approximately 0.008 inches for a material such as polycarbonate. An aluminum base (if transparency is not required) could be thinner. If the base is too thin, it may bend too easily and alter the volume of the reaction volume unintentionally during handling or manipulation during an assay. If the base is too thick, it may take too long to achieve thermal equilibrium for a temperature controlled assay. This is especially true for materials with low heat conductivities. The length and width of the base are variable.

The base could be as small as 0.25 inches in width and 1 inch in length (or even smaller). Typically, the base will be approximately 0.75 inches in width and 3 inches in length. This provides enough room for a sample well, connecting conduit, and reaction volume with vented end. There would also be an area to grip the slide with thumb and forefinger for handling and placement and another area for an optically or magnetically readable code to provide information to the analytical instrument employed. This information might include the type of assay, control parameters, calibration information for that batch of reagent, etc. As will be described later, the base could be wider (or longer) if multiple assays are to be performed on the same sample. In such a case, multiple reaction spaces might be used in parallel (or series) communication with the sample well. The base could consist of a composite material (e.g., two layers, such as a lower layer of aluminum, iron, or other metal with a hole under the reaction volume. Atop this layer and affixed thereto would be an upper layer of transparent material, such as polycarbonate, which would define the bottom of the reaction volume to allow light transmission through the hole in the lower layer.

A reflective layer can be used to enhance light transmission. Such a layer can be made by applying a thick film of aluminum paint. Other methods include chemical deposition of silver metal and vacuum vapor deposition of silver or aluminum. Another fabrication technique is to employ metallized heat sealable film, for example, metallized linear low density polyethylene (LDPE) film of approximately 20 microns thickness (or less). Other metallized polymer films may also be utilized if coated with a heat sealable material such as polyvinylidene chloride. An example is metallized heat sealable polypropylene film (polypropylene coextruded with heat sealable materials). Other possibilities include metallized cellophane coated with a heat sealable material. Metallized films may be heat sealed or glued with an adhesive (e.g. cyanoacrylates) to the base and cover of the reaction slide. Metallized glass may also be utilized.

Figure 23:
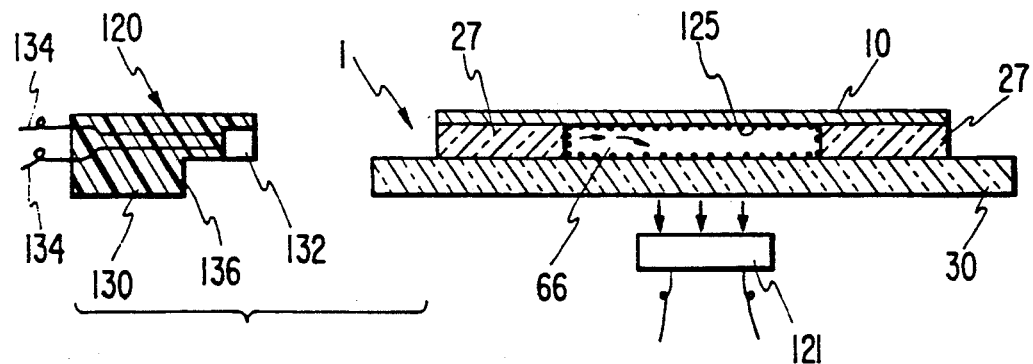
FIG. 23 shows a transverse cross-sectional elevation of a reaction slide, an embodiment of a light source, also in section, and a light detector, the light source and light detector being disposed for making a light scatter measurement.

Shown in FIG. 23 are a transverse vertical cross-section of a preferred embodiment of an external light source 120, a transverse vertical cross-section of a representative embodiment of a reaction slide 1, the cross-section being taken in the region of the reaction volume 66, and a light detector 121 disposed beneath the reaction slide 1 in the area of the reaction volume 66. A dried reagent 125 is deposited on the walls of the reaction volume 66.

In this embodiment, the light source 120 comprises a plastic housing 130 supporting an LED 132 having electric leads 134. As shown, a step 136 is formed in housing 130. As shown, the cover 10 may be made of an opaque material such as a metal.

In use, the light source 120 and reaction slide 1 will mate such that the step 136 receives the base 30 of the reaction slide and the LED 132 is disposed above the base 30 and in contact with or closely adjacent an internal waveguide 27 of the reaction slide.

Figure 21:
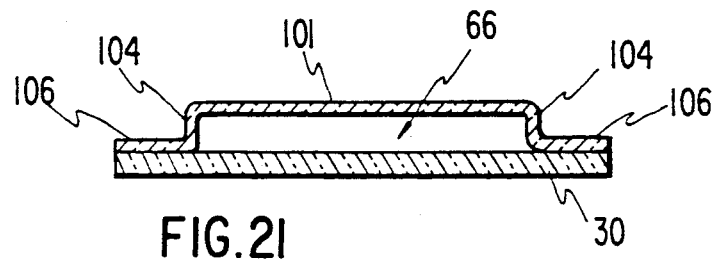
FIGS. 21 and 22, respectively, are elevational cross-sections taken on lines XVII—XVII and XVIII—XVIII of FIG. 20.
Figure 22:
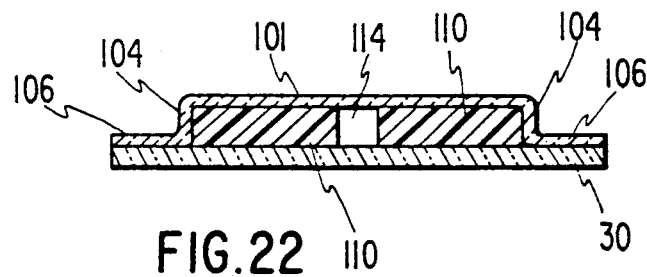
Figure 24:
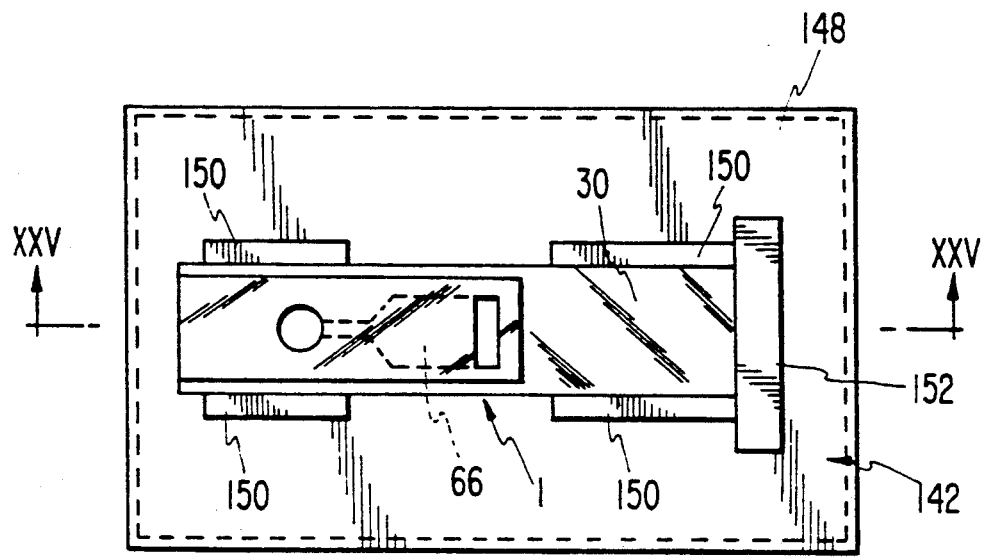
FIG. 24 is a top view of a reaction slide disposed in a housing for making a light scatter measurement, a cover of the housing being removed.
Figure 25:
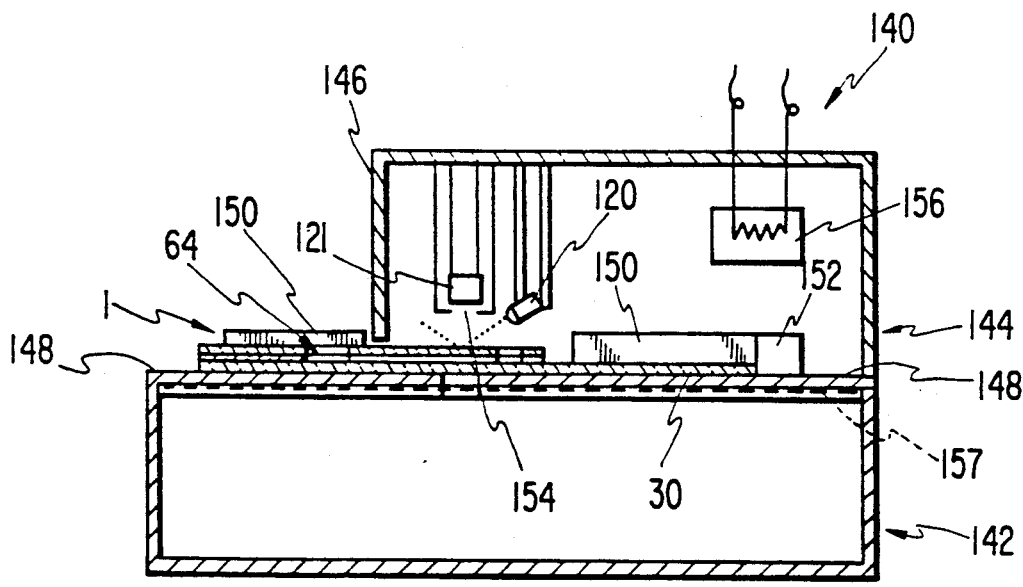
FIG. 25 is an elevational cross-section taken on line XXI—XXI of FIG. 24, also showing the cover of the housing.

The arrangement illustrated in FIG. 21 is designed to employ a light path such as that shown at 41 in FIG. 16. A more detailed example of instrumentation for accomplishing such measurement by monitoring light scatter through the reaction slide base is shown and discussed in U.S. patent application Ser. No. 07/033,817, filed Apr. 3, 1987, which is hereby incorporated by reference. In FIGS. 24 and 25, an instrument is shown for measuring light scatter or reflectance through the reaction slide cover. Housing 140 comprises lower housing 142 and cover 144 resting on or integral with lower housing 142. A lower end of wall 146 of cover 144 is spaced from the top 148 of lower housing 142 by a distance which is sufficient to allow the reaction slide 1 to be inserted. Lateral guides 150 and stop 152 establish a proper position of reaction slide 1 for a measurement. Light source 120 and light detector 121 are disposed within the housing 140, as shown. There is provided an aperture 154, disposed immediately beneath the photodetector 121 to resist the angle of reflected or scattered light passing through the cover of the reaction slide.

Sample well 64 of reaction slide 1 is disposed outside the housing 140, such that the reaction slide 1 may be inserted into the housing 140 before a reaction is initiated.

The light detector 121 may be used to monitor the progress of sample entry into the reaction volume 66 and the subsequent progress of the reaction within the reaction volume 66. The light source 120, reaction volume 66 and light detector 121 are disposed in a portion of the instrument that is isolated from ambient light. Desirably, those portions of the reaction slide 1 which are exposed to ambient light are made of opaque materials or are painted so as to aid in the exclusion of stray light from the reaction volume 66.

Temperature control is provided for the reaction slide by means of heaters of a thermal control system, illustrated schematically as element 156. One form of such a heater may be a resistive heater strip 157 fastened to the bottom of plate 148. Regardless of the form of thermal control system used, it is desirable that it be capable at least of maintaining the temperature of the plate 148 at 37° C.

The instrument shown in FIGS. 24 and 25 is not of a standard commercially-available type but is instead custom designed for use with reaction slides. As in the case of other instruments currently available for decentralized testing, optical or magnetic code reading capability is preferably present to provide for identification of the assay to be performed and of the particular reaction slide being used, along with calibration information. Such a code may be affixed to the reaction slide during manufacture. In addition, other structures may be present to provide for mixing when required (described below). As also described below, there will desirably be associated with the illustrated instrumentation a system microprocessor, display or other data presentation means, any necessary analog-to-digital converters, power supplies, and the like.

As may be seen from a consideration of FIG. 25, it is desirable for the spacing between the lower end of wall 146 and the plate 148 to be as low as possible to aid in the exclusion of ambient light.

Figure 26:
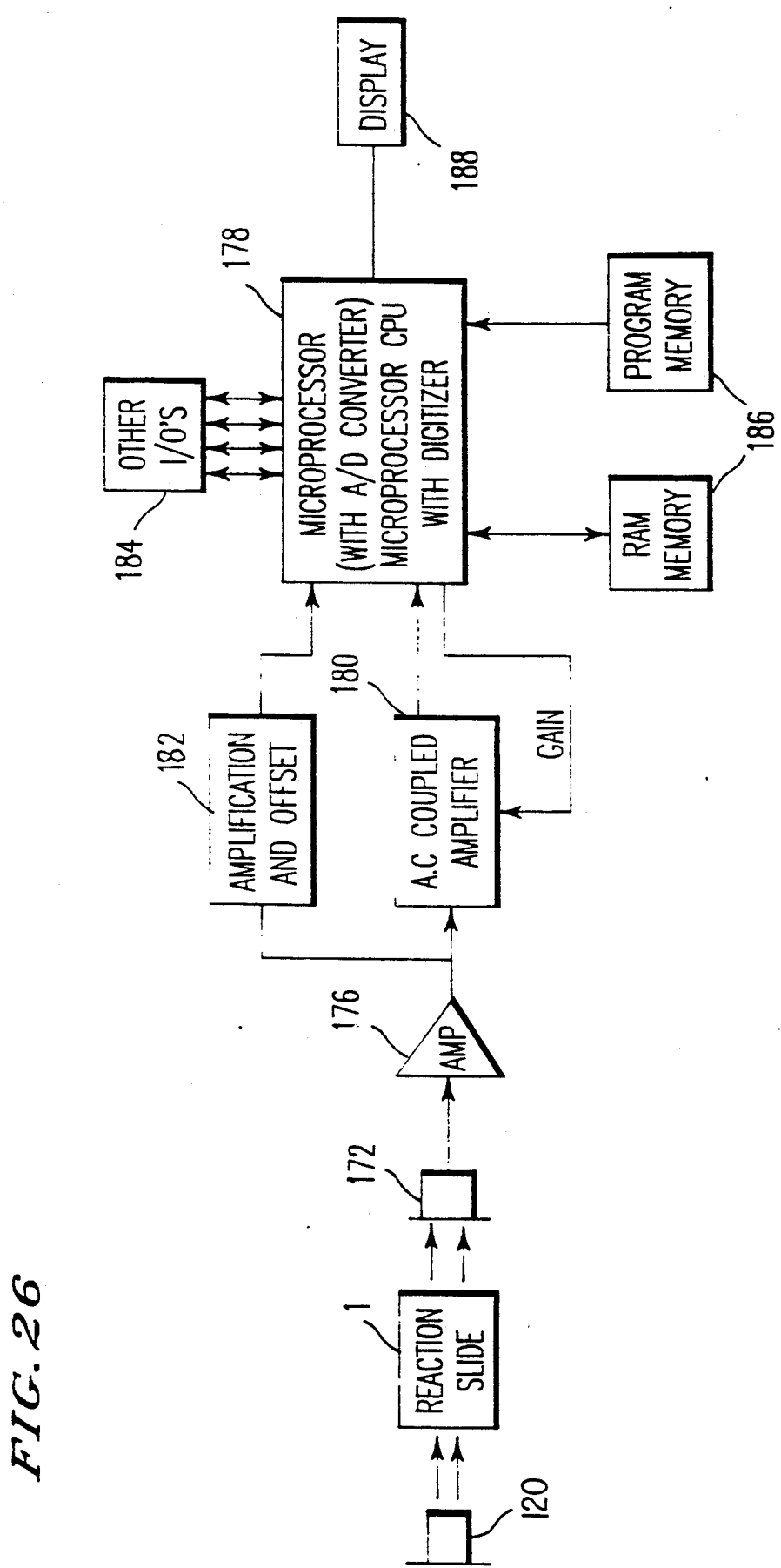
FIG. 26 schematically illustrates an apparatus for measuring prothrombin time.

FIG. 26 shows a simplified systems block diagram of how the analog signal received by a detector may be interpreted. The light source 120 transmits light through the reaction volume of reaction slide 1. Reflected or scattered light is monitored by the photodetector 172 and amplified at 176. Further amplification and offset of the D.C. signal is accomplished by amplifier circuit 182. The A.C. coupled signal amplifier 180 is gain selectable by the microprocessor CPU 178, as shown. Digitizing is accomplished at 178 using an on board A/D converter, and peak and slope detection are accomplished by the CPU 178 plus memory blocks 186. From the output of 180, signals for start time and endpoint detection are determined, using an appropriate algorithm. The microprocessor CPU, 178, has other inputs and outputs 184. These could include functions for temperature control, external data input, etc. Block 186 contains data and program memories. The results are read on the display 188. In addition to monitoring the assay kinetics, the dynamics of sample entry into the reaction space and initial interaction with the reagent are monitored, as well, as a consequence of the geometry and structure of the reaction slide. The initial portion of the curve therefore provides information for quality control of proper sample addition.

The above instrument shows an example of how a measurement may be made by light scattering or reflectance. This measurement approach is advantageously utilized with the reaction slide system shown in FIG. 5. In FIG. 5 a reaction slide 1 is shown disposed above and in close proximity to a permanent magnet 195. Beneath the permanent magnet 195 is an electromagnet 196 which is driven by a power supply 199 for cycling voltage on and off at a desired frequency. There is also situated a light source (not shown) for providing incident light and a detector positioned for detecting light rays reflected from the sample within the reaction volume 66.

The reflected rays illustrated as rays 198 are detected by a detector 400. Detector 400 can be theoretically positioned at any position between the 90° and the 10° positions, inclusively, shown in FIG. 5. However, as one approaches angles less than 45°, it is more probable that the critical angle will be reached, such that total reflection of incident light off of the cover will prevent the reaction from being monitored. Preferably detector 400 can be positioned between 90° and 45°, most preferably between 90° and 75°.

A measurement which can be conducted with such apparatus will now be described. The reaction slide was prepared in advance by forming a slurry of a coagulation reagent and inert magnetic particles suspended in the reagent. The coagulation reagent was thromboplastin-calcium, and the magnetic particles were magnetite. Inert magnetic particles work well when provided in the range from approximately 5 to 50 milligrams per milliliter of liquid reagent. The slurry was applied to the reaction slide and freeze dried.

To perform the assay, the reaction slide 1 was introduced to the apparatus in position as shown in FIG. 5. The light source was a light emitting diode, and the detector was a silicon photodiode. A chart recorder was AC-coupled to a photodiode amplifier. The permanent magnet 195 was in the form of a sheet (which may be made of a flexible or rigid magnetic material). The power to the electromagnet was cycled at a frequency of 1 Hertz. A sample of plasma was introduced into the sample well 64 and filled the reaction volume 66, solubilizing the dry reagent, resuspending the magnetic particles as shown at 197, and initiating the coagulation reaction. The permanent magnet 195 causes the magnetic particles to be drawn downwardly in clusters or stacks and lie down against the base 30 in an orientation parallel to the plane of the permanent magnet. However, each cycle of energy supplied to the electromagnet 196 causes the stacks of magnetic particles to stand upright like tiny whiskers in an orientation of alignment along vertical field lines. At the end of each such energy cycle, the particles lie flat again.

The detected reflected light 198 shows a time-varying pattern of light intensity in accordance with the above-recited changes in orientation of the magnetic particles. The light intensity is less when the particles lie flat than when they stand upright.

The detected light intensity shows an initial peak at sample addition. Thereafter, the detected light intensity cycles between maximum and minimum values in accordance with the frequency of the cycling of the electromagnet 196. During the period before clot formation, the difference between the maximum and minimum values of the detected light intensity increases. However, the peak-to-peak light intensity oscillations begin to fall off from their maximum values when a clot has started to form. At this point, the endpoint has been reached. In the case of prothrombin time, the elapsed time between the sample addition peak and clot formation or clot onset (endpoint) is easily measured. Resolution may be increased somewhat by increasing the oscillation frequency.

For determining prothrombin time, the above-described approach works extremely well using whole blood as well as plasma. It is expected to work well for other types of blood coagulation assays. The measurement may be made using transmitted light instead of the described method of using reflected light. However, it is thought less convenient to use transmitted light than reflected light.

Alternative means for introducing light into the reaction volume 66 for various measurements will now be discussed together with a discussion of other types of optical measurements. A complete discussion of optical measurements based on transmission/absorbance, chemiluminescence, light scatter, reflectance, fluorescence, and combinations of these techniques is found in U.S. patent application Ser. No. 07/033,817, filed Apr. 3, 1987, now U.S. Pat. No. 4,849,340, which is hereby incorporated by reference.

Figure 28:
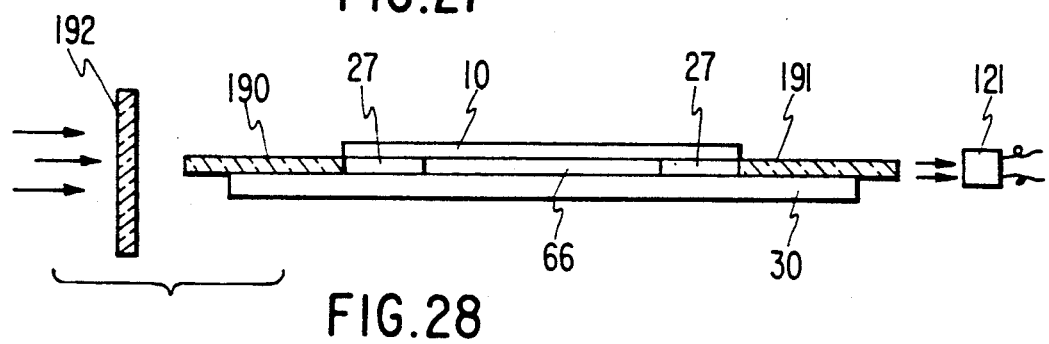
FIG. 28 illustrates the use of a reaction slide (unsectioned), external waveguides and apparatus for making a transmission/absorbance measurement.

Transmission/absorbance, or optical density measurements, involve measurement of the ratio of light intensity before and after light passes through a sample in the absence of (or excluding) scattering. The Beer-Lambert Law describes the phenomenon. Standard detectors are employed in a "line of sight" configuration with the light source, as shown in FIG. 28. Incandescent or LED light sources may be used.

FIG. 28 also illustrates an alternative means of introducing light into the reaction slide and of measuring light that has left the reaction slide. In particular, there are provided two external waveguides 190, 191 which respectively carry incident light to one of the internal waveguides 27 of the reaction slide 1 and receive light that has been passed through the other internal waveguide 27 and channel the received light to the photodetector 121. The external waveguides 190, 191 may be made of the same types of materials used to produce the overlay 20 of a reaction slide, as described previously. Accordingly, it may be seen that use of an external waveguide or waveguides 190, 191 provides structure for introducing light into the reaction slide 1 that is alternative to the polymeric housing 130 illustrated in FIG. 23.

An optical filter 192 may be used for wavelength selection.

In FIG. 28, colorimetric or turbidometric measurement is achieved. Light rays pass through filter 192, travel through external waveguide 190 and through an internal waveguide 27, then illuminate reaction volume 66. They pass through the reaction volume, through the internal waveguide 27 at the right, and are transmitted through optional second external waveguide 191. The light rays are then directed to an appropriate detector 121.

Figure 29:
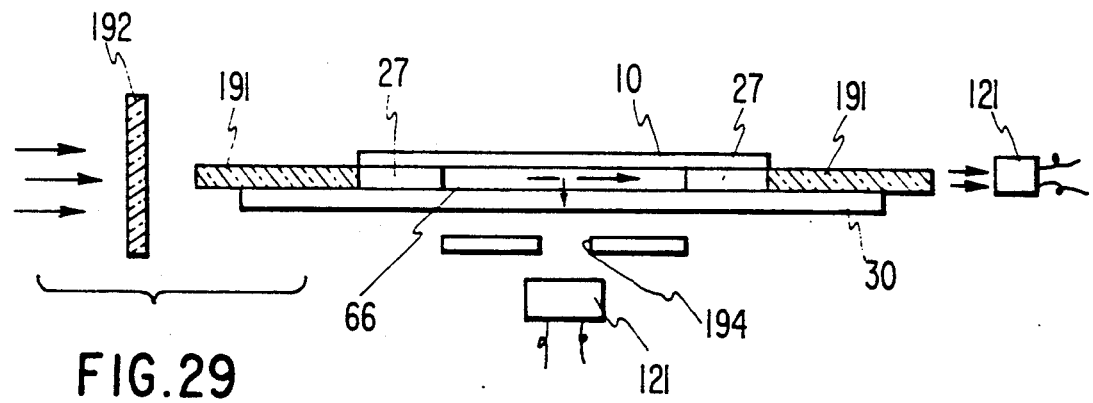
FIG. 29 is a view similar to that of FIG. 26, illustrating simultaneous measurements of light scattering and transmission/absorbance.

In FIG. 29, a second light detector 121 for detecting scattered light and an aperture 194 to restrict detection to light scattered at or near 90° have been added to the arrangement of FIG. 28. FIG. 29 illustrates an embodiment which allows simultaneous detection of scatter (in this case at 90°) and absorption. It is based upon a combination of light paths 40 and 41 in FIG. 16. This monitoring strategy may be useful during the formation of precipitates or large polymers with characteristic absorption spectra.

Figure 30:
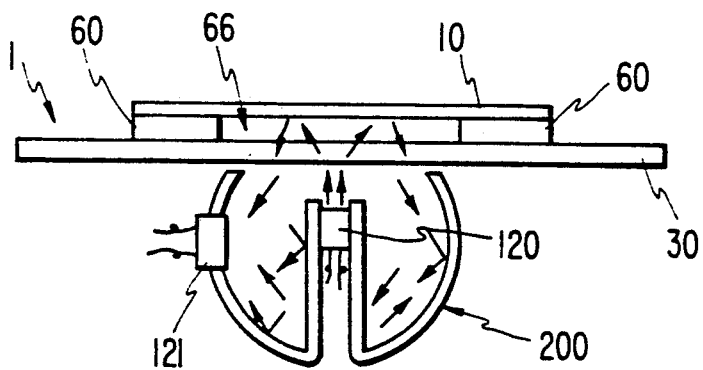
FIG. 30 shows a reaction slide disposed above a partial integrating sphere for making a measurement based on reflectance.

FIG. 30 shows an embodiment based upon conventional reflectance measurement. A partial integrating sphere 200 mounts a light source 120 and a light detector 121. The partial integrating sphere is positioned beneath the base 30 of a reaction slide 1 having a reaction volume 66 and cover 10. Rays reflected back into the partial integrating sphere from within the reaction slide are detected to allow measurement of the reaction. It should be noted that the spacer 60 is not employed to provide internal waveguides for transmission.

More generally, such reflectance measurements capture light reflected in any desired direction from surfaces or surface layers. A photodiode or photo-conductive cell may be used along with a filter for wavelength specificity. The Kubelka-Monk Theory is a useful model for reflecting systems.

A further method of detection may be based upon fluorescence and involve the use of materials which are fluorescent and hence absorb ultraviolet light and emit light of a longer wavelength, frequently in the visible range. Fluorimetry may be used in a reflective mode, similar to photodensitometry, for example to quantitate samples on chromatograms. Variations are possible, together with the use of fluorescence in combination with other modes of detection. For example, a detector may be placed at a fixed angle, typically 90°, from the direction of transmission through a sample, as in nephelometry. As will now be described in connection with FIGS. 11 and 12, reflectance based measurements using a membrane or gel layer as an integral part of the reaction slide may be readily achieved.

FIG. 11 illustrates how a reaction slide may be used to perform reflectance measurements. As seen in the diagram, a semipermeable layer (e.g., a membrane or gel layer) 40 is situated within the reaction volume 66 of the reaction slide. This layer is affixed to the cover 10 such that the layer is available to absorb liquid and dissolved species which may be introduced into the reaction volume 66. One surface of the layer is firmly attached to or contiguous with the upper inside flat surface of the reaction volume. This attachment or contiguity prevents liquid and/or liquid plus dissolved species from contacting or permeating the attached or contiguous portion of the layer surface without first passing through other portions of the layer and thus, in effect, provides a window along with the transparent cover 10, to allow color changes in the layer to be readily observed.

The layer provides a reference background of known reflectance, against which color development may be measured quantitatively. Most membranes, membrane-like layers, or gel layers undergo a distinct change in reflected light intensity when wet, seen typically as a decrease of light intensity. The layer 40 therefore, while preventing direct observation of the sample when introduced into the reaction volume 66, will signal the exact moment of entry of sample into the reaction volume due to the reflectance change upon wetting of the membrane. Sample permeation and "wetting" in many types of membranes or gel layers of appropriate hydration (for gels), hydrophilic nature, thickness, and pore size is coincident with entry of the sample into the reaction volume. In some cases, whiteners such as titanium oxide when added to the membrane or gel improve performance by increasing reflectivity.

Illustrative dimensions of a reaction slide in accordance with this embodiment are given in Table 1 below. The membrane or gel layer structure may be made of a circular sheet with its diameter smaller than the smallest dimension of the reaction space. Alternatively, the membrane or gel layer structure may be configured to match the shape of the reaction space with its edge adjacent to the spacer/overlay. The membrane or gel layer structure may consist of a plurality of discs, squares, or other shapes, each containing different reagents, so that multiple reactions may be monitored.

TABLE 1

| Dimensions: Material Thickness (Approximate) |
| --- |
| 1. Cover (0.010 inch) |
| 2. Spacer* (.010 inch) |
| 3. Transfer adhesive (.002 inch) |
| 4. Membrane or gel layer (.004–.006 inch) |
| 5. Base (0.010 inch) |

*Spacer/Overlay

The adhesive for attachment of the semipermeable layer to the reaction slide which works best is of the form used in pressure sensitive applications where a transparent bond is desired. Pressure sensitive adhesives will adhere to the membrane or gel layer without flowing into the pores and thereby compromising membrane function. Although a double sided adhesive tape or film could be used to affix the membrane or gel layer to the reaction slide, the use of a transparent, pressure sensitive adhesive without a film layer provides a good bond, is easy to use, and is generally thinner than double sided adhesive tapes. An acrylic transfer adhesive which comes in rolls with a peel off backing works extremely well.

The semipermeable layer can be constructed such that suspended material may be excluded and only liquid and dissolved species or suspended species may penetrate the interstices or pores of the layer. In the case of dissolved or suspended species, layers with a particular upper limit of pore size will thus determine the largest molecules, ions, colloids, etc. which can enter. Surface charge on the layer could also play a role here in determining thresholds for charged species. All of this is well known in the art of, e.g., membrane or gel layer fabrication, and many kinds of commercially available membranes exist in standard or custom formulations.

The semipermeable layer may also be constructed to exclude blood cells from a whole blood sample and thereby enable whole blood assays to be achieved without independent separation steps such as centrifugation, which requires extra equipment, is time consuming, labor intensive, and involves extra handling of blood specimens. The red color due to hemoglobin in the blood may therefore be essentially eliminated, providing a wide range of wavelengths which may be used to measure chromogens, without Soret band interferences playing a significant role.

Illustrative membranes are provided below.

| Material | Pore Size (microns) | Coating | Approximate Thickness (in) | Whole Blood Separation Ability | Color Development |
|---|---|---|---|---|---|
| Nylon | 0.22 0.45 0.65 | PEG (20%) in water | .004" | excellent | excellent |
| Nylon | 0.45 | PEG (20%) in water | .005 | excellent | excellent |
| Nitrocellulose | 0.45 | PEG (20%) in water | .005 | excellent | excellent |
| Nylon (negatively charged) | 0.65 | PEG (20%) in water | .005 | fair | good |
| Polysulfone | 0.45 | PEG (25%) in water | .006 | excellent | excellent |
| Fiberglass | 20.2.0 | PEG (20%) in water | .005* | excellent | excellent |
| Fiberglass | 20-2.0 | uncoated | .005* | good | excellent |

Membranes tested with whole blood containing Evans Blue dye.
[Note
Evans Blue dye is known to dissolve in plasma and neither attaches itself to, is absorbed by, nor enters red blood cells. The molecular weight of Evans Blue is less than 1000 daltons.]
*Without backing (backing was removed prior to using membrane).

The gel layer can be an agarose gel layer, a polyacrylamide gel layer or a gelatin gel layer.

A reagent or mixture of reagents may be added to the semipermeable layer (e.g. prior to assembly of the slide). In some cases, it may be advantageous to bind or immobilize reagents directly onto the semipermeable layer. In addition to the possible use of dry reagents in the semipermeable layer, other dry reagent layers may be utilized in the reaction volume of the reaction slide, these layers containing the same or different reagents. Multilayer structures made up of a plurality of semipermeable layers can similarly be used, providing a wide range of possibilities for assays involving multiple reagents, molecular size selection/exclusion, and immobilized reagents.

FIG. 12 shows a sectional view of the reaction slide in FIG. 11. The semipermeable layer 40 is situated within the reaction volume 66 and attached to the cover 10 by means of a transparent adhesive layer 42. Light rays 43 projected through the cover 10 from a light source, not shown, are reflected at the semipermeable layer. The light rays are projected at an angle which will keep reflected rays at the same angle to the normal (angle of reflection) from directly impinging upon the photodetector 121 to prevent glare. The photodetector 121 may require an aperture 204 to restrict the view to the semipermeable layer portion of the reaction slide, so that the projected area of the reaction volume 66 between the layer 40 and the spacer/overlay 20 will not be viewed. The spacer/overlay 20 may be of slightly greater thickness than in a reaction slide without a semipermeable layer to leave sufficient room for the semipermeable layer and to allow for rapid filling of the portion of the reaction volume below the semipermeable layer.

A further variation is to use magnetic particles in the reaction volume 66 between the layer 40 and base 30 to provide controlled convection when the magnetic particles are driven into an oscillating mode via the time varying applied magnetic field. This is discussed more fully later on and shown in FIG. 34.

Various exemplary methods for inducing forced convection currents within the reaction volume 66 of a reaction slide 1 will now be described with reference to FIGS. 31-34. Such forced convection currents promote rapid and thorough mixing.

Figure 31:
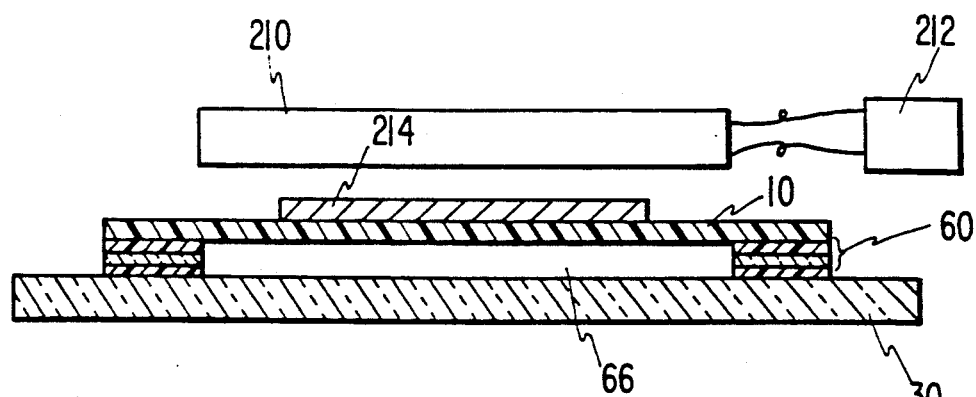
FIG. 31 illustrates the use of a permanent magnet on the cover of the reaction slide for setting up convective currents in the reaction space.

FIG. 31 shows an alternative arrangement for mixing. In this figure, permanent magnet 214 is affixed to cover 10 and driven into an up/down oscillation by electromagnet 210 supplied by an electrical driving signal from 212. The cover 10 moves along with the magnet 214 as essentially one unit, causing periodic alterations in the volume of the reaction volume 66. The inflow and outflow of liquid produces mixing. The mixing resulting here is well suited for moving liquid in the vicinity of the cover/liquid interface. To achieve this type of mixing, the cover 10 may be fabricated from a thin paramagnetic material, obviating the need for a separate magnet 214. If a separate magnet is used, it may be doughnut shaped, or disc shaped. It may also be made of flexible ceramic magnetic material.

Figure 32:
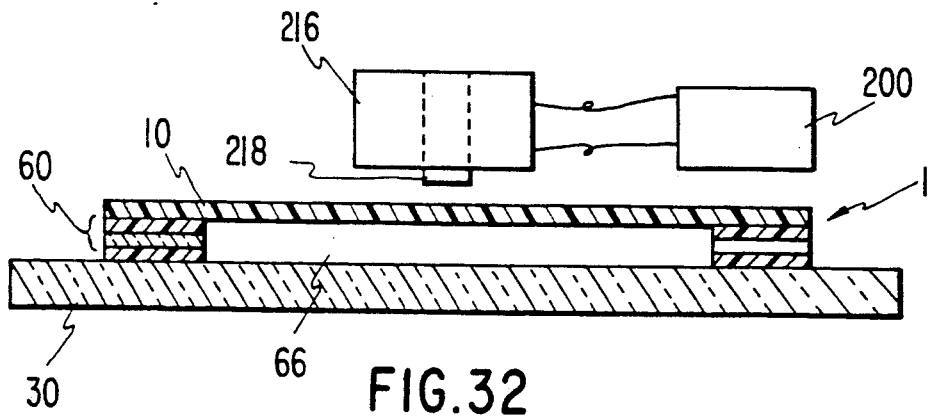
FIG. 32 illustrates the use of a solenoid for setting up convective currents within the reaction space.

FIG. 32 shows an arrangement which provides yet another alternative for producing and sustaining a controlled convection within the reaction volume 66. In this case, a solenoid 216 is employed, having a rod 218 and a coil which is driven by an appropriate intermittent unidirectional or time varying current source 220 to push rod 218 against and deflect the cover 10. The solenoid may be spring-loaded to retract the rod upward after cessation of the current.

Figure 33:
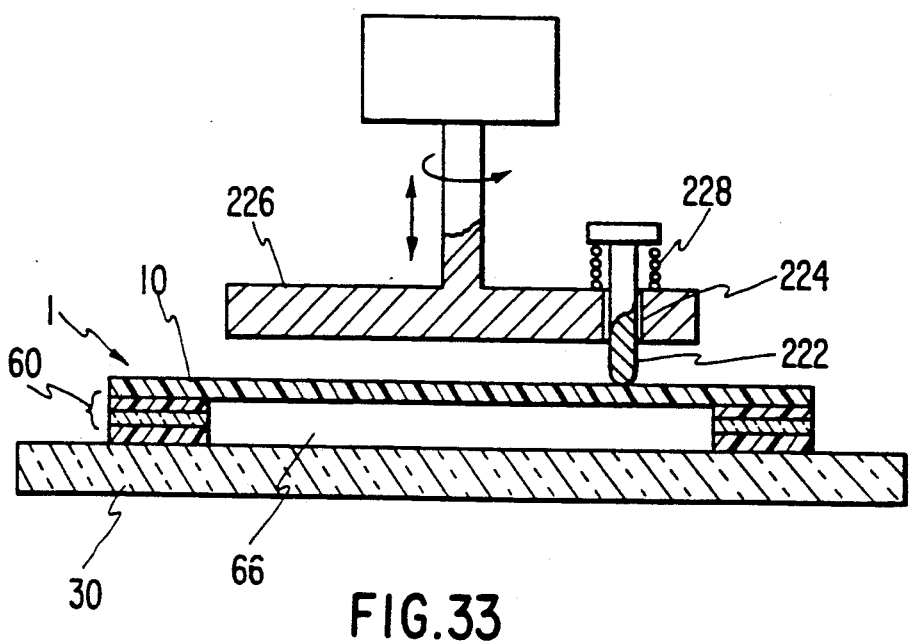
FIG. 33 illustrates an apparatus for producing localized deflection of the cover to produce convective currents within the reaction space.

In the alternative and as shown in FIG. 33, there may be provided a projecting element 222 passing through a hole 224 in an orbiting disk 226. Tension spring 228 biases projecting element 222 downwardly as shown in the drawing. Drive 230 initially moves disk 226 downwardly for contact between the projecting element 222 and the cover 10 of a reaction slide. At such time, projecting element 222 pushes against cover 10 at a localized pressure point with a force, the magnitude of which is governed by spring 228. Thereafter, drive 230 rotates disk 226 about the axis thereof, causing the localized pressure point to trace a circle on the upper surface of the cover 10. The cover 10 accordingly experiences a localized deflection that moves in a circular pattern, following the position of the projecting element 222. Such localized deflection of the cover 10 causes mixing in the reaction volume 66. It has been found that a deflection of 0.005 inches may be produced in a polycarbonate cover 10 by a force of 3 ozs., applied with a projecting element 222 having a 0.100 diameter circular cross-section and a rounded bottom.

Yet another approach to mixing (not shown) is to utilize a cover fabricated from a piezoelectric material or containing a piezoelectric material affixed thereto. In this case, motion of the cover would be produced piezoelectrically by application of the appropriate voltage.

As noted above, a reaction slide according to the current invention may be used to conduct assays in which the results are measured using non-photometric techniques. That is, in addition to transduction of light energy (e.g., transducers of the photoconductive, photodiode or photomultiplier type), the reaction slide may employ other mechanisms for energy conversion. Additional types of transducers that are applicable to a reaction slide according to the current invention include calorimetric transducers, electrochemical transducers and viscosity transducers.

Figure 1B:
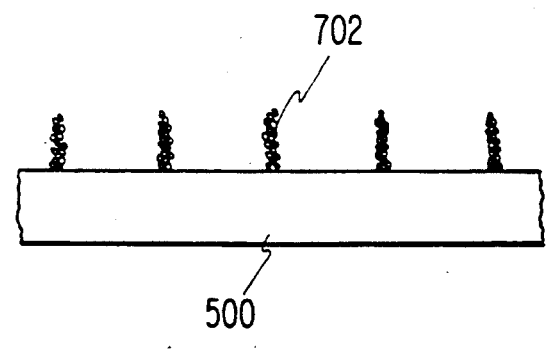
Figure 34:
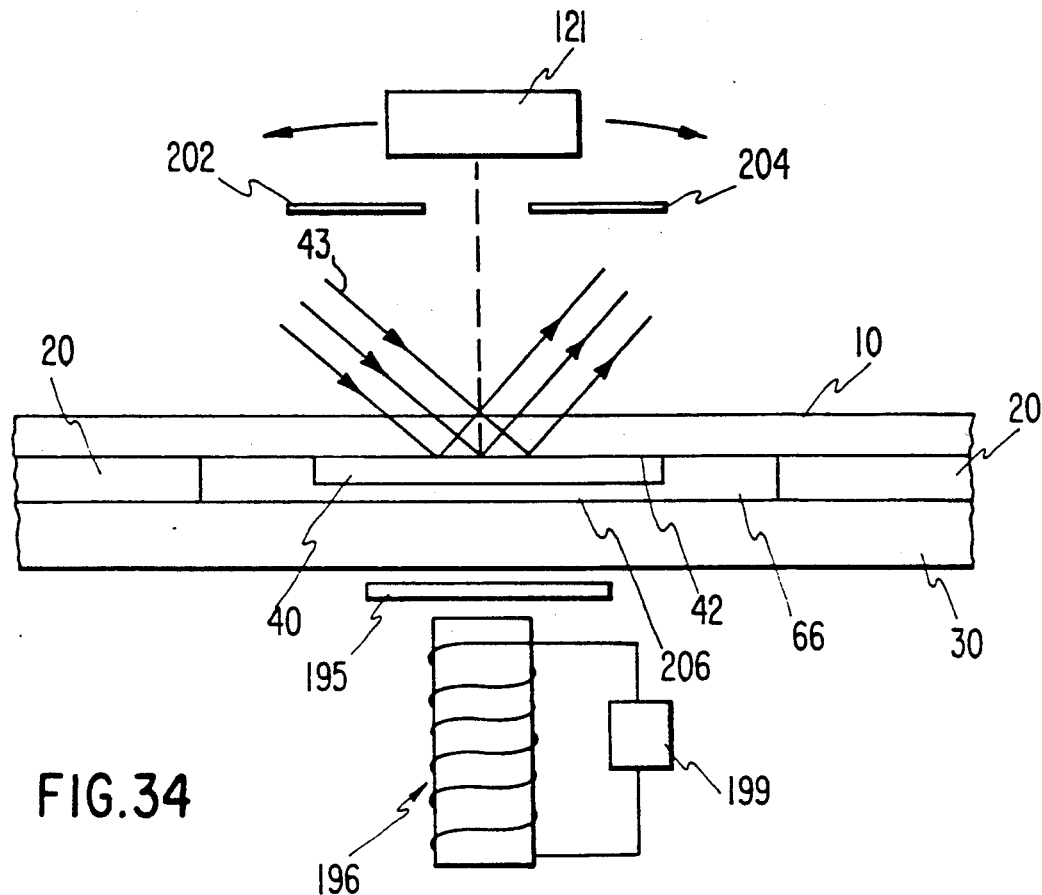
FIG. 34 is a transverse elevational cross-section of a reaction slide provided with a membrane for selective species transport and reflectance measurement with magnetic particles in the reaction volume for setting up convective currents, as driven by the oscillating magnetic field provided.

Shown in FIG. 34 is a transverse vertical cross-section of a representative embodiment of a reaction slide similar to that shown in FIG. 12 but with magnetic particles 206 included within the reaction volume 66. An electromagnet 196 is driven in oscillatory mode (e.g. simple on-off cycling via square wave) by driving circuit 199. The magnetic particles situated at or near the base 30 undergo oscillation, as depicted earlier in FIG. 1. This produces a controlled convective or mixing effect. The mixing will facilitate transport of species to and from the semipermeable layer 40. Light 43 reflected by the semipermeable layer 40 and detected by photodetector 121 will indicate the formation (or loss) of color in the semipermeable layer. Because the magnetic particles are not directly viewed by the photodetector, the flicker effect signal will not be detected, due to the interposition of the membrane, and will therefore not introduce artifacts into the color measurement via reflectance. As the assay proceeds and color generation (or change) occurs, as determined by reflectance, the assay can be effectively monitored at faster reaction rates due to the controlled convection. For this controlled convection to be maximally effective, it may be necessary to tailor the field strength and frequency to the particular assay being performed, so as to achieve the optimum transport of species to and from the semipermeable layer surface.

Figure 35:
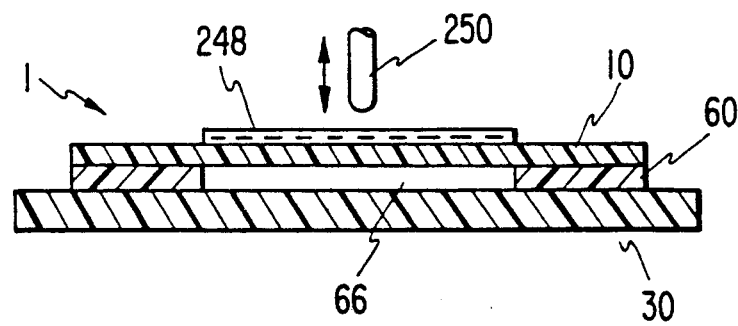
FIG. 35 is a transverse cross-sectional elevation of reaction slide provided with a viscosity transducer.

FIG. 35 illustrates the use of a viscosity transducer. There is shown a strain gage 248 mounted on the cover 10 of a reaction slide 1. Using the strain gage 248, the rate of bending or movement of the cover 10 or, in the alternative, the rate of recovery from a downward push imparted by a solenoid-actuated push rod 250 may be measured. Changes in the viscosity of fluid in the reaction volume 66, such as occur in coagulation reactions within the reaction space, may therefore be measured using viscosity monitoring.

Viscosity monitoring is useful with a type of measurement in which there is established a constant flow of liquid into and from the reaction volume 66. An increase in the viscosity of the liquid within the reaction volume 66 results in increased drag and in retardation of motion of the cover.

As an alternative to the use of a strain gage 248 in viscosity measurements, there may be used a piezoelectric element mounted on the cover 10.

Figure 36:
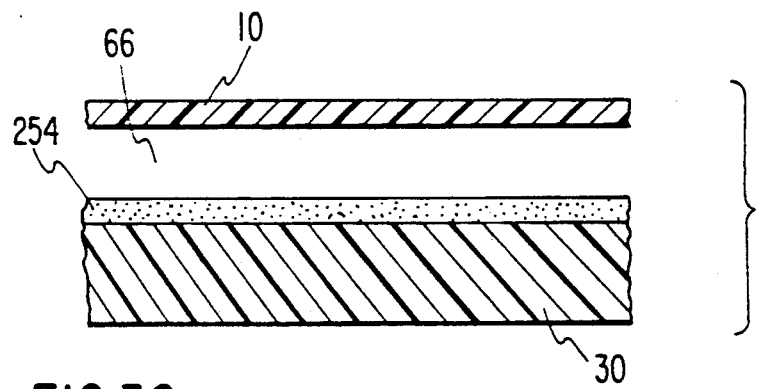
FIG. 36 is a fragment of the area of the reaction volume showing the dry reagent-containing layer situated at the base of the reaction slide.

As has been noted above, a reaction slide according to the current invention provides for the storage of a pre-measured amount of reagent. One manner of providing for the presence of a reagent has already been described in which a liquid reagent is placed in a single reaction volume and then dried, such that the dried reagent coats the interior surfaces of the reaction volume. Other methods will now be described with respect to FIGS. 36-38. Shown in FIG. 36 is a longitudinal cross-section of a portion of a reaction slide 1 according to the current invention. There is shown a reagent-containing layer 254 disposed on the base 30 in the region of the reaction volume 66. If desired, the reagent-containing layer 254 may extend further to the left than shown, occupying the regions of the tapering walls 25, the conduit 26 or even extending into the sample well 64. The illustrated reaction slide is of the type that vents through a vent opening in the cover 10. A reagent layer 254 may be used, however, with any embodiment.

Figure 37:
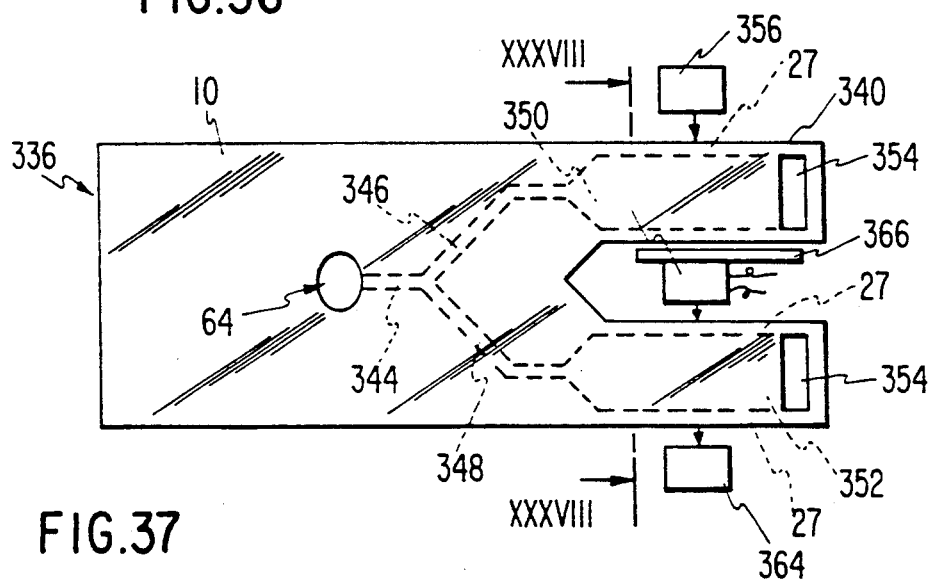
FIG. 37 is a top view of a reaction slide of the parallel flow type having two reaction spaces, also showing light sources and detectors.
Figure 38:
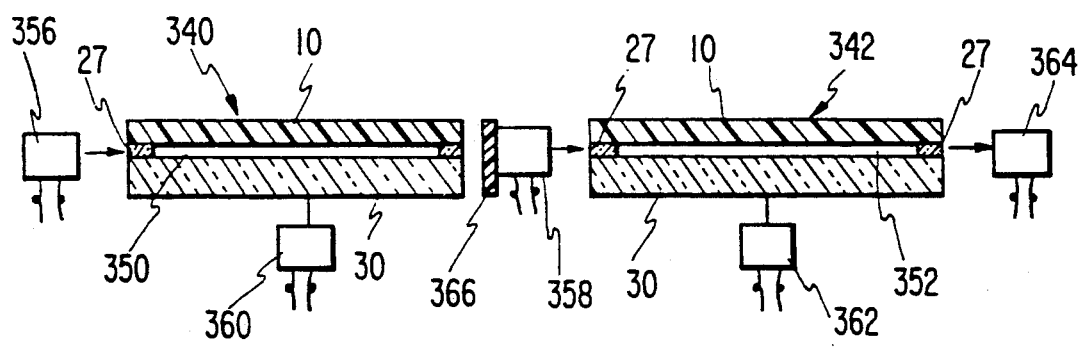
FIG. 38 is a transverse elevational cross-section taken on line LXVI—LXVI of FIG. 37; together.

FIGS. 37 and 38 show a another embodiment 336 of a reaction slide according to the current invention, the reaction slide 336 having plural reaction volumes filled with sample by parallel filling. Among the uses of reaction slide 336 is that it is useful in conducting two assays simultaneously and in monitoring scattered and transmitted light. Also shown in FIGS. 37 and 38 is instrumentation useful in conducting assays with this reaction slide.

In reaction slide 336, the base 30, the spacer and the cover 10 have been cut out as shown at 338 to form first and second legs 340, 342. The cover 10 is provided with an opening for the sample well 64 and openings for each of the vents 354 that communicate respectively with first reaction volume 350 and second reaction volume 352. The spacer is cut out to form the sample well 64 and to form common conduit 344 which branches to form first and second branched conduits 346, 348, the branched conduits respectively leading to the reaction volumes 350 and 352. As in certain of the previous embodiments, the spacer is transparent to provide internal waveguides 27 adjacent the reaction volumes. It will be seen that a sample placed in sample well 64 will be drawn by capillary action through common conduit 344 and will then divide, proceeding through branched conduits 346, 348 and into the reaction volumes 350, 352.

Also shown in FIGS. 37 and 38 are first light source 356, second light source 358, first scatter detector 360, second scatter detector 362 and transmission detector 364. Light shield 366 protects the second reaction volume 352 from receiving radiation from first light source 356. It may be seen that light from first and second sources 356, 358 respectively enters first and second reaction volumes 350, 352, where some of it is scattered at 90° and passes through base 30, whereafter the scattered light is detected at 360 and 362. Transmission detector 364 detects that portion of the light from source 358 which has been neither scattered nor absorbed in reaction volume 352.

Having generally described this invention, a further understanding can be obtained by reference to certain specific examples which are provided herein for purposes of illustration only and are not intended to be limiting unless otherwise specified.

EXAMPLES

Example 1 t-PA Assay:
Ingredients:
(1) 12 microliters of 0.80 mg/ml human plasminogen
(2) 2 microliters of 0.02 mg/ml fragments of human fibrin
(3) 10 microliters of 0.1M S-2251 (H-D-Val-Leu-Lys-pNa) obtained from Helena Laboratories diluted in water.

The ingredients were mixed, added to reaction slides, and were freeze dried in reaction slides containing membrane circles.

Membranes were prepared previously by coating (or impregnating) a commercial material (for example 0.45 micron pore size polysulfone (Gelman Sciences Tuffryn Membrane) with a 10% solution of a polymer (for example polyethylene glycol, average M.W. 3,400). Whiteners (for example Zinc Oxide, Aldrich Chemical Company) may be added to the coating. Dried (47 degrees, 15 minutes) membranes were covered with an adhesive (for example a commercial transfer adhesive such as Scotch 3M transfer tape) and then circles were punched with a paper hole puncher. These membrane circles were adhered to the reaction slide cover.

Figure 41A:
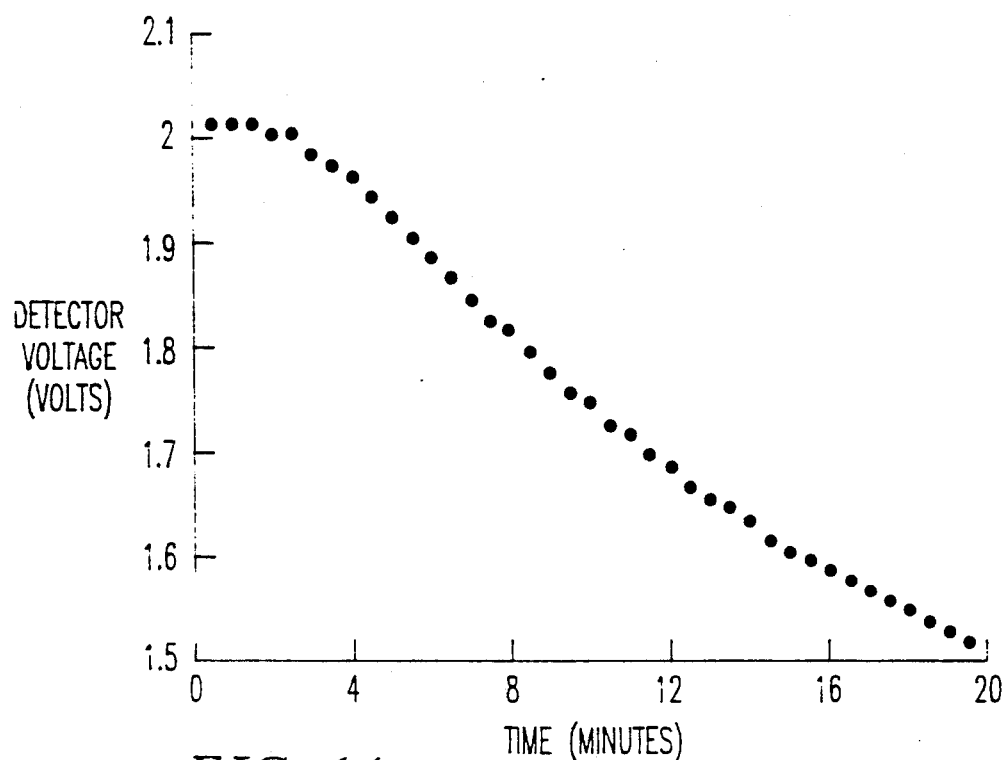
FIGS. 41 (a and b), 42-43, 44 (a and b), 45, 46 (a and b), 47 (a and b) and 48 provide data obtained in accordance with the invention.
Figure 41B:
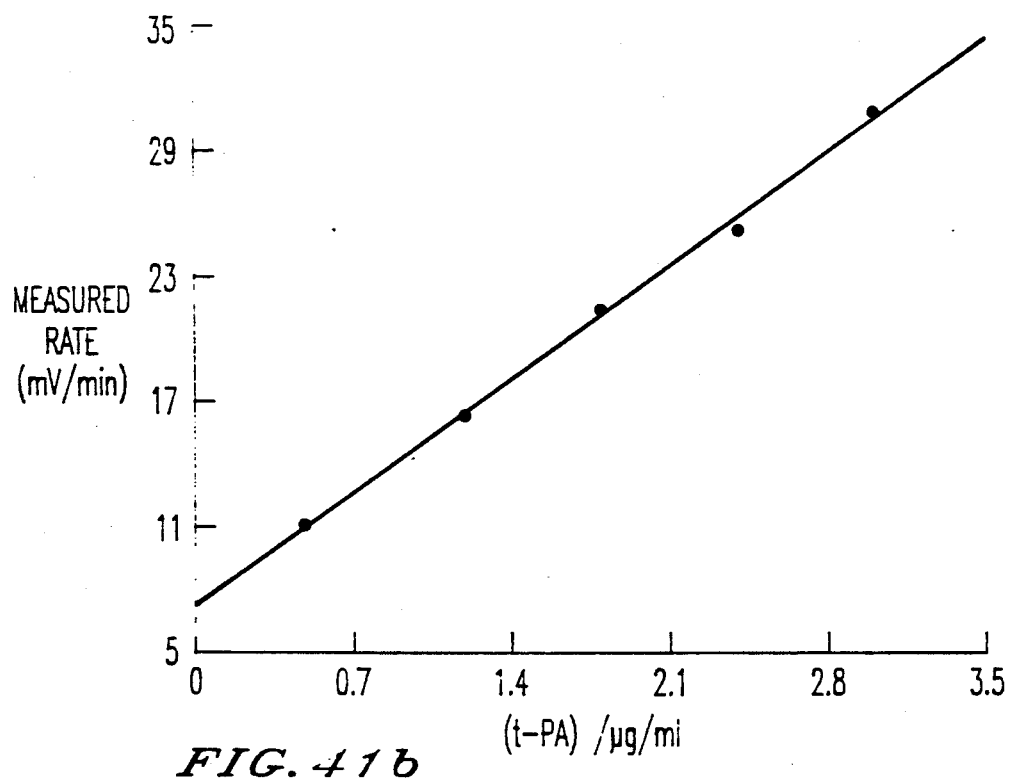

When 40 microliters of citrated whole blood, serum or plasma was applied to the reaction slide, the reagents within dissolved instantaneously, and the liquid portion of the sample rapidly permeated the membrane. Depending on the concentration of t-PA intensity. This color change was detected by the decrease in reflected light at 400 nanometers, as seen in a plot of photodetector amplifier voltage versus time. The establishment of a downward slope, after an initial lag phase, provided a useful kinetic measurement of t-PA concentration as shown in FIG. 41a. The slope or measured rate of the reaction was plotted against actual concentration of t-PA in the whole blood sample. A standard curve approximated by a straight line resulted as shown in FIG. 41b. This standard curve could then be used to determine t-PA concentrations in samples of whole blood (or serum, or plasma) once the measured rate of reaction was obtained.

Example 2 t-PA Assay:
A similar experiment was performed. In this case, 10 ul 0.1 M S-2251 was air dried onto membrane circles adhered to slide tops before the tops were placed on the slides. The remaining reagents were then freeze dried in the slide. The results obtained were similar to those discussed in Example 1.

Example 3

Plasminogen (total available Plasmin) Assay:
Reagents:
(1) 10 microliters 5,000 IU t-PA
(2) 18 microliters 0.1M S-2251 (Helena Labs) diluted in water.

The reagents were freeze dried in reagent slides containing membrane circles described earlier.

Figure 42:
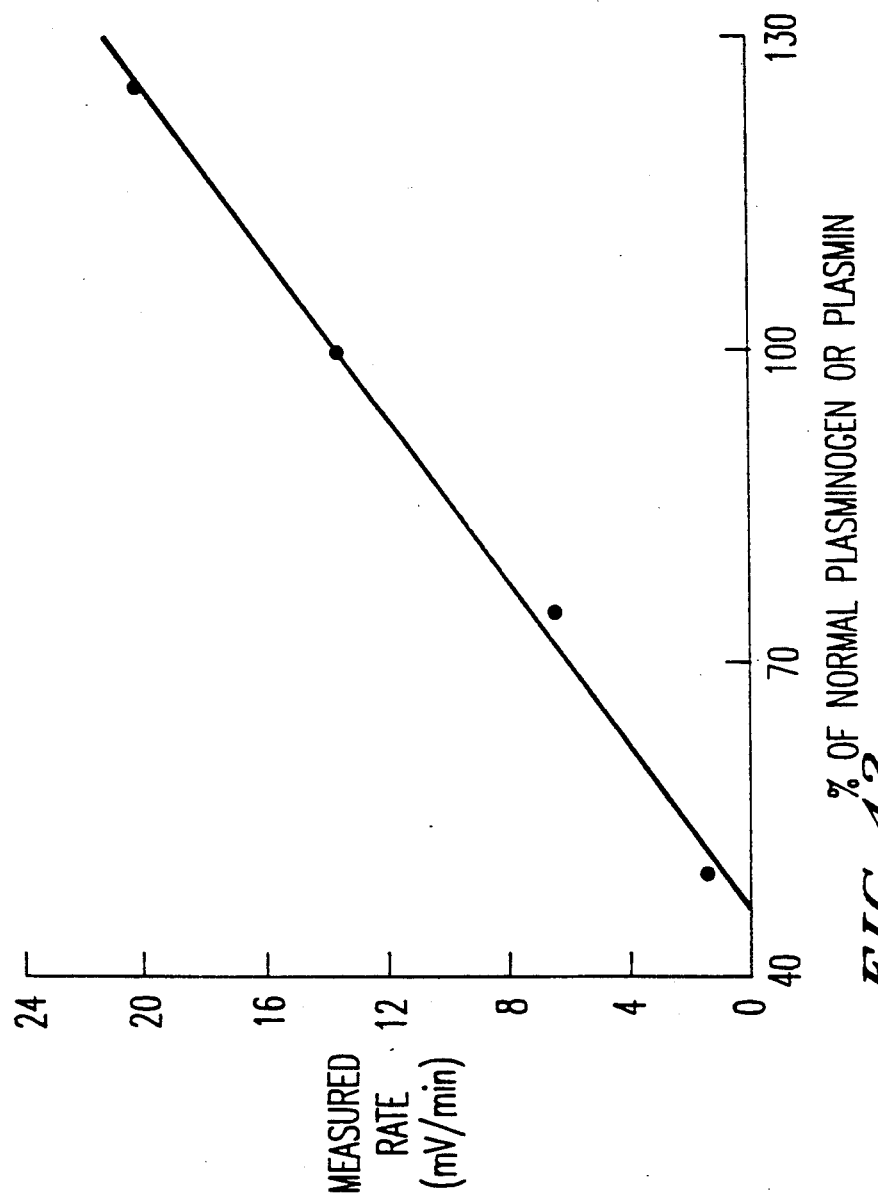

Depending on the concentration of plasminogen in the sample, the plasma assumed a yellow color of differing intensity. As in Example 1, the measured rate could be obtained and utilized to construct a standard curve for interpretation of assay data on whole blood samples as shown in FIG. 42.

Example 4

Free Plasmin Assay:
Reagent:
(1) 28 microliters 0.1M S-2251 (Helena Labs) diluted in water.

The reagent was freeze dried in reagent slides.

Depending on the concentration of free plasmin in the sample, the plasma assumed a yellow color of differing intensity. Results were similar to those seen in Example 3.

Example 5

Alpha-2-Antiplasmin Assay:
Reagents:
(1) 18 microliters 0.3 CU human plasmin (Ortho) dissolved in 50% glycerol in 2 mmol/1 HCl.
(2) 10 microliters 0.1M S-2251 (Helena Labs) dissolved in water.

The reagents were freeze dried in reagent slides.

The plasma assumed a yellow color which corresponded inversely to the concentration of alpha-2-antiplasmin in the sample.

CLOT LYSIS ASSAY EXAMPLES

Figure 43:
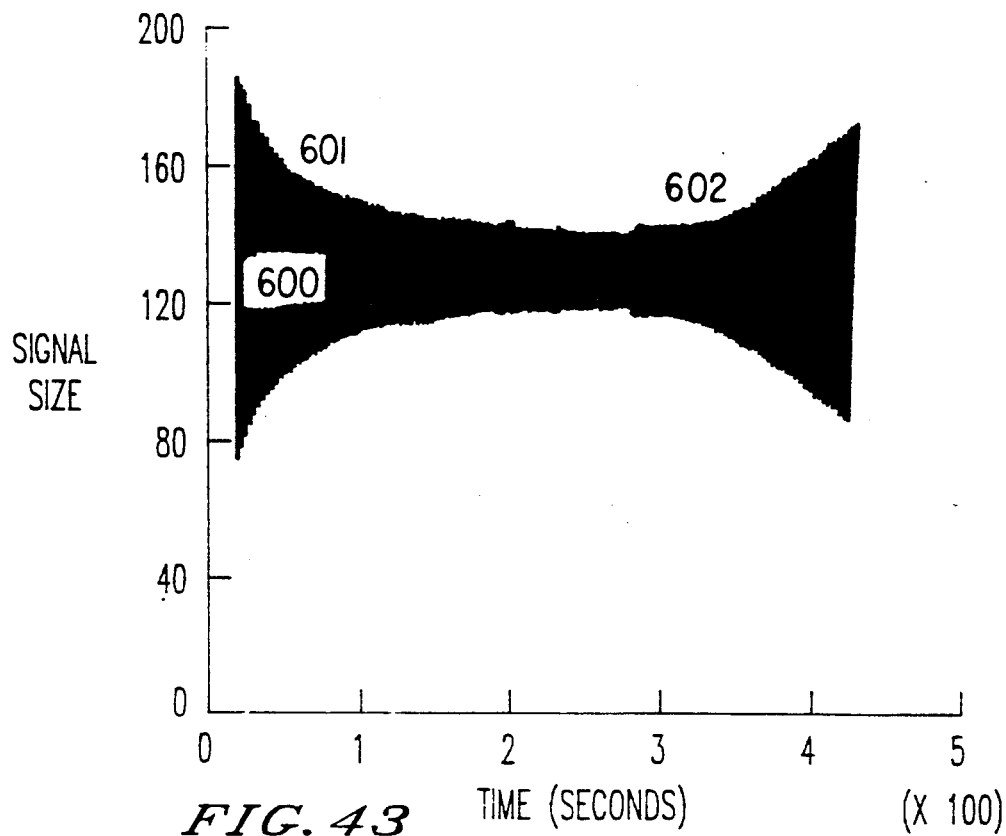
Figure 44A:
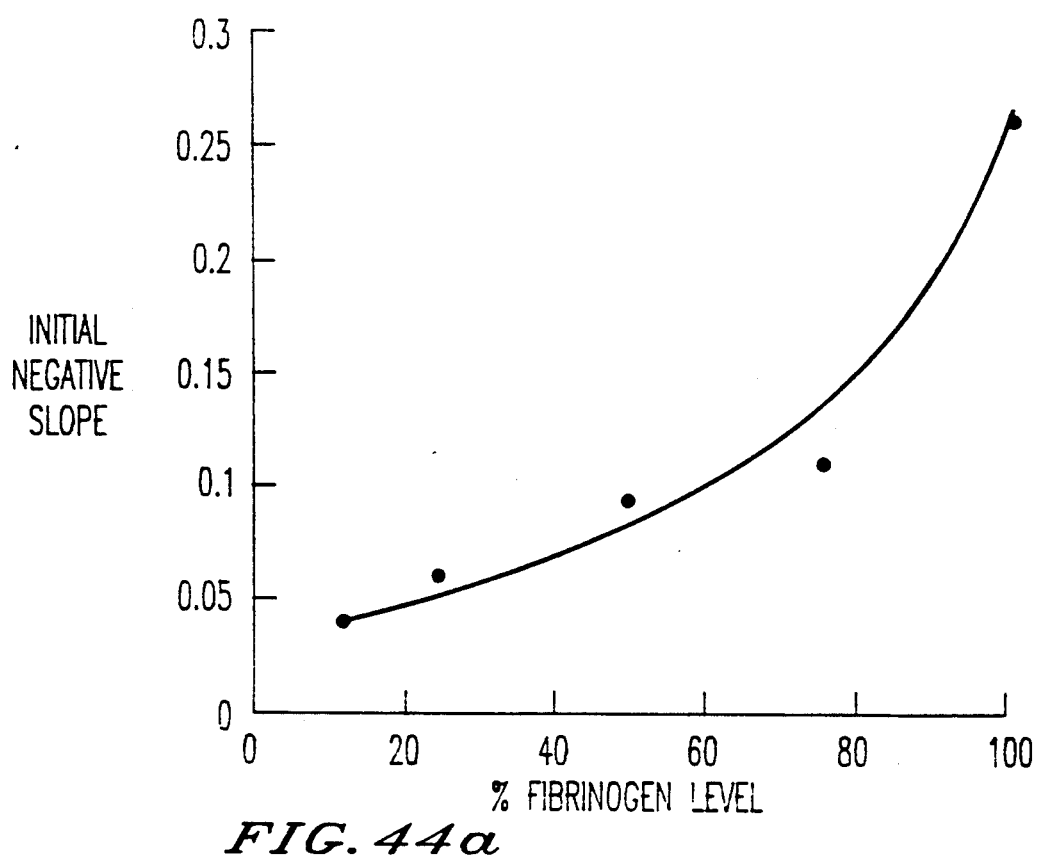
Figure 44B:
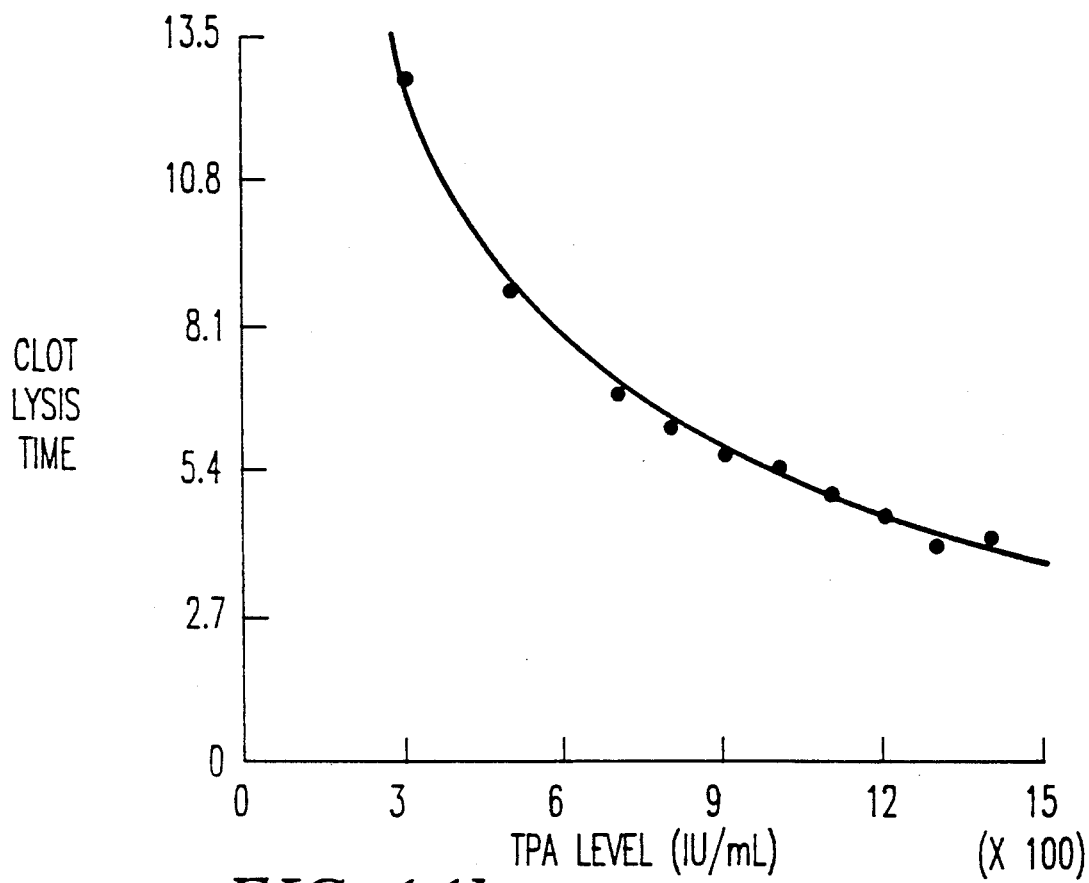
Figure 45:
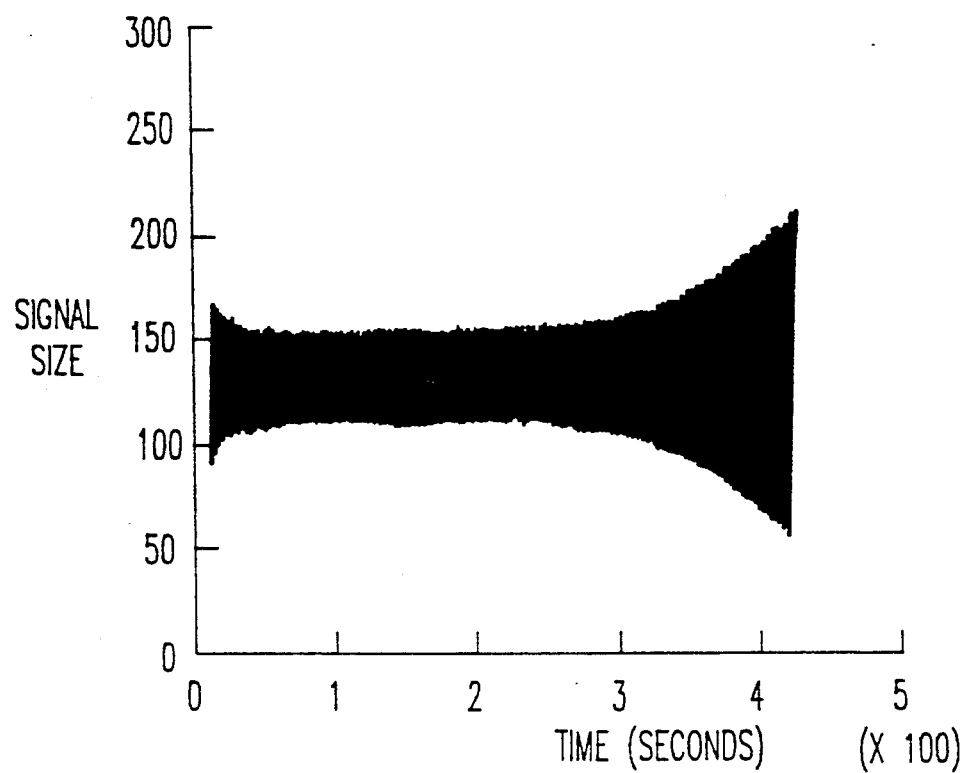

1. A slide was prepared for endogenous clot lysis monitoring containing the following mixture of reagents: Bovine Thrombin, 25 units/ml (Sigma Chemical Co.) diluted in Owen's Veronal buffer; 10 mg/ml $Fe_3O_4$ particles (average size 0.3 micron by the Fisher Method) and plasminogen, 0.2 mg/ml mixed with thrombin to achieve a 0.2 mg/ml concentration. The reagents were added to a standard reaction slide. The slide was freeze dried, packaged in foil, and stored under refrigeration until use. When used, the slide was placed in an instrument for monitoring paramagnetic particle movement, as described elsewhere in this patent application and brought automatically to a temperature of 37° C. A fresh, citrated whole blood sample containing a therapeutic level of tissue plasminogen activator (t-PA, 1000 IU/ml) was added to the sample well. The resulting signal showed clot formation and, after a few minutes, subsequent onset of clot lysis. In arbitrary signal size (voltage) units versus time, the entire waveform is shown in FIG. 43. As seen, the waveform is greatly compressed in time so that it is not possible to identify the individual peaks as in FIGS. 3 and 4. The clot formation region (600) in FIG. 43 has a negative slope (601) which appears proportional to fibrinogen concentration in the sample. This is shown in FIG. 44a. In addition to enabling clot formation to be monitored, a clot lysis onset time 602 in FIG. 43 was found to be inversely proportional to the t-PA concentration as shown in FIG. 44b.

2. A slide was prepared for endogenous clot lysis susceptibility monitoring. The slide utilized was a standard reaction slide, as in Example 1, and contained the same concentrations of thrombin, paramagnetic particles, and plasminogen. In addition, the slide reagents contained 400 IU of recombinant t-PA. The slide was freeze dried, as in Example 1, and stored in a similar manner. The slide was used in the same instrument as in the previous example. The sample consisted of fresh, citrated whole blood prior to administration of thrombolytic therapy. The resulting signal showed clot formation which progressed normally, and, after a few minutes, subsequent onset of clot lysis. The susceptibility of the patient's clot to lysis by t-PA for the system employed, at the concentration of t-PA employed, was evident. This type of assay may be useful as an indicator of susceptibility to lysis or as a screening tool.

Figure 46A:
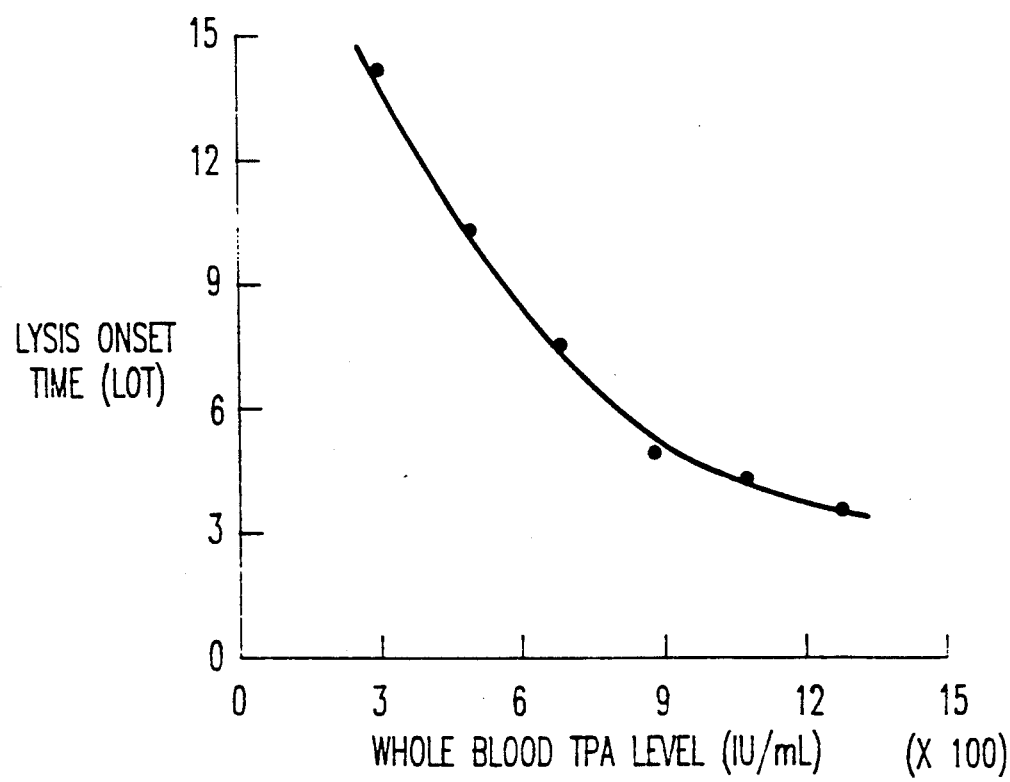
Figure 46B:
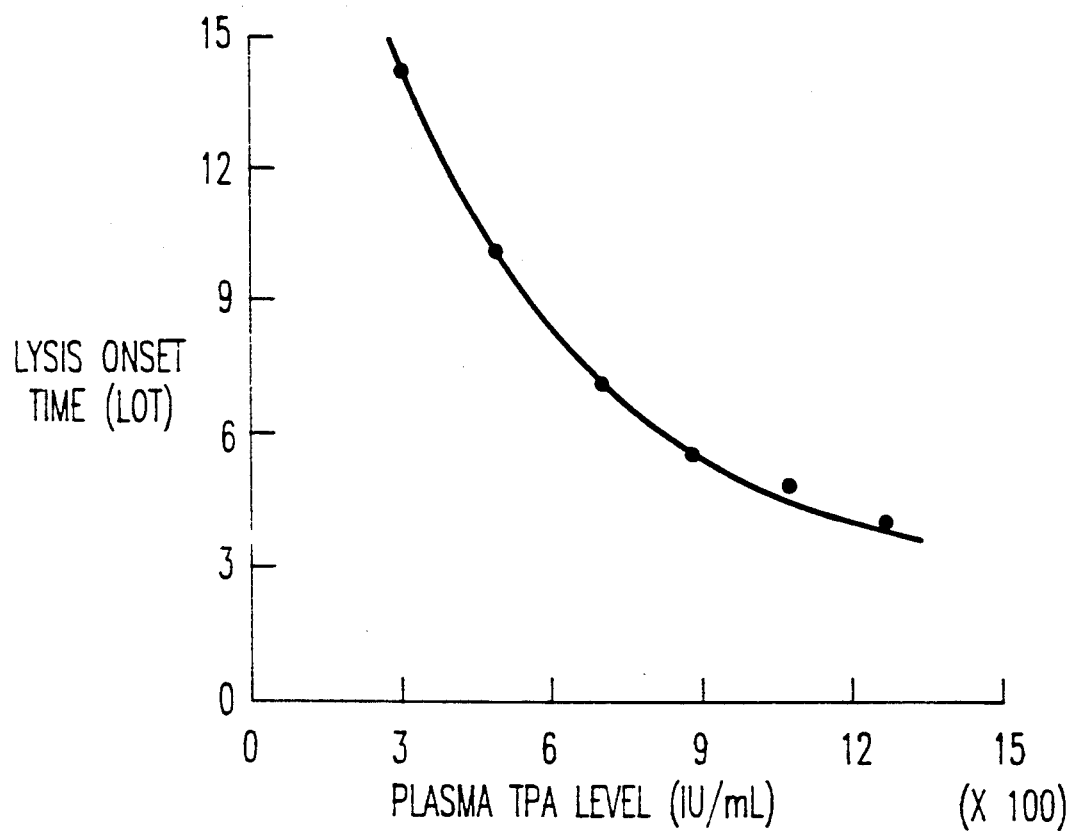

3. A slide was prepared for an exogenous clot lysis assay (or standardized clot lysis assay) consisting of reagents air dried on a reaction slide in the first stage and freeze dried in the second stage. Reagents added in the first stage to the reaction slide were bovine-thrombin; 30 U/ml, and $Fe_3O_4$ particles, 15 mg/ml. After drying, fibrinogen, 2 mg/ml, and plasminogen, 0.02 mg/ml of final solution were added. After clot formation was achieved, the slide was freeze dried. The slide was then placed in an instrument as in the prior examples, and a sample of fresh, citrated whole blood containing t-PA was added to the sample well. A waveform similar to that shown in FIG. 43 resulted. The time of onset of clot lysis was found to be proportional inversely to the t-PA concentration in the sample as shown in the standard curve in FIG. 46a. The assay was repeated using plasma from the same citrated sample with similar results as shown in FIG. 46b.

4. A slide was prepared as in Example 3, except that plasminogen was omitted and streptokinase added in the first stage. The resultant slide was placed in an instrument as in the previous examples, and a sample of fresh, citrated whole blood containing plasminogen was added to the sample well. The time of onset of clot lysis was found to be proportional inversely to the concentration of plasminogen in the sample.

5. A slide was prepared for an exogenous "clot" lysis assay for plasminogen or plasminogen activator using cross-linked casein molecules. For a plasminogen activator assay, plasminogen was added to the slide contents. For a plasminogen assay, t-PA or streptokinase was added and plasminogen omitted. Casein (Eastman Kodak) was dissolved maximally in 0.1 molar sodium bicarbonate solution to which 45 mg of $Fe_3O_4$ particles and 0.2 g of EDC (Sigma Chemical Co., carbodiimide crosslinking reagent) were added and mixed at room temperature for 30 minutes. The resulting solution was spread onto reaction slide bottoms, when the slides were assembled, air dried and utilized, as in the previous examples, for whole blood assays, a correlation between lysis time, as indicated paramagnetic particle movement, and plasminogen activator and plasminogen concentrations was found.

BLOOD CLOTTING ASSAY EXAMPLES

1. Reaction slides as shown in FIG. 17 were prepared utilizing thromboplastin calcium reagent and freeze dried, as discussed previously, and stored under refrigeration until used to perform prothrombin time assays. Assays were performed on an instrument prototype called Coag I. Details of instrument monitoring, signal processing, and data handling were discussed previously.

This study reports on samples of citrated whole blood and plasma from 59 patients, including patients with possible coagulation disorders. The correlation coefficients of Coag I against the reference method (Coag-A-Mate X2, Organon Teknika; Thromboscreen, Pacific Hemostatis) was 0.97 and 0.98 for plasma and blood, respectively. The Coag I data points represent single determinations, and the reference method points represent the average of two determinations for each sample.

Figure 47A:
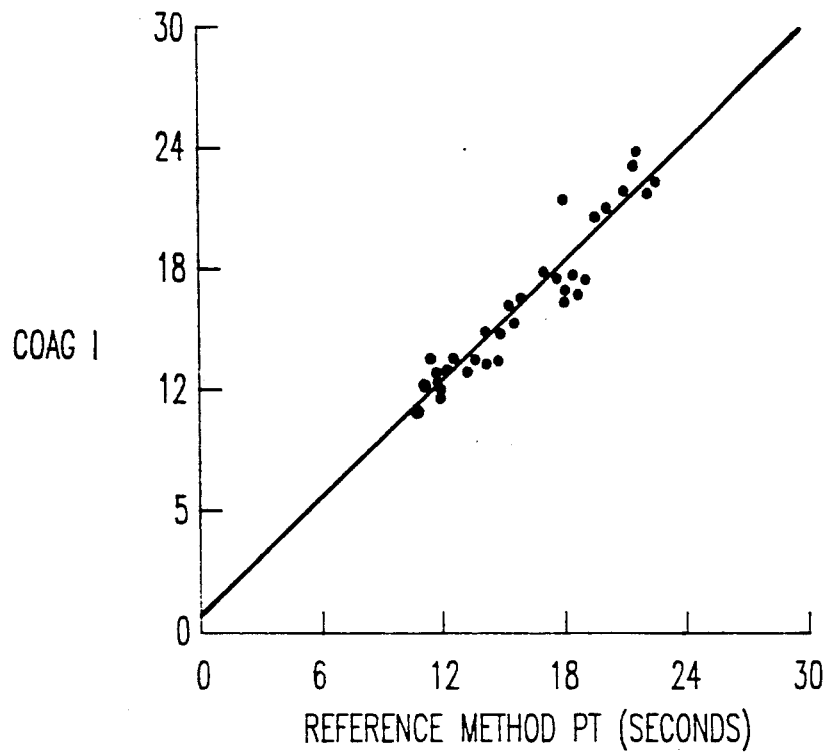
Figure 47B:
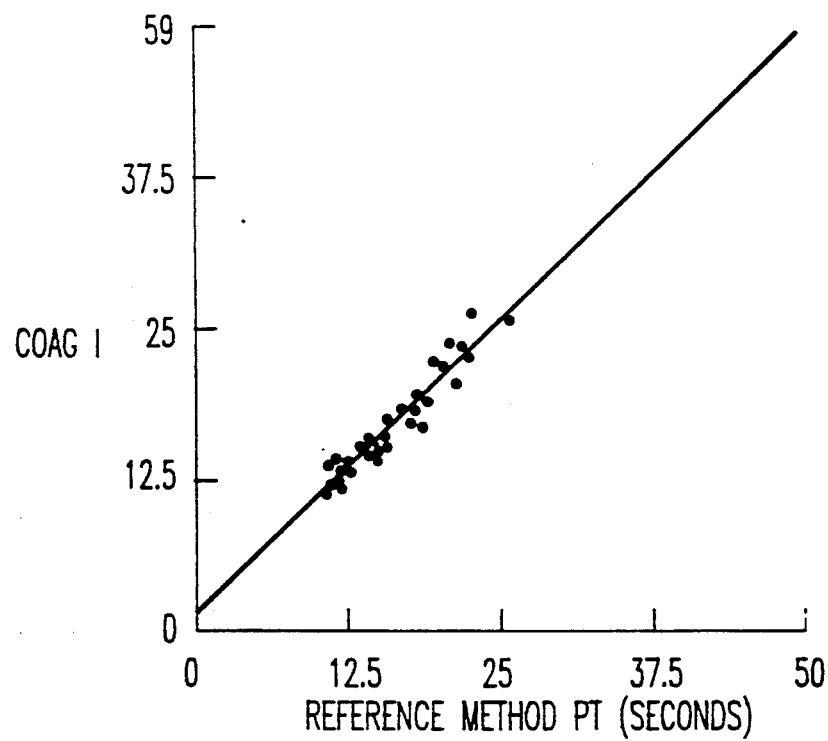

FIG. 47 shows the excellent results obtained for the plasma samples at the left and for whole blood samples at the right. Both sets of data are plotted against the reference method mean values using plasma. The tabulated summary at the bottom of FIG. 47 shows the resulting statistical values.

2. Using reaction slides prepared as in the previous example, studies were conducted to explore the feasibility of using freshly drawn finger stick samples to perform an even faster, more convenient PT test. Table I shows the results obtained for a representative study. Seven optical heads were employed to collect data rapidly. Whole blood was obtained from an individual donor using an "Autolet" finger puncture device (Ulster Scientific). Seventeen PT tests were performed using multiple finger sticks and multiple fingers. In these studies, the finger was not excessively squeezed, and the sample was deposited on the reaction slide within approximately 20 seconds. Under these conditions, there do not seem to be any artifacts arising from the donor's tissue thromboplastin. Within fifteen minutes of the conclusion of testing, whole venous blood was drawn from the same donor into a sterile syringe without anticoagulant. It was then possible to test this blood during a period lasting approximately five minutes. PT assays were immediately initiated by a team of three people in the laboratory, while two additional samples were collected from the donor by drawing into evacuated tubes containing 3.2% buffered citrate anticoagulant. One citrated tube was spun to recover plasma for subsequent testing. The other was tested as citrated whole blood.

From the results in the table below, the mean for the four sample types ranged from 12.0 to 13.3 seconds. Coefficients of variation, expressed as percent, ranged from 2.5% for the 60 plasma determinations to 5.4% for the 17 finger stick determinations.

| Sample Type | Finger | Venous | CitWB | CitPlasma |
|---|---|---|---|---|
| Number | 17 | 30 | 60 | 60 |
| Mean | 12.9 | 13.3 | 12.6 | 12.0 |
| Standard deviation | 0.7 | 0.5 | 0.5 | 0.3 |
| Minimum | 11.8 | 12.2 | 11.7 | 11.2 |
| Maximum | 14.3 | 14.4 | 13.6 | 12.6 |
| Range | 2.5 | 2.2 | 1.9 | 1.4 |
| Coef. of Variation | 5.4% | 3.8% | 4.0% | 2.5% |

3. Reaction slides as shown in FIG. 17 were prepared utilizing partial thromboplastin reagent, calcium and a particulate activator and freeze dried to prepare APTT dry reagent slides. The slides were stored under refrigeration until used to perform activated partial thromboplastin time assays. These assays would be one stage APTT assays, as opposed to conventional laboratory assays which use two stage methods, the first stage consisting of a 5 minute incubation prior to calcium addition.

Figure 48:
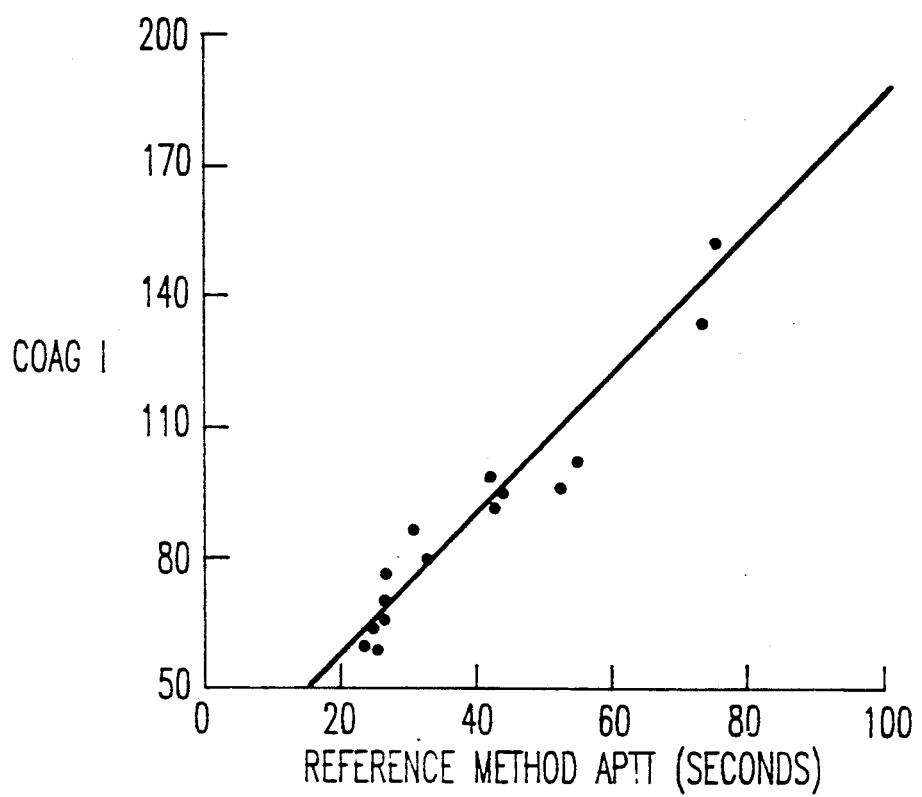

FIG. 48 shows a plot of the APTT comparison study. Dry chemistry slides for a single stage APTT assay using a Coag-I prototype system were tested and compared with the reference method. The same reference instrument and Pacific Hemostasis reagent for APTT were employed by the reference laboratory. The results were very encouraging, as may be seen from the data. The one stage APTT method, as shown by these data, correlates well with the two stage reference method. Although the one stage method has longer reaction times, the overall test time is shorter, since the 5 minute incubation step was not necessary. The one stage test is also simpler to perform. If desired, the one stage endpoints may be electronically adjusted, as explained previously, to be reported as equivalent to the two stage endpoint values.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. In a coagulation assay comprising combining a coagulation assay reagent and a whole blood sample or plasma sample and obtaining a coagulation assay measurement, the improvement comprising adding to a dry coagulation assay reagent containing magnetic particles distributed substantially homogeneously therethrough, arranged in a substantially flattened format, and under the influence of an oscillating magnetic field or moving permanent magnetic field, or both, a whole blood sample or a plasma sample thereby substantially simultaneously initiating movement of said magnetic particles and the coagulation assay measurement and monitoring movement of said magnetic particles to obtain said assay measurement.

2. A method for performing a clot lysis assay measurement on a whole blood or plasma sample fibrinolytically active containing a component of the blood coagulation cascade system, comprising:
  (i) adding a measured amount of said sample to a dry reagent arranged in a substantially flattened configuration and containing a fibrin clot from whole blood or plasma and magnetic particles distributed substantially homogeneously throughout said clot, thereby substantially simultaneously initiating the assay measurement, wherein said reagent containing magnetic particles is subjected to (ia) an oscillating magnetic field or (ib) a moving permanent magnetic field or (ic) a combination of an oscillating magnetic field and a stationary permanent magnetic field; and
  (ii) obtaining said assay measurement by monitoring the movement of said magnetic particles induced by (ia), (ib) or (ic).

3. A method for performing a clot lysis assay measurement, comprising:
  (i) contacting a whole blood or plasma sample and a dry composition arranged in a substantially flattened configuration and containing at least one whole blood or plasma clot producing reagent and magnetic particles distributed substantially homogeneously throughout said composition to obtain a clot containing magnetic particles; then
  (ii) adding a whole blood or plasma clot lysis assay reagent to said clot, thereby substantially simultaneously initiating said clot lysis assay measurement, and optically monitoring movement in said magnetic particles induced by (ia) an oscillating magnetic field or (ib) a moving permanent magnetic field or (ic) a combination of an oscillating magnetic field and a stationary permanent magnetic field, to obtain said clot lysis assay measurement.

4. A method for performing a clot lysis assay measurement, comprising:
  contacting a whole blood or plasma sample and a dry composition arranged in a substantially flattened configuration, containing at least one whole blood or plasma clot producing reagent and magnetic particles distributed substantially homogeneously therethrough, and being subjected to (a) an oscillating magnetic field or (b) a moving permanent magnetic field or (c) a combination of an oscillating magnetic field and a stationary permanent magnetic field, thereby substantially simultaneously initiating movement of said magnetic particles and said clot lysis assay measurement and obtaining the formation of a clot containing magnetic particles, and subsequently allowing lysis of said clot to proceed, thereby obtaining said clot lysis assay measurement by monitoring movement of said magnetic particles.

5. The method of claim 4, wherein, either said sample contains a clot lysis assay reagent or said dry composition further contains a clot lysis assay reagent.

6. A method for performing a clot lysis assay measurement on a whole blood or plasma sample containing a fibrinolytically active component of the blood coagulation cascade system, comprising:
  contacting a whole blood or plasma sample and a fibrin clot arranged in a substantially flattened configuration and containing magnetic particles distributed substantially homogeneously therethrough, said clot being subjected to (a) an oscillating magnetic field or (b) a moving permanent magnetic field or (c) a combination of an oscillating magnetic field and a stationary permanent magnetic field, thereby substantially simultaneously initiating movement of said magnetic particles and the clot lysis assay measurement, and obtaining the clot assay measurement by monitoring movement of said magnetic particles.

7. The method of claim 6, wherein said whole blood or plasma sample contains a clot lysis assay reagent.

8. A method for performing a coagulation assay on a whole blood or plasma sample, comprising:
  (i) adding a first, whole blood or plasma, component of the assay to a second component of the assay, wherein said second component comprises a dry coagulation assay reagent arranged in a substantially flattened configuration and containing magnetic particles distributed substantially homogeneously therethrough, and wherein said second is subjected to (ia) an oscillating magnetic field or (ib) a moving permanent magnetic field or (ic) a combination of an oscillating magnetic field and a stationary permanent magnetic field, whereby said adding of said first component to said second component substantially simultaneously initiates movement of said magnetic particles and the coagulation assay measurement; and
  (ii) monitoring movement induced in said magnetic particles by (ia) or (ib) or (ic) to obtain said coagulation assay measurement.

9. The method of claim 8, wherein said coagulation assay is a clotting assay.

10. The method of claim 9, wherein said sample is whole blood.

11. The method of claim 9, wherein said sample is plasma.

12. The method of claim 9, wherein said magnetic particles are induced to move by applying an oscillating magnetic field thereto.

13. The method of claim 9, wherein said magnetic particles are induced to move by applying a moving permanent magnetic field thereto.

14. The method of claim 9, wherein said dry reagent comprises thromboplastin and a calcium salt.

15. The method of claim 8, wherein said method is carried out in an element for performing said coagulation assay, said method comprising adding said sample to said element, wherein said element comprises a channel structure defining a sample well and a reaction volume in fluid communication with each other, said reaction volume containing said second component, said channel structure having a geometry causing said sample placed in said sample well to be drawn into and filling said reaction volume via capillary action, wherein, after said reaction volume is filled, said sample remains stationary therein.

16. The method of claim 15, wherein said element further comprises a means for channeling light from an outside source to said reaction volume.

17. The method of claim 16, further comprising using a means for detecting light scattered or absorbed or reflected from said reaction volume.

18. The method of claim 15, wherein said element is disposed in sufficiently close proximity to a permanent magnet and to an electromagnet such that said permanent magnet and said electromagnet provide said combination of an oscillating magnetic field and a stationary permanent magnetic field.

19. The method of claim 18, wherein said element is situated between said permanent magnet and said electromagnet.

20. The method of claim 8, wherein (i) said coagulation assay is a clot lysis assay, (ii) said first component is a measured amount of a whole blood or plasma clot dissolving reagent or of a sample containing a whole blood or plasma clot dissolving component, and (iii) said second component is a whole blood or plasma clot containing magnetic particles.

21. The method of claim 20, wherein said clot lysis assay is a tissue plasminogen activator assay.

22. An element for performing a liquid sample assay, said element comprising therein a channel structure defining a sample well and a reaction volume in fluid communication with each other, wherein said reaction volume contains at least one dry assay reagent arranged in a substantially flattened configuration and containing magnetic particles distributed substantially homogeneously therethrough, and wherein said reaction volume is defined by an upper surface having attached thereto a reflectance layer comprising a semipermeable matrix, said channel structure having a geometry causing the liquid sample, when placed in said sample well, to be drawn into and filling said reaction volume via capillary action, after said reaction volume is filled said liquid sample remains stationary.

23. The element of claim 22, wherein said semipermeable layer is a means for monitoring an assay carried out in said reaction volume.

24. The element of claim 22, wherein at least one dry assay reagent is contained within said semipermeable layer.

25. The element of claim 22, said element comprising at least one dry assay reagent layer in contact with a major surface of said semipermeable matrix not affixed to said reflectance layer.

26. The element of claim 25, wherein said dry assay reagent contains at least one enzyme or zymogen of the blood coagulation cascade system.

27. The element of claim 22, wherein said semipermeable matrix is made up of one or more layers of a gel or a membrane, wherein each gel or membrane layer contains at least one dry assay reagent.

28. The element of claim 22, wherein said semipermeable matrix is a layer of gel or a multilayer gel structure or a non-gel membrane with a layer of gel or multilayer gel structure attached thereto.

29. The element of claim 22, wherein said upper surface has attached thereto a plurality of semipermeable reflectance layers, wherein each reflectance layer is separately attached to said upper surface and capable of being utilized as a separate means for monitoring a reaction.

30. The element of claim 22, wherein said semipermeable matrix, or a plurality of said semipermeable matrices, is attached to said upper surface, wherein each semipermeable matrix, or each said plurality of said semipermeable matrices, is capable of being utilized to monitor a reaction.

31. A method for performing a coagulation assay measurement, comprising:
(i) adding a whole blood or plasma sample to the sample well of an element comprising:
a channel structure defining a sample well and a reaction volume in fluid communication with each other, wherein said reaction volume is defined by an upper surface having attached thereto a reflectance layer, comprising a semipermeable matrix wherein said reaction volume contains a measured amount of at least one dry coagulation assay reagent arranged in a substantially flattened configuration and containing magnetic particles distributed substantially homogeneously therethrough, wherein a specific volume of said sample is drawn into said reaction volume by capillary action and contacts, together with said semipermeable layer, said reagent to thereby substantially simultaneously initiate said coagulation assay measurement; and
(ii) performing said coagulation assay measurement by measurement the reflectance of said semipermeable layer.

32. A dry coagulation assay reagent comprising magnetic particles distributed substantially homogeneously therethrough wherein said reagent is selected from the group consisting of:
(1) one member selected from the group consisting of prothrombin time reagents and (ii) prothrombin time reagents and calcium salts;
(2) partial thromboplastin time reagents with calcium chloride;
(3) partial thromboplastin time reagents with calcium chloride and clot formation activators;
(4) thrombin or a snake venom with thrombotic activity;
(5) fibrin, or plasminogen and fibrin;
(6) plasminogen activator assay reagents containing (i) plasminogen and (ii) either fibrin, a snake venom with thrombotic activity, or thrombin;
(7) plasminogen assay reagents containing (i) a plasminogen activator and (ii) either fibrin, a snake venom with thrombotic activity, or thrombin;
(8) natural and synthetic plasminogen activators;

(9) α-2-antiplasmin assay reagents containing fibrin and plasmin; and

(10) combinations thereof.

33. The reagent of claim 32, wherein said reagent is thromboplastin or thromboplastin and a calcium salt.

34. The reagent of claim 32, wherein said reagent is a partial thromboplastin time reagent with calcium chloride.

35. The reagent of claim 32, wherein said reagent is a partial thromboplastin reagent with calcium chloride and a clot formation activator.

36. The reagent of claim 32, wherein said reagent is thrombin or a snake venom with thrombotic activity.

37. The reagent of claim 32, wherein said reagent is fibrin, plasminogen and fibrin, a snake venom with thrombin-like activity, or thrombin.

38. The reagent of claim 37, comprising either said snake venom with thrombotic activity or a combination of said snake venom with thrombotic activity and thrombin.

39. The reagent of claim 32, wherein said reagent is a plasminogen assay reagent containing (i) a plasminogen activator and (ii) either fibrin, a snake venom with thrombotic activity, or thrombin.

40. The reagent of claim 39, comprising either said snake venom with thrombotic activity or a combination of said snake venom with thrombotic activity and thrombin.

41. The reagent of claim 32, wherein said reagent is one member selected from the group consisting of streptokinase and urokinase.

42. The reagent of claim 32, wherein said reagent comprises one member selected from the group consisting of natural and synthetic tissue plasminogen activators.

43. The reagent of claim 32, wherein said reagent is an α-2-antiplasmin assay reagent containing fibrin and plasmin.

44. The dry coagulation assay reagent of claim 32, wherein said reagent comprises:
   (4) thrombin or a snake venom with thrombotic activity; and
   (8) one member selected from the group consisting of natural and synthetic plasminogen activators.

45. The dry coagulation assay reagent of claim 32, wherein said reagent comprises at least one member selected from the group consisting of streptokinase, tissue plasminogen activator and urokinase.

46. A kit for performing a coagulation assay, comprising, in one or more containers, a permanent magnet, a timing means, and an element containing at least one dry coagulation assay reagent arranged in a substantially flattened format and containing magnetic particles distributed substantially homogeneously therethrough.

47. The kit of claim 46, further comprising a transfer pipette.

48. A system for performing a coagulation assay measurement, comprising:
   (i) an instrument with a means for temperature control, a means for producing an oscillating magnetic field or for moving a permanent magnetic field, an illuminating means, and a photometric monitoring means; and
   (ii) an element for performing said coagulation assay, said element comprising a channel structure defining a sample well and reaction volume in fluid communication with each other, said channel structure having a geometry causing a liquid sample placed in said sample well to be drawn into and filling said reaction volume via capillary action, said reaction volume comprising at least one dry coagulation assay reagent arranged in a substantially flattened configuration and containing magnetic particles distributed substantially homogeneously therethrough.

49. The system of claim 48, further comprising a transfer pipette.

50. The system of claim 49, wherein said transfer pipette is made of an essentially nonthrombogenic material, comprises a vented end, is capable of being filled with a liquid sample by capillary action, and is capable of expelling said liquid sample by means of pressure after covering or sealing said vented end.

51. The system of claim 48, wherein said instrument further comprises a heating means comprising a resistive heater strip and a thermistor situated in close proximity to said element.

52. The system of claim 48, wherein said element is suitable for performing a whole blood coagulation assay, said channel structure having a geometry causing a blood sample placed in said sample well to be drawn into and filling said reaction volume via capillary action, wherein after said reaction volume is filled, said blood sample remains stationary therein, and wherein said element further comprises an optically or magnetically encodable information means, or both, capable of providing at least one of calibration, quality control, test parameter and patient information.

53. The system of claim 48, wherein said illuminating means includes one or more light sources to illuminate said element and wherein said photometric monitoring means comprises one or more detectors for photometrically monitoring chromogenic or chromomodulating species present in said reaction volume.

54. A system for performing a coagulation assay, comprising:
   (i) a reaction element comprising (1) a sample well for receiving a liquid sample and (2) a reaction chamber containing a dry coagulation assay reagent arranged in a substantially flattened configuration and in which is embedded, substantially homogeneously therethrough, magnetic particles;
   (ii) said sample well and said reaction chamber being in fluid communication through a transport zone of geometry such that a volume of liquid sample placed in said sample well and corresponding to the volume of said reaction chamber is transported from said sample well to said reaction chamber simultaneously;
   (iii) means for optically monitoring said reaction chamber;
   (iv) means for subjecting said reaction chamber to an oscillating magnetic field;
   (v) whereby, when said sample is introduced into said reaction chamber, said dry coagulation assay reagent is solubilized and said magnetic particles are thereby freed to move in an oscillating pattern induced by said oscillating magnetic field, thus providing a measurement of the kinetics of said coagulation assay corresponding to changes in the degree of said magnetic particles movement relative to said oscillating magnetic field.

55. The system of claim 54, wherein said dry reagent is a blood coagulation promoting reagent.

56. The system of claim 54, comprising a means for controlling the moment transport of said liquid sample from said sample well to said reaction chamber is initiated.

57. The analytical system of claim 54, comprising a plurality of reaction chambers in fluid communication with said sample well, and means for transporting a whole blood or plasma sample from one of said plurality of reaction chambers to another of said plurality of reaction chambers.

58. A method for performing a coagulation assay, comprising:
(i) subjecting to an oscillating magnetic field a reaction element bearing (1) a sample well for receiving a whole blood or plasma sample and (2) a reaction chamber containing a dry coagulation assay reagent arranged in a substantially flattened format and in which is embedded, substantially homogeneously therethrough, magnetic particles, said sample well and reaction chamber being in fluid communication through a transport zone of geometry such that a volume of sample placed in said sample well and corresponding to the volume of said reaction chamber is transported from said sample well to said reaction chamber simultaneously;
(ii) adding a whole blood or plasma sample susceptible to coagulation to said sample well whereby at least a part of said sample is introduced simultaneously to said reaction chamber, said reagent is solubilized and said particles are freed to move in an oscillating pattern induced by said oscillating magnetic field; and
(iii) optically monitoring said reaction chamber to measure kinetics for the coagulation assay corresponding to changes in the degree of said particle movement relative to said magnetic field.

* * * * *